United States Patent [19]
Danishefsky et al.

[11] Patent Number: 5,708,163
[45] Date of Patent: Jan. 13, 1998

[54] SYNTHESIS OF THE BREAST TUMOR-ASSOCIATED ANTIGEN DEFINED BY MONOCLONALANTIBODY MBRL AND USES THEREOF

[75] Inventors: Samuel J. Danishefsky, Englewood, N.J.; Mark T. Bilodeau, New York, N.Y.; Shuang Hua Hu, New York, N.Y.; Tae Kyo Park, New York, N.Y.; John T. Randolph, Lake Bluff, Ill.; In Jong Kim; Philip O. Livingston, both of New York, N.Y.

[73] Assignee: Sloan-Kettering Institute of Cancer Research, New York, N.Y.

[21] Appl. No.: 430,355

[22] Filed: Apr. 28, 1995

Related U.S. Application Data

[63] Continuation-in-part of Ser. No. 213,053, Mar. 15, 1994.
[51] Int. Cl.$^6$ .............................. C07H 1/00; C07H 5/06; C07H 17/00; C08B 37/00
[52] U.S. Cl. .................. 536/124; 536/17.9; 536/55.2; 536/55.3; 536/120; 536/123.1; 536/126
[58] Field of Search ..................... 536/17.9, 55.2, 536/55.3, 120, 123.1, 124, 126

[56] References Cited

FOREIGN PATENT DOCUMENTS

WO9305803   4/1993   WIPO.

OTHER PUBLICATIONS

Behar, V. and S.J. Danishefsky, "A Highly Convergent Synthesis of the Lewis$^y$ Blood Group Determinant in Conjugatable Form" Angewandte Chem. Int. Ed. Eng. (1994) 33(14): 1468–1470 (Exhibit 2).

Bremer, E.G., "Characterization of a Glycosphingolipid Antigen Defined by the Monoclonal Antibody MBr1 Expressed in Normal and Neoplastic Epithelial Cells of Human Gland", J. Biol. Chem. (1984) 259: 14773–14777 (Exhibit 3).

Danishefsky, S.J., et al., "Application of the Glycal Assembly Method to the Concise Synthesis of Neoglycoconjugates of Le$^y$ and Le$^b$ Blood Group Determinants and H-Type I and H-Type II Oligosaccharides", J. Am. Chem. Soc. (1995) 117: 5701–5711 (Exhibit 4).

Dennis, J., Oxford Glycosystems Glyconews Second 1992 (Exhibit 5).

Feizi, T.,"Carbohydrate antigens in human cancer", Cancer Surveys (1985) 4: 245–269 (Exhibit 6).

Gorden, D.M. and Danishefsky, S.J., "Displacement reactions of a 1,2-anhydro-α-D-hexopyranose: installation of useful functionality at the anomeric carbon", Carbohydr. Res. (1990) 206: 361–366 (Exhibit 7).

Hakomori, S., "Aberrant Glycosylation in Cancer Cell Membranes as Focused on Glycolipids: Overview and Perspectives[1]", Cancer Res. (1985) 45: 2405–2414 (Exhibit 8).

(List continued on next page.)

*Primary Examiner*—John Kight
*Assistant Examiner*—Everett White
*Attorney, Agent, or Firm*—John P. White

[57] ABSTRACT

The present invention provides a process for synthesizing a compound having the structure:

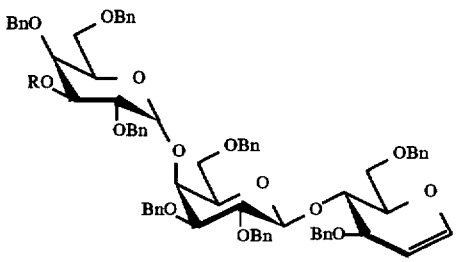

wherein R is H, as well as related oligosaccharides useful as a vaccine for inducing antibodies to human breast cancer cells in an adjuvant therapy therefor.

7 Claims, 14 Drawing Sheets

OTHER PUBLICATIONS

Lay, L., et al., "Oligosaccharides Related to Tumor–Associated Antigens", Helv. Chim. Acta (1994) 77: 509–514 (Exhibit 9).

Lay, L., et al., "Oligosaccharides Related to Tumor–Associate Antigens", Helv. Chim. Acta (1995) 78: 533–538 (Exhibit 10).

Lloyd, K.O., "Blood Group Antigens as Markers for Normal Differentiation and Malignant Change in Human Tissues" Am. J. Clin. Pathol. (1987) 87: 129–139 (Exhibit 11).

Lloyd, K.O., "Humoral immune responses to tumor–associated carbohydrate antigens", Cancer Biol. (1991) 2: 421–431 (Exhibit 12).

Lloyd, K.O., In Specifice Immunotherapy of Cancer with Vaccines; New York Academy of Sciences; New York, 1993; vol. 690; pp. 50–58 (Exhibit 13).

Menard, S., et al., "Generation of Monoclonal Antibodies Reacting with Normal and Cancer Cells of Human Breast", Cancer Res. (1983) 43: 1295–1300 (Exhibit 14).

Randolph, J.T. and Danishefsky, S.J. "An Interactive Strategy for the Assembly of Complex Branched Oligosaccharide Domains Using Solid–Support Methods: An application to a Concise Synthesis of the Lewis$^b$ Domain in Bioconjugatable Form", Angewandte Chem. Int. Ed. Eng. (1994) 33(14): 1470–1473 (Exhibit 15).

Bernstein, M.A. and Hall, L.D., A General Synthesis of Model Glycoproteins: Coupling of Alkenyl Glycosides to Proteins, Using Reductive Ozonolysis Followed By Reductive Amination With Sodium Cyanoborohydride, Carbohydrate Research (1980) 78: C1–C3.

Danishefsky, S., et al., A Strategy For the Solid–Phase Synthesis of Oligosaccharides, Science (1993) 260: 1307–1309.

Gray, G.R., "Antibodies to Carbohydrates: Preparation of Antigens By Coupling Carbohydrates to Proteins By Reductive Amination With Cyanoborohydride", Methods in Enzymology (1978) 50: 155–160.

Mahajan, R., et al., "Synthesis of Neoglycoproteins as Artificial Antigens", J. Carbohydrate Chemistry (1994) 13(1): 63–73.

20: R = Si(*i*-Pr)$_2$(S); R$^1$ = TIPS
21: R = R$^1$ = H
22: R = R$^1$ = TIPS

25: R=TIPS; R$^1$=H; R$^2$=SO$_2$Ph; R$^3$=Bn; R$^4$=C=O
26: R=R$^1$=R$^2$=R$^3$=R$^4$=Ac

17: R=CH₂CH=CH

SYNTHESIS OF THE BREAST TUMOR-ASSOCIATED ANTIGEN DEFINED BY MONOCLONAL ANTIBODY MBRL AND USES THEREOF

This application is a continuation-in-part of U.S. Ser. No. 08/213,053, filed Mar. 15, 1994, the contents of which are hereby incorporated by reference into this application.

This invention was made with government support under grants GM-15240-02, GM-16291-01, and AI-16943 from the National Institutes of Health. Accordingly, the U.S. Government has certain rights in the invention.

BACKGROUND OF THE INVENTION

Throughout this application, citations for various publications are provided within parentheses in the text. The disclosures of these publications are hereby incorporated in their entirety by reference into this application in order to more fully describe the state of the art to which this invention pertains.

The function of carbohydrates as structural materials and as energy storage units in biological systems is well recognized. By contrast, the role of carbohydrates as signaling molecules in the context of biological processes has only recently been appreciated. (M. L. Phillips, E. Nudelman, F. C. A. Gaeta, M. Perez, A. K. Singhal, S. Hakomori, J. C. Paulson, Science, 1990, 250, 1130; M. J. Polley, M. L. Phillips, E. Wagner, E. Nudelman, A. K. Singhal, S. Hakomori, J. C. Paulson, Proc. Natl. Acad. Sci. USA, 1991, 88, 6224; T. Taki, Y. Hirabayashi, H. Ishikawa, S. Kon, Y. Tanaka, M. Matsumoto, J. Biol. Chem., 1986, 261, 3075; Y. Hirabayashi, A. Hyogo, T. Nakao, K. Tsuchiya, Y. Suzuki, M. Matsumoto, K. Kon, S. Ando, ibid., 1990, 265, 8144; O. Hindsgaul, T. Norberg, J. Le Pendu, R. U. Lemieux, Carbohydr. Res., 1982, 109, 109; U. Spohr, R. U. Lemieux, ibid., 1988, 174, 211) The elucidation of the scope of carbohydrate involvement in mediating cellular interaction is an important area of inquiry in contemporary biomedical research. The carbohydrate molecules, carrying detailed structural information, tend to exist as glycoconjugates (cf. glycoproteins and glycolipids) rather than as free entities. Given the complexities often associated with isolating the conjugates in homogeneous form and the difficulties in retrieving intact carbohydrates from these naturally occurring conjugates, the applicability of synthetic approaches is apparent. (For recent reviews of glycosylation see: Paulsen, H., Agnew. Chemie Int. Ed. Engl., 1982, 21, 155; Schmidt, R. R., Angew. Chemie Int. Ed. Engl., 1986, 25, 212; Schmidt, R. R., Comprehensive Organic Synthesis, Vol. 6, Chapter 1(2), Pergamon Press, Oxford, 1991; Schmidt, R. R., Carbohydrates, Synthetic Methods and Applications in Medicinal Chemistry, Part I, Chapter 4, VCH Publishers, Weinheim, New York, 1992. For the use of glycals as glycosyl donors in glycoside synthesis, see Lemieux, R. U., Can. J. Chem., 1964, 42, 1417; Lemieux, R. U., Faser-Reid, B., Can. J. Chem., 1965, 43, 1460; Lemieux, R. U., Morgan, A. R., Can. J. Chem., 1965, 43, 2190; Thiem, J., Karl, H., Schwentner, J., Synthesis, 1978, 696; Thiem, J. Ossowski, P., Carbohydr. Chem., 1984, 3, 287; Thiem, J., Prahst, A., Wendt, T. Liebigs Ann. Chem., 1986, 1044; Thiem, J. in Trends in Synthetic Carbohydrate Chemistry, Horton, D., Hawkins, L. D., McGarvvey, G. L., eds., ACS Symposium Series #386, American Chemical Society, Washington, D.C., 1989, Chapter 8.)

The carbohydrate domains of the blood group substances contained in both glycoproteins and glycolipids are distributed in erythrocytes, epithelial cells and various secretions. The early focus on these systems centered on their central role in determining blood group specificities. (R. R. Race and R. Sanger, Blood Groups in Man, 6th ed., Blackwell, Oxford, 1975) However, it is recognized that such determinants are broadly implicated in cell adhesion and binding phenomena. (For example, see M. L. Phillips, E. Nudelman, F. C. A. Gaeta, M. Perez, A. K. Singhal, S. Hakomori, J. C. Paulson, Science, 1990, 250, 1130.) Moreover, ensembles related to the blood group substances in conjugated form are encountered as markers for the onset of various tumors. (K. O. Lloyd, Am. J. Clinical Path., 1987, 87, 129; K. O. Lloyd, Cancer Biol., 1991, 2, 421) Carbohydrate-based tumor antigenic factors might find applications at the diagnostic level, as resources in drug delivery or ideally in immunotherapy. (Toyokuni, T., Dean, B., Cai, S., Boivin, D., Hakomori, S., and Singhal, A. K., J. Am. Chem Soc., 1994, 116, 395; Dranoff, G., Jaffee, E., Lazenby, A., Golumbek, P., Levitsky, H., Brose, K., Jackson, V., Hamada, H., Paardoll, D., Mulligan, R., Proc. Natl. Acad. Sci. USA, 1993, 90, 3539; Tao, M.-H., Levy, R., Nature, 1993, 362, 755; Boon, T., Int. J. Cancer, 1993, 54, 177; Livingston, P. O., Curr. Opin. Immunol., 1992, 4, 624; Hakomori, S., Annu. Rev. Immunol., 1984, 2, 103; K. Shigeta, et al., J. Biol. Chem., 1987, 262, 1358)

The present invention provides new strategies and protocols for oligosaccharide synthesis. The object is to simplify such constructions such that relatively complex domains can be assembled with high stereo-specifity. Major advances in glycoconjugate synthesis require the attainment of a high degree of convergence and relief from the burdens associated with the manipulation of blocking groups. Another requirement is that of delivering the carbohydrate determinant with appropriate provision for conjugation to carrier proteins or lipids. (Bernstein, M. A., and Hall, L. D., Carbohydr. Res., 1980, 78, Cl; Lemieux, R. U., Chem. Soc. Rev., 1978, 7, 423; R. U. Lemieux, et al., J. Am. Chem. Soc., 1975, 97, 4076). This is a critical condition if the synthetically derived carbohydrates are to be incorporated into carriers suitable for biological application.

Antigens which are selective or ideally specific for cancer cells could prove useful in fostering active immunity. (Hakomori, S., Cancer Res., 1985, 45, 2405-2414; Feizi, T., Cancer Surveys, 1985, 4, 245-269) Novel carbohydrate patterns are often presented by transformed cells as either cell surface glycoproteins or as membrane-anchored glycolipids. In principle, well chosen synthetic glycoconjugates which stimulate antibody production could confer active immunity against cancers which present equivalent structure types on their cell surfaces. (Dennis, J., Oxford Glycosystems Glyconews Second, 1992; Lloyd, K. O., in Specific Immunotherapy of Cancer with Vaccines, 1993, New York Academy of Sciences pp. 50–58) Chances for successful therapy improve with increasing restriction of the antigen to the target cell. A glycosphingolipid was isolated by Hakomori and collaborators from the breast cancer cell line MCF-7 and immunocharacterized by monoclonal antibody MBr1. (Bremer, E. G., et al., J. Biol. Chem., 1984, 259, 14773-14777; Menard, S., et al., Cancer Res., 1983, 43, 1295-1300) The novel glycosphingolipid structure 1b (FIG. 8a) was proposed for this breast tumor-associated antigen on the basis of methylation and enzymatic degradation protocols. A $^1$H NMR spectrum consistent with but not definitive for the proposed structure was obtained from trace amounts of isolated antigen. While individual sectors of the proposed structure were not unknown, the full structure was first described based on studies on the breast cancer line. It should be noted that MBr1 also binds to normal human mammary gland tissue and ovarian cancer cell lines. Therefore, 1b as a total entity is likely not restricted to the transformed breast cells. Alternatively, smaller subsections of 1b are adequate for antibody recognition and binding. (The synthesis of the DEF fragment of 1b has been reported, and has been shown to bind to MBr1: Lay, L.; Nicotra, F.; Panza, L.; Russo, G. *Helv. Chim. Acta*, 1994, 77, 509–514.)

The compounds prepared by processes described herein are antigens useful in adjuvant therapies as a vaccines capable of inducing MBr1 antibodies immunoreactive with human breast tumor cells. Such adjuvant therapies have potential to reduce the rate of recurrence of breast cancer and increase survival rates after surgery. Clinical trials on 122 patents surgically treated for AJCC stage III melanoma who were treated with vaccines prepared from melanoma differentiation antigen GM2 (another tumor antigen which like MBr1 is a cell surface carbohydrate) demonstrated in patients lacking the antibody prior to immunization, a highly significant increase in disease-free interval (P. O. Livingston, et al., *J. Clin Oncol.*, 12, 1036 (1994)).

The present invention provides a method of synthesizing 1b in quantity as well as artificial protein-conjugates of the oligosaccharide which might be more immunogenic than the smaller glycolipid. The antigen contains a novel array of features including the α-linkage between the B and the C entities, as well as the β-linked ring D gal-NAc residue. (For the synthesis of a related structure (SSEA-3) which lacks the fucose residue see: Nunomura, S.; Ogawa, T., *Tetrahedron Lett.*, 1988, 29, 5681–5684.) The present invention provides (i) a total synthesis of 1b, (ii) rigorous proof that the Hakomori antigen does, in fact, correspond to 1b and (iii) the synthesis of a bioconjugatable version of 1b. The conciseness of the synthesis reflects the efficiency of glycal assembly methods augmented by a powerful method for sulfonamidoglycosylation (see, e.g., the transformation of 14b–15b, FIG. 10).

SUMMARY OF THE INVENTION

Figure 1:
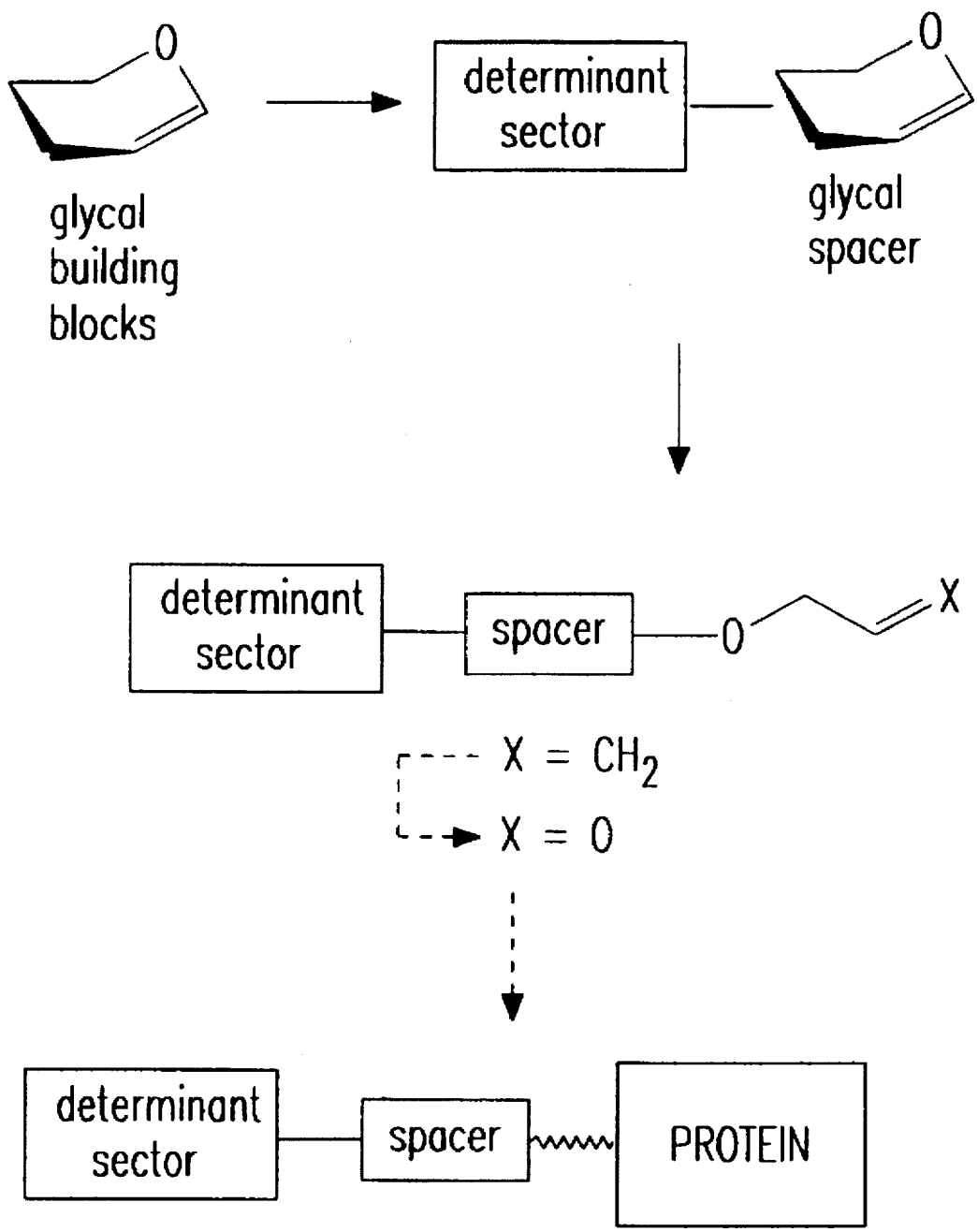
FIG. 1 shows glycal assembly leading to neoglycoproteins.

The present invention provides a process for synthesizing a compound having the structure:

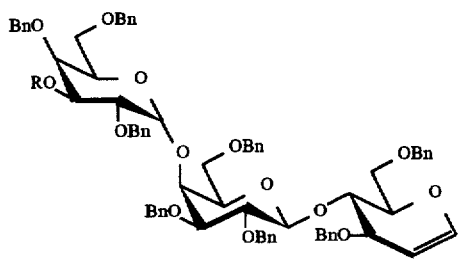

wherein R is H.

The present invention also provides a process for synthesizing a trisaccharide ceramide having the structure:

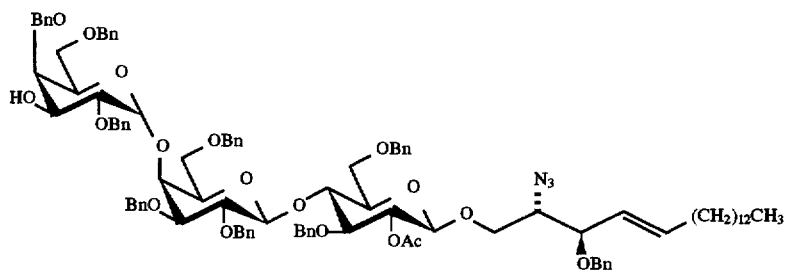

The present invention further provides a process for synthesizing a mercaptotrisaccharide having the structure:

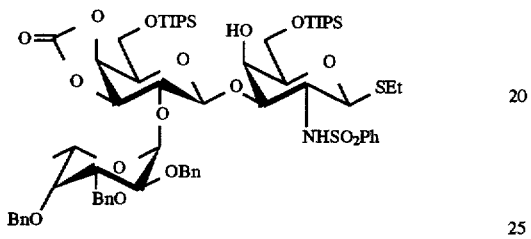

The present invention also provides a process of synthesizing a hexasaccharide ceramide having the structure:

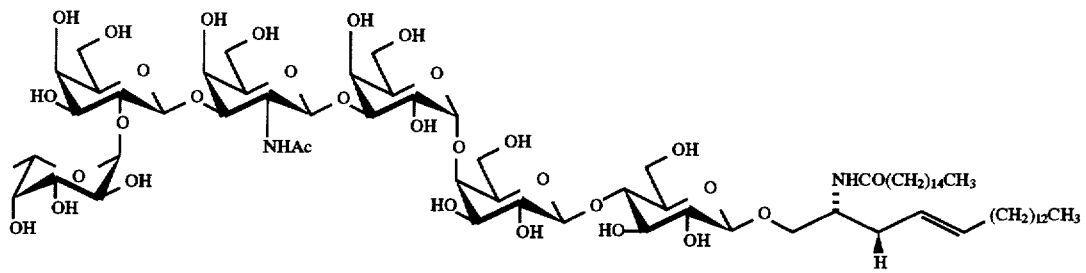

The present invention also provides a process of synthesizing a hexasaccharide ceramide having the structure:

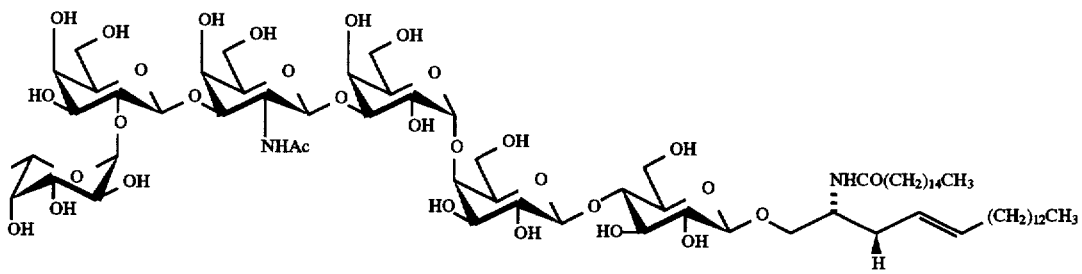

The present invention also provides a process of synthesizing an allyl hexasaccharide having the structure:

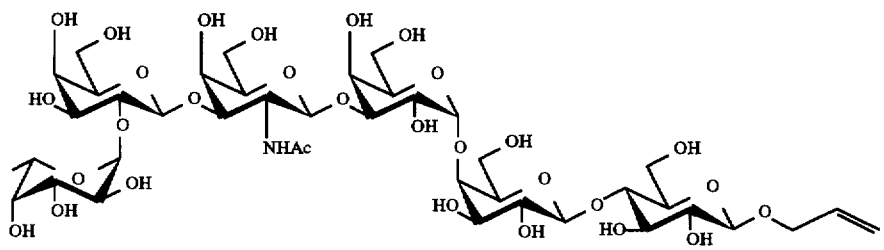

The present invention provides a process of synthesizing a hexasaccharide having the structure:

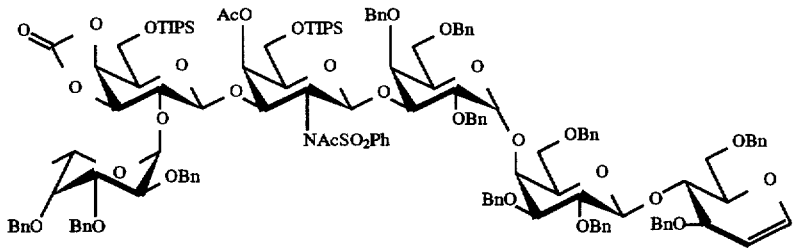

The present invention further provides a compound having the structure:

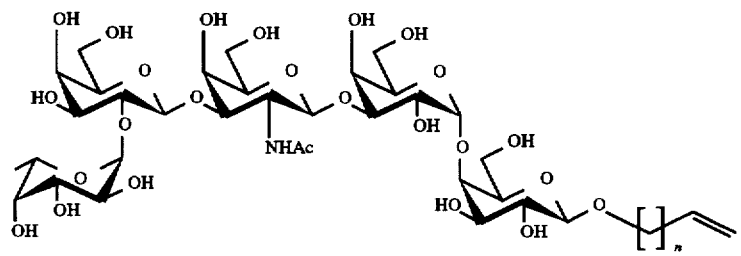

wherein n is an integer between about 0 and about 9.

The present invention also provides a compound having the structure:

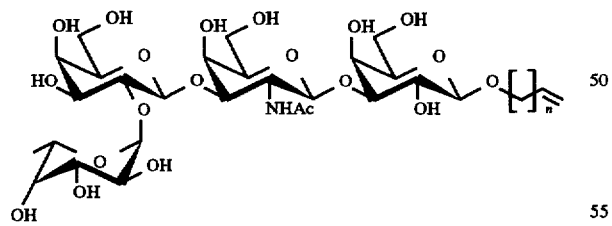

wherein n is an integer between about 0 and about 9.

The present invention also provides a compound having the structure:

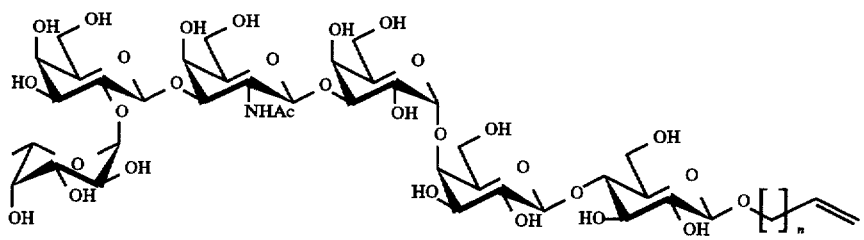

wherein n is an integer between about 0 and about 9.

DETAILED DESCRIPTION OF THE INVENTION

The present invention provides a compound having the structure:

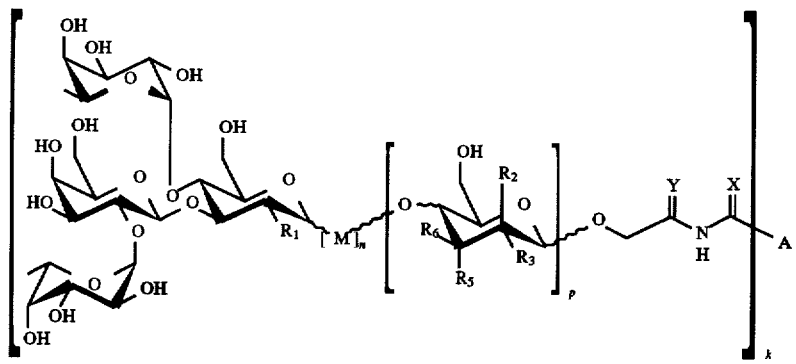

wherein A is selected from the group consisting of (i) an amino acid bearing an ω-amino group or an ω—(C=O)— group, (ii) an amino acid residue of a peptide, which residue bears an ω-amino group or an ω—(C=O)— group, and (iii) an amino acid residue of a protein, which residue bears an ω-amino group or an ω—(C=O)— group; wherein $R_1$ is H, OH, $NH_2$ or $NHR_4$, where $R_4$ is $SO_2Ph$, a linear or branched chain alkyl or acyl group, or an aryl group; wherein M has the structure:

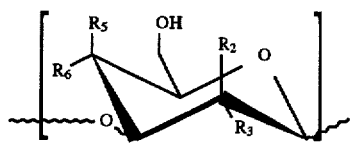

wherein n is an integer from 0 to 18, and where n is greater than 1, each M is independently the same or different; wherein p is either 0 or 1; wherein $R_2$, $R_3$, $R_5$ and $R_6$ are independently the same or different and are H or OH, with the proviso that geminal $R_2$ and $R_3$ are not both OH, and geminal $R_5$ and $R_6$ are not both OH; wherein each wavy line between a carbon atom and an oxygen atom denotes an R or S configuration at the carbon atom; wherein X and Y are independently the same or different and are $H_2$ or O; and wherein k is an integer greater than or equal to 1, with the proviso that when A is an amino acid bearing an ω-amino group or an ω—(C=O)— group, k is equal to 1.

In one embodiment, the present invention provides the compound disclosed hereinabove wherein A is lysine or a lysine residue.

In another embodiment, the present invention provides the compound disclosed hereinabove wherein A is glutamic acid or a glutamic acid residue.

In another embodiment, the present invention provides the compound disclosed hereinabove wherein A is aspartic acid or an aspartic acid residue.

The invention also provides the compound disclosed hereinabove wherein A is an amino acid residue of a globular protein. In one embodiment, the invention provides the compound wherein the globular protein is selected from the group consisting of bovine serum albumin and human serum albumin.

In one embodiment, the invention provides the compound disclosed hereinabove wherein k is 1.

In another embodiment, the invention provides the compound disclosed hereinabove wherein n and p are both equal to 0.

The invention provides a compound having the structure:

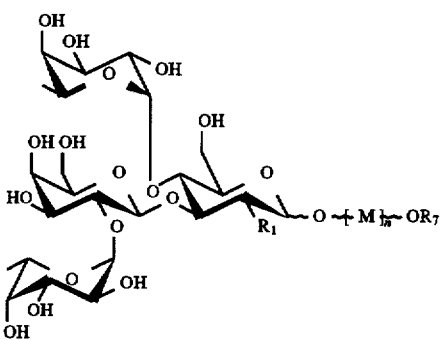

wherein $R_1$ is H, OH, $NH_2$ or $NHR_4$, where $R_4$ is $SO_2Ph$, a linear or branched chain alkyl or acyl group, or an aryl group; wherein M has the structure:

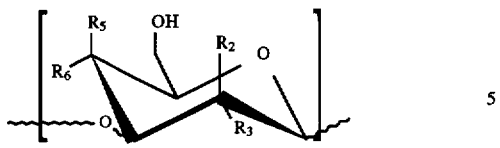

wherein n is an integer from 0 to 18, and where n is greater than 1, each M is independently the same or different; wherein $R_2$, $R_3$, $R_5$ and $R_6$ are independently the same or different and are H or OH, with the proviso that geminal $R_2$ and $R_3$ are not both OH, and geminal $R_5$ and $R_6$ are not both OH; wherein each wavy line between a carbon atom and an oxygen atom denotes an R or S configuration at the carbon atom; and wherein $R_7$ is a substituted or unsubstituted allyl group.

The invention also provides a compound having the structure:

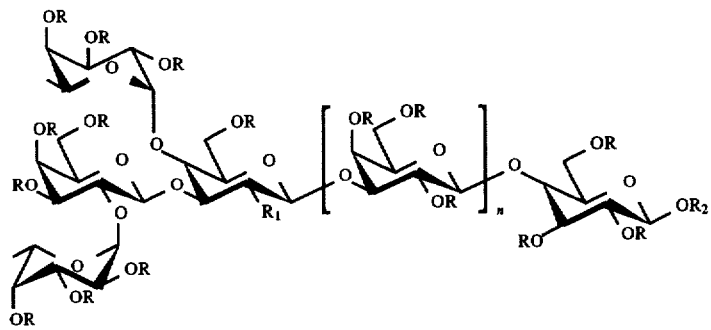

wherein n is an integer from 1 to 18; wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group. In one embodiment, the invention provides the compound wherein n is 1.

The invention further provides a compound having the structure:

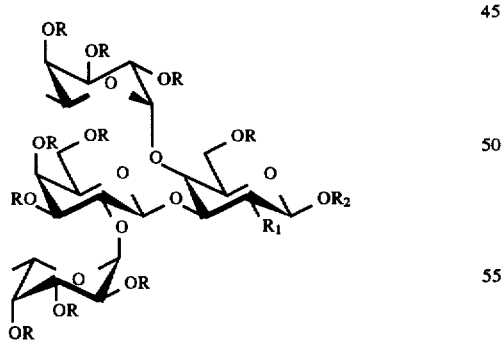

wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group.

The invention also provides a compound having the structure:

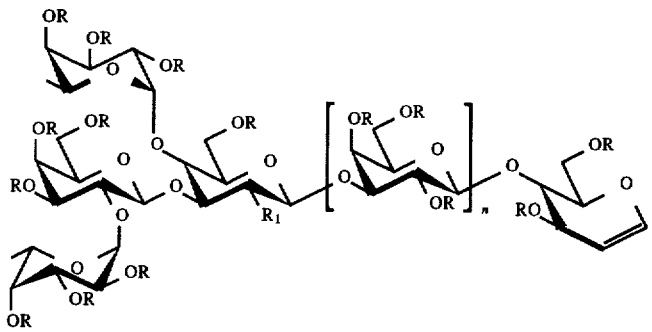

wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; wherein $R_2$ is a substituted or unsubstituted allyl group; and wherein n is an integer from 1 to 18. In one embodiment, the invention provides the compound wherein n is 1.

The invention also provides a compound having the structure:

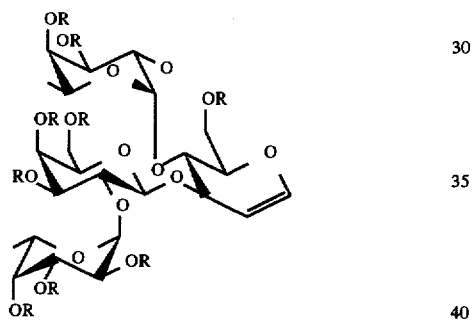

wherein R is H or a linear or branched chain acyl group.

The invention also provides a process for synthesizing a compound having the structure:

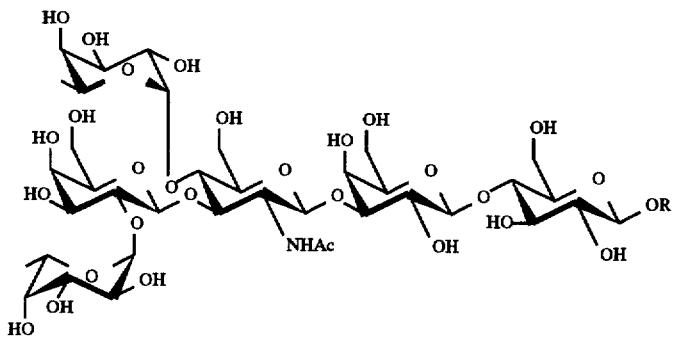

wherein R is a substituted or substituted allyl group, which comprises the steps of (a) synthesizing a compound having the structure:

15

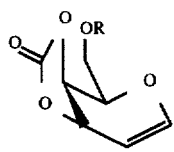

wherein R is a trialkylsilyl, aryldialkylsilyl, alkyldiarylsilyl or triaarylsilyl group; (b) reacting the compound of step (a) with a compound having structure:

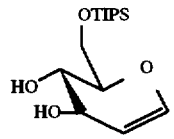

under suitable conditions to form a compound having the structure:

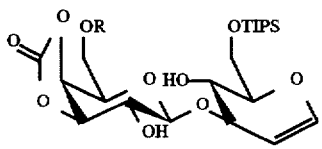

wherein R is a trialkylsilyl, aryldialkylsilyl, alkyldiarylsilyl or triaarylsilyl group; (c) reacting the compound formed in step (b) with a compound having the structure:

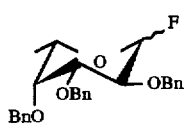

under suitable conditions to form a compound having the structure:

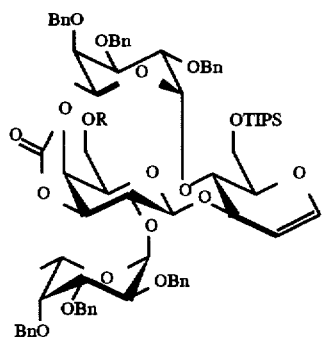

16 wherein R is a trialkylsilyl, aryldialkylsilyl, alkyldiarylsilyl or triaarylsilyl group; (d) deprotecting and re-protecting the compound formed in step (c) under suitable conditions to form a compound having the structure:

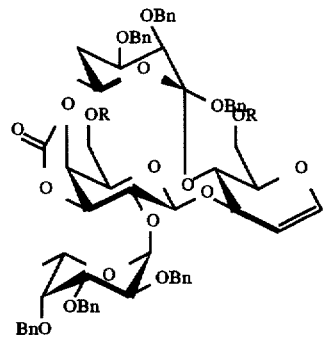

wherein R is TIPS; (e) iodosulfonamidating the compound formed in step (d) under suitable conditions to form a compound having the structure:

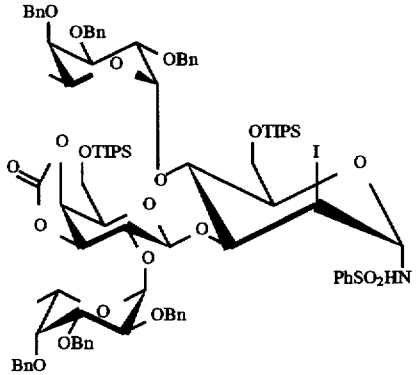

(f) reacting the compound formed in step (e) with a compound having the structure:

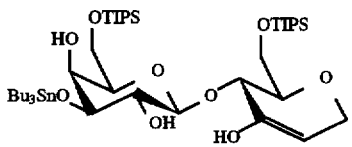

under suitable conditions to form a compound having the structure:

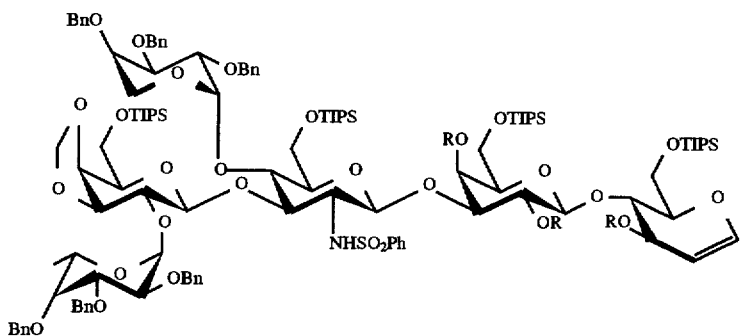

wherein R is H; (g) deprotecting and peracetylating the compound formed in step (f) under suitable conditions to form a compound having the structure:

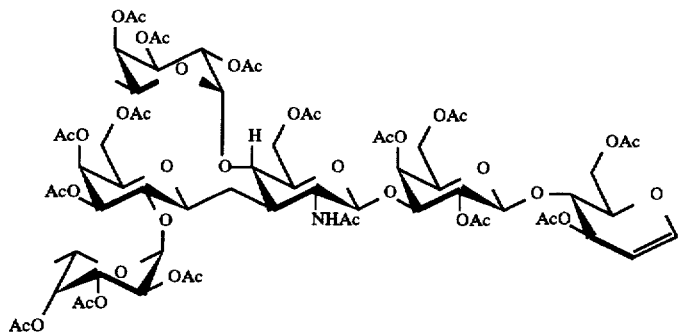

(h) epoxidizing the compound formed in step (g) under suitable conditions to form an epoxide thereof and reacting the epoxide under suitable conditions to form a compound having the structure:

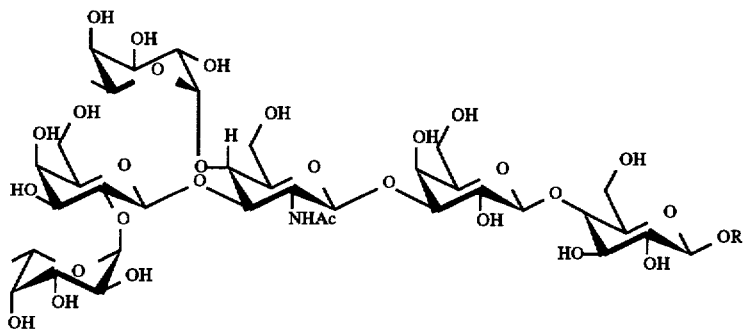

wherein R is a substituted or unsubstituted allyl group; and (i) treating the compound formed in step (h) under suitable conditions to form a compound having the structure:

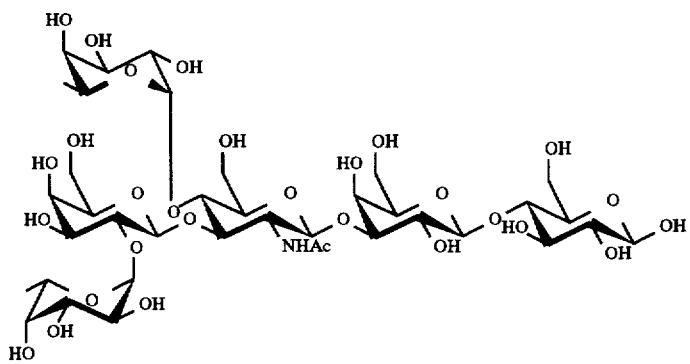

wherein R is a substituted or unsubstituted allyl group. In the above process the suitable conditions necessary for the various reactions and treatments may be found in the Experimental Details section which follows hereinafter. However, it is within the confines of the present invention that the specific reagents and solvents provided as well as the specific conditions necessary for reaction or treatment may be substituted with other suitable reactants, solvents and conditions well known to those skilled in the art.

The allyl compound may be conjugated to a peptide or protein via amine or carboxylic acid side chain. In practicing the invention, a bioconjugate is prepared according to the protocol of Bernstein and Hall (Carbohydr. Res. 1980, 78, C1). The allyl group is ozonolyzed to form either an aldehyde or carboxylic acid, which is condensed to a terminal amine to form, respectively, an imine or an amide. The imine is reduced with sodium borohydride to the amine. Alternatively, the aldehyde is reductively aminated using procedures known in the art to form an amine which is reacted with a side-chain terminal carboxylic acid to form an amide conjugate.

The invention provides a pharmaceutical composition which comprises a therapeutically effective amount of the compound disclosed hereinabove and a pharmaceutically acceptable carrier.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The invention further provides a method for treating a subject afflicted with a disorder caused by Helicobacter pylori which comprises administering to the subject a therapeutically effective amount of the pharmaceutical composition disclosed hereinabove so as to treat the subject afflicted with the disorder.

In one embodiment, the invention provides a method of treating a subject afflicted with gastric or duodenal ulcer.

In another embodiment, the invention provides a method of treating a subject afflicted with gastric adenocarcinoma.

In addition, the invention provides a method for inhibiting the adhesion of Helicobacter pylori to gastric epithelium in a subject which comprises administering to the subject an amount of the compound disclosed hereinabove effective to inhibit the adhesion of Helicobacter pylori to gastric epithelium in the subject.

The present invention also provides a process for synthesizing a compound having the structure:

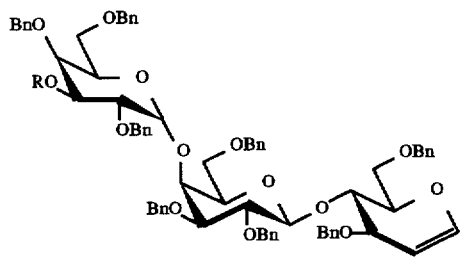

wherein R is H which comprises: (a) (i) reacting a compound having the structure:

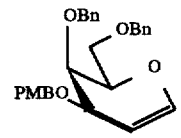

with an epoxidizing agent under suitable conditions to form an epoxide; (ii) cleaving the epoxide formed in step (a) (i) under suitable conditions with $R_4NF$ wherein each R is independently the same or different and is a linear or branched chain alkyl, aralkyl or aryl group to form a fluoroalcohol; and (iii) alkylating the fluoroalcohol formed in step (b) (ii) under suitable conditions with a non-nucleophilic base and an organic halide having the formula $C_6H_5CH_2X$ wherein X is Br, Cl, I or F to form a compound having the structure:

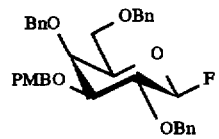

(b) (i) synthesizing a compound having the structure:

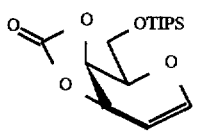

(c) (i) treating the compound formed in step (b) with an epoxidizing agent under suitable conditions to form an epoxide; and (ii) coupling the epoxide formed in step (c) (i) with a compound having the structure:

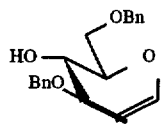

under suitable conditions to form a compound having the structure:

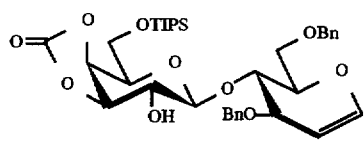

(d) (i) alkylating the compound formed in step (c) (ii) under suitable conditions with a non-nucleophilic base and an organic halide having the formula $C_6H_5CH_2X$ wherein X is Br, Cl, I or F; and (ii) de-silylating the compound formed in step (d) (i) under suitable conditions with $R_4NF$ wherein each R is independently the same or different and is a linear or branched chain alkyl, aralkyl or aryl group; (iii) treating the compound formed in step (d) (ii) under suitable conditions with a metal alkoxide to form a deprotected disaccharide; and (iv) alkylating the disaccharide formed in step (d) (iii) under suitable conditions to form a selectively deprotected disaccharide having the structure:

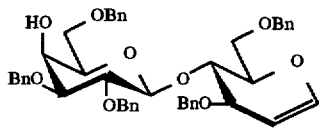

(e) (i) coupling the selectively deprotected disaccharide formed in step (d) (iv) with the compound formed in step (a) (iii) under suitable conditions to form a protected trisaccharide; and (ii) de-protecting the protected trisaccharide formed in step (e) (i) under suitable conditions to form a trisaccharide having the structure:

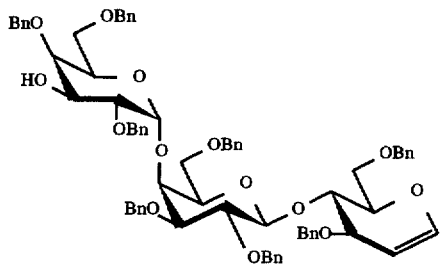

wherein R is H. In step (a) reaction (i) may be carried out using a variety of epoxidizing agents including peracetic acid, m-chlorobenzoic acid, trifluoroacetic acid, and hydrogen peroxide. A preferred agent is 3,3-dimethyldioxirane. Non-nucleophilic, inert solvents may be used, such as dichloromethane. Reaction (a) (ii) may be performed using organic ammonium fluoride salts, including tetrabutylammonium fluoride, in a range of solvents, including ethereal solvents, preferably in tetrahydrofuran. Step (iii) may be performed using a non-nucleophilic base such as sodium hydride in a non-nucleophilic solvent such as DMF. In step (b) the compound shown may be prepared as described herein. Step (c) (i) may be carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Coupling step (c) (ii) may be carried out using a metal catalyst, such as zinc chloride, in an inert solvent, such as THF. Step (d) (i) is carried out using a non-nucleophilic base such as sodium hydride in a non-nucleophilic solvent such as DMF. In step (d) (ii) de-silylation is effected using an organic ammonium fluoride salt, including tetrabutylammonium fluoride, in a range of solvents, including ethereal solvents, preferably in tetrahydrofuran. The carbonate ester is cleaved using a metal alkoxide, such as sodium methoxide, in an alcoholic medium such as methanol. Step (d) (iv) is selectively performed using a metal oxide, such as $(n-Bu_3Sn)_2O$, in the presence of an organic ammonium bromide, such as tetra-n-butylammonium bromide, in an inert solvent such as benzene. Step (e) is a coupling performed in the presence of a metal halide salt, such as $SnCl_2$, in the presence of silver perchlorate and 2,6-di-t-butylpyridine, in a solvent, such as ether, containing molecular sieves. Oxidative removal of PMB is performed with an oxidizing agent such as DDQ in an inert solvent system, which may preferably be heterogeneous, for example, using water/dichloromethane.

The present invention also provides a process for synthesizing a trisaccharide ceramide having the structure:

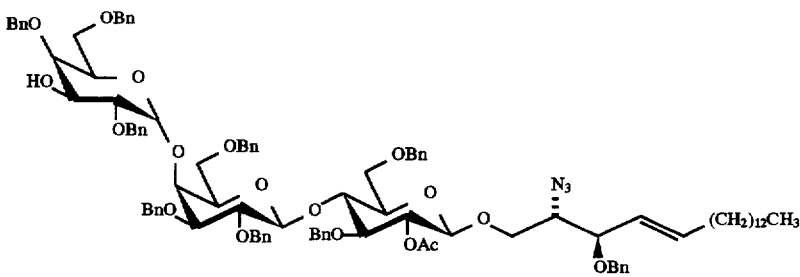

which comprises: (a) synthesizing a trisaccharide having the structure:

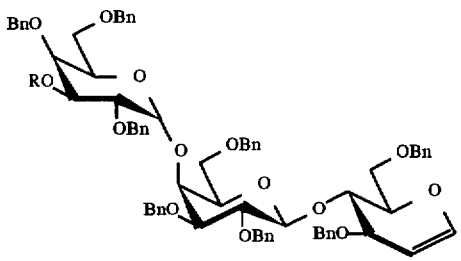

wherein R is PMB; (b) (i) reacting the trisaccharide formed in step (a) with an epoxidizing agent under suitable conditions to form a trisaccharide epoxide; and (ii) reacting the trisaccharide epoxide formed in step (b) (i) with a compound having the structure:

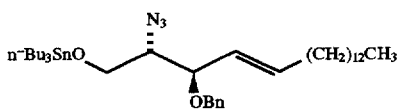

under suitable conditions to form a protected trisaccharide ceramide having the structure:

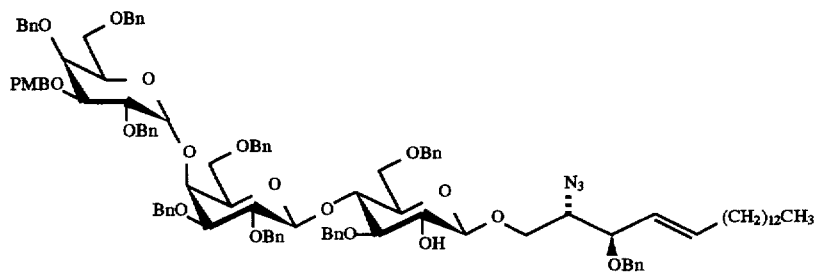

(c) (i) acylating the ceramide formed in step (b) (ii) under suitable conditions; and (ii) selectively de-protecting the compound formed in step (c) (i) under suitable conditions to form the trisaccharide ceramide.

In step (a) the trisaccharide may be synthesized as described herein. Step (b) (i) is performed using using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Coupling step (b) (ii) may be carried out using a tributyltin ether of the ceramide precursor and a metal catalyst, such as zinc chloride, in an inert solvent, such as THF. In step (c) (i) acylation is performed using a linear or branched chain alkyl anhydride preferably acetic anhydride or halide in the presence of triethylamine and DMAP in an inert organic solvent such as dichloromethane. The PMB protecting group is removed oxidatively, preferably as described above.

The present invention further provides a process for synthesizing a mercaptotrisaccharide having the structure:

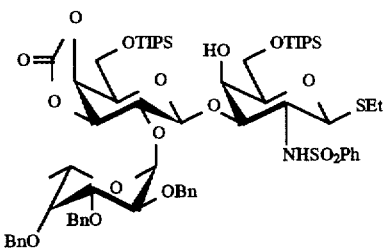

which comprises: (a) (i) synthesizing a compound having the structure:

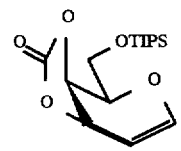

(ii) coupling the compound of step (a) (i) with a compound having structure:

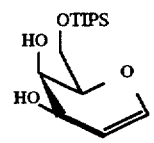

under suitable conditions to form a disaccharide having the structure:

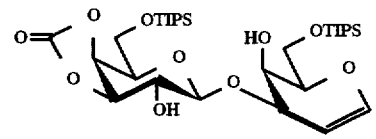

(b) coupling the disaccharide formed in step (a) (ii) with a compound having the structure:

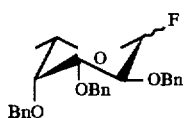

under suitable conditions to form a trisaccharide having the structure:

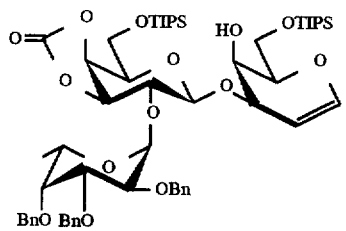

(c) iodosulfonamidating the trisaccharide formed in step (b) under suitable conditions to form a iodosulfonamide having the structure:

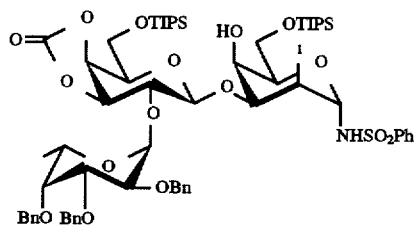

and (d) reacting the iodosulfonamide formed in step (c) under suitable conditions with a thiolate to form the mercaptotrisaccharide.

Step (a) (ii) is performed by reacting the compound of step (a) (i), which may be obtained as described herein or otherwise, with a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane, followed by coupling with the diol monosaccharide of step (a) (ii) which may be carried out using a metal catalyst, such as zinc chloride, in an inert solvent, such as THF. Coupling with the fluorosugar is carried out in step (b) in the presence of a metal halide salt, such as $SnCl_2$, in the presence of silver perchlorate and 2,6-di-t-butylpyridine, in a solvent, such as ether, containing molecular sieves. Step (c) is performed using $I(coll)_2$ perchlorate and $PhSO_2NH_2$ in the presence of molecular sieves. Step (d) is carried out using alkyl thiol and a base such as LiHMDS in an inert solvent as DMF.

The present invention also provides a process of synthesizing a hexasaccharide ceramide having the structure:

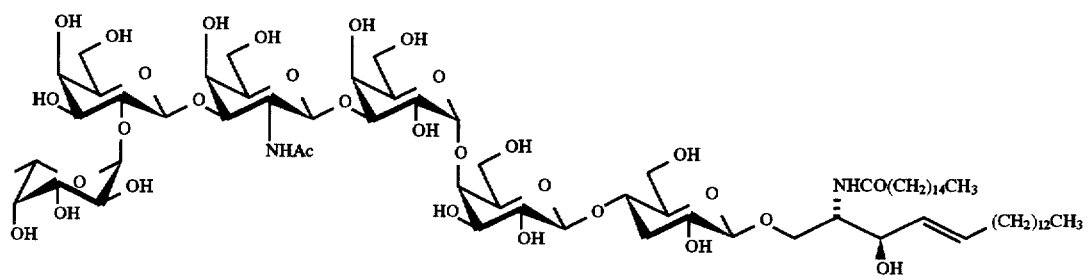

which comprises: (a) coupling a compound having the structure:

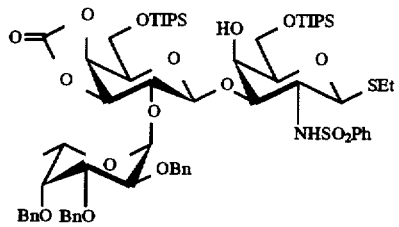

with a compound having the structure:

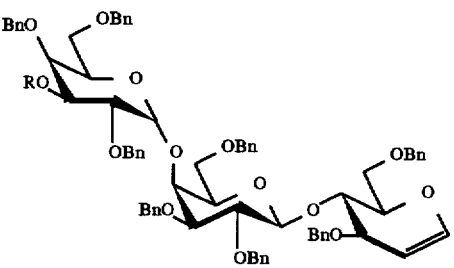

under suitable conditions to form a compound having the structure:

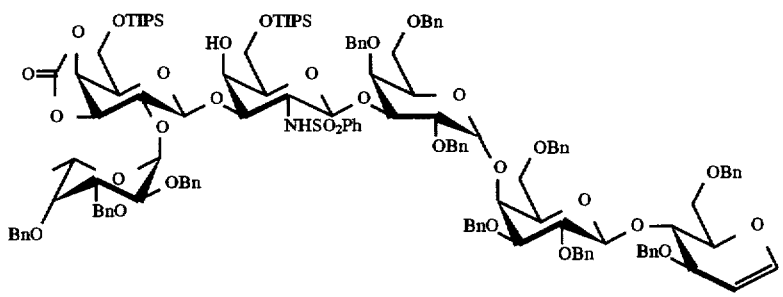

(b) (i) reacting the compound formed in step (a) with an epoxidizing agent under suitable conditions to form a hexasaccharide epoxide; and (ii) reacting the hexasaccharide epoxide with a stannyl ether having the structure:

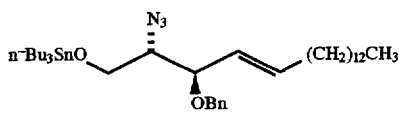

under suitable conditions to form a hexasaccharide alcohol; (c) acylating the hexasaccharide alcohol formed in step (b) (ii) under suitable conditions to form a hexasaccharide acetate having the structure:

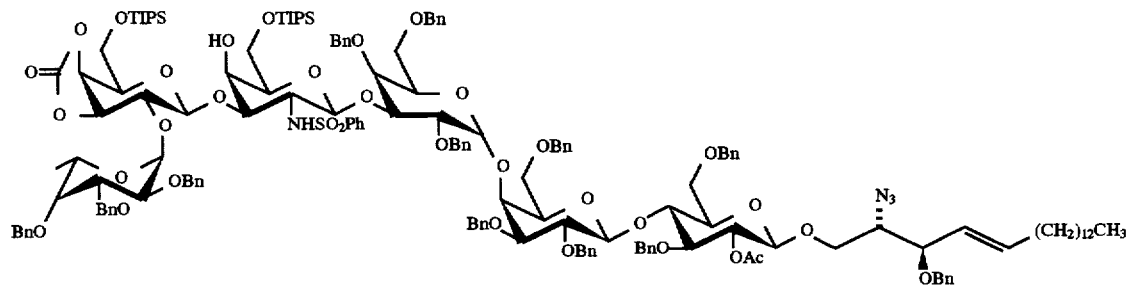

(d) reductively acylating the hexasaccharide acetate formed in step (c) under suitable conditions in the presence of palmitic anhydride to form a hexasaccharide ceramide; (e) desilylating and partially deprotecting the hexasaccharide ceramide under suitable conditions to form a partially deprotected hexasaccharide ceramide; (f) (i) reducing the partially deprotected hexasaccharide ceramide under suitable conditions to form a deprotected hexasaccharide ceramide acetate; and (ii) acylating the deprotected hexasaccharide ceramide acetate under suitable conditions to form a hexasaccharide ceramide peracetate; and (g) saponifying the hexasaccharide ceramide peracetate under suitable conditions to form the hexasaccharide ceramide.

Step (a) is performed using triflate esters, such as methyl triflate, in the presence of molecular sieves in an inert solvent. Step (b) (i) is carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Step (b) (ii) is performed using a stannyl ether of the ceramide precursor, preferably the tri-n-butyl stannylether, in the presence of a metal salt, such as Zn triflate, in an inert solvent, such as THF. Step (c) is carried out using acetic anhydride in the presence of a base such as triethylamine and DMAP. Step (d) is carried out using a noble metal catalyst such as Lindlar's catalyst and hydrogen gas in the presence of palmitic anhydride in an inert solvent such as ethyl acetate. Desilylation step (e) is effected using organic ammonium fluoride salts, such as tetra-n-butylammonium fluoride in THF. The carbonate ester is cleaved using a metal alkoxide such as NaOMe in an alcohol such as methanol. In step (f) (i) reduction is performed using a metal such as lithium or sodium in liquid ammonia and an inert solvent such as THF. Step (f) (ii) is carried out using acetic anhydride in the presence of a base such as $Et_3N$ and DMAP in an inert solvent such as dichloromethane. The peracetate is saponified using a metal alkoxide such as sodium methoxide in an alcohol such as methanol.

The present invention also provides a process of synthesizing a hexasaccharide ceramide having the structure:

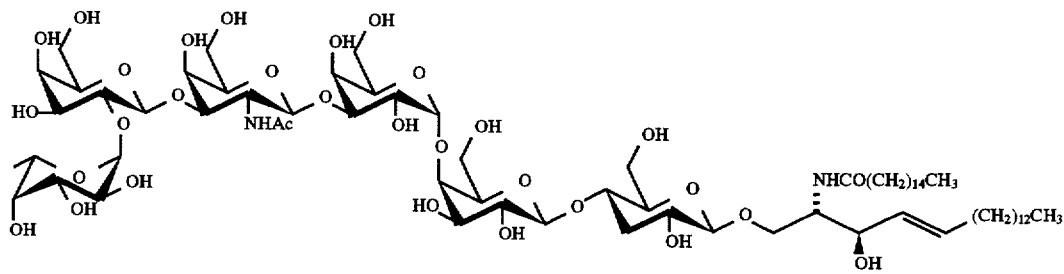

which comprises: (a) coupling a compound having the structure:

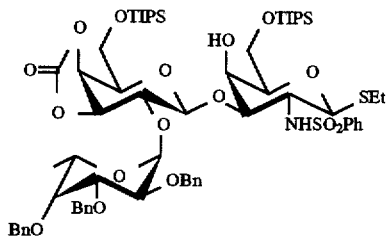

with a compound having the structure:

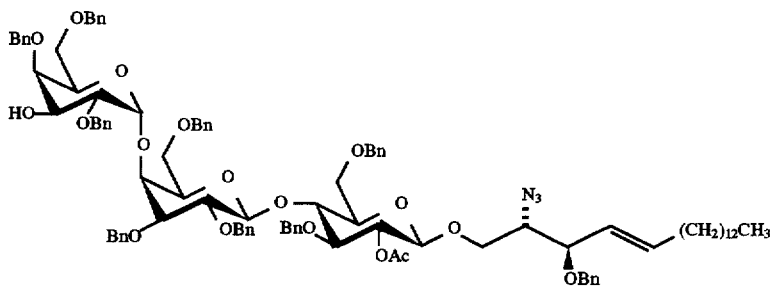

under suitable conditions to form a hexasaccharide having the structure:

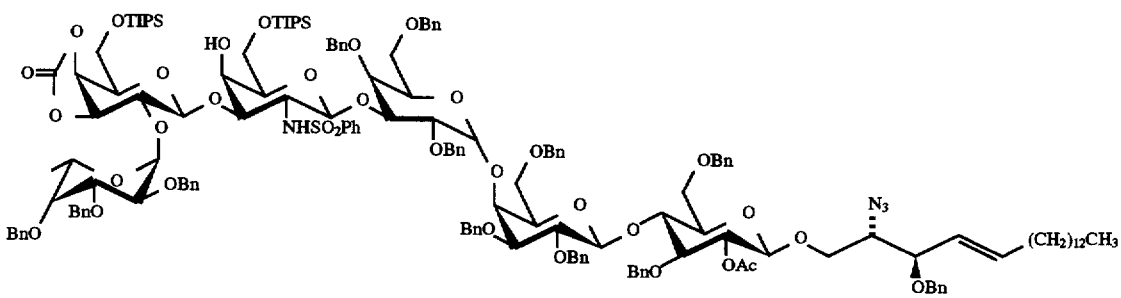

and (b) (i) reducing the hexasaccharide formed in step (a) under suitable conditions in the presence of palmitic anhydride to form a palmitoyl amide; (ii) desilylating the palmitoyl amide with $R_4NF$ wherein each R is independently the same or different and is a linear or branched chain alkyl, aralkyl or aryl group under suitable conditions to form a partially deprotected hexasaccharide; (iii) de-protecting the hexasaccharide formed in step (b) (ii) under suitable conditions to form a deprotected hexasaccharide; (iv) acylating the hexasaccharide formed in step (b) (iii) under suitable conditions to form a hexasaccharide ceramide peracetate; and (v) saponifying the hexasaccharide ceramide peracetate under suitable conditions to form the hexasaccharide ceramide.

Step (a) is performed using triflate esters, such as methyl triflate, in the presence of molecular sieves in an inert solvent. Step (b) (i) is carried out using a noble metal catalyst such as Lindlar's catalyst and hydrogen gas in the presence of palmitic anhydride in an inert solvent such as ethyl acetate. Step (b) (ii) is performed using organic ammonium fluoride salts, such as tetra-n-butylammonium fluoride in THF. In step (b) (iii) reduction is performed using a metal such as lithium or sodium in liquid ammonia and an inert solvent such as THF. Step (b) (iv) is carried out using acetic anhydride in the presence of a base such as $Et_3N$ and DMAP in an inert solvent such as dichloromethane. In step (v) the peracetate carbonate is saponified using a metal alkoxide such as sodium methoxide in an alcohol such as methanol.

The present invention also provides a process of synthesizing an allyl hexasaccharide having the structure:

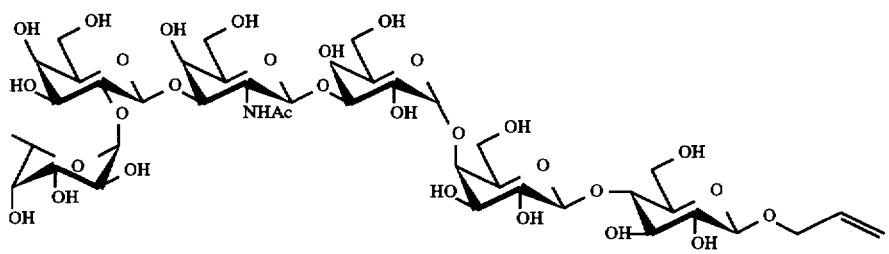

which comprises: (a) coupling a compound having the structure:

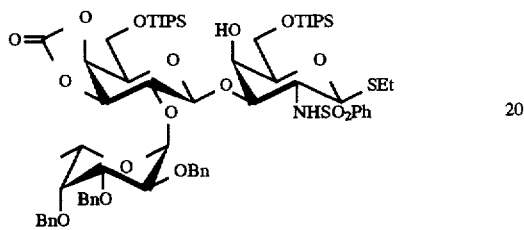

with a compound having the structure:

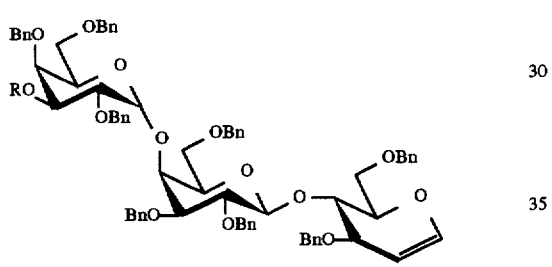

wherein R is H under suitable conditions to form a hexasaccharide having the structure:

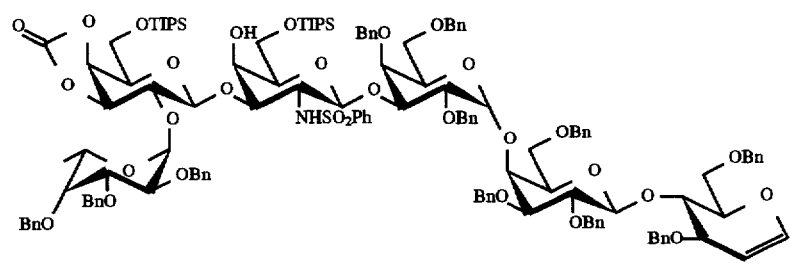

(b) (i) desilylating the compound formed in step (a) with R₄NF wherein each R is independently the same or different and is a linear or branched chain alkyl, aralkyl or aryl group under suitable conditions to form a partially deprotected hexasaccharide; (ii) de-protecting the hexasaccharide formed in step (b) (i) under suitable conditions to form a deprotected hexasaccharide; and (iii) peracylating the compound formed in step (b) (ii) under suitable conditions to form a hexasaccharide peracetate having the structure:

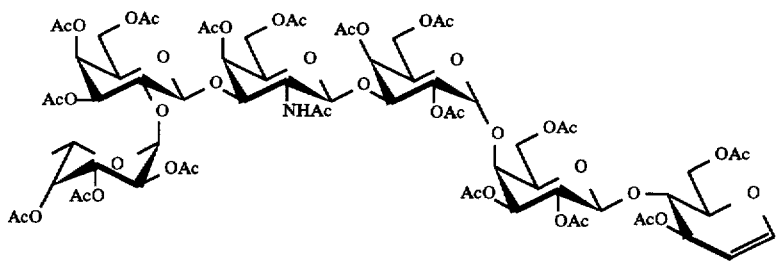

(c) (i) reacting the hexasaccharide peracetate formed in step (b) (iii) with an epoxidizing agent under suitable conditions to form an hexasaccharide epoxide peracetate; (ii) treating the hexasaccharide epoxide peracetate formed in step (c) (i) with allyl alcohol under suitable conditions to form an allyl hexasaccharide peracetate; and (iii) saponifying the allyl hexasaccharide peracetate under suitable conditions to form the allyl hexasaccharide.

Step (a) is performed using triflate esters, such as methyl triflate, in the presence of molecular sieves in an inert solvent. Step (b) (i) is carried out using organic ammonium fluoride salts, such as tetra-n-butylammonium fluoride in THF. Step (b) (ii) is performed using a metal alkoxide such as sodium methoxide in an alcohol such as methanol, followed by reduction performed using a metal such as lithium or preferably sodium in liquid ammonia and an inert solvent such as THF. Step (b) (iii) is carried out using acetic anhydride in the presence of a base such as $Et_3N$ and DMAP in an inert solvent such as dichloromethane. In step (c) (i) is carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Step (c) (ii) is carried out using allyl alcohol in an inert solvent. Step (c) (iii) the peracetate carbonate is saponified using a metal alkoxide such as sodium methoxide in an alcohol such as methanol.

The present invention provides a process of synthesizing a hexasaccharide having the structure:

which comprises: (a) coupling a compound having the structure:

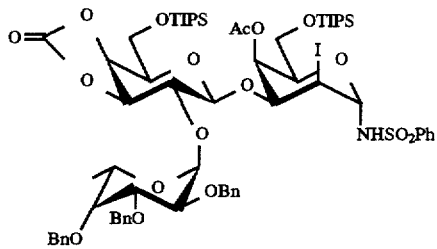

with a compound having the structure:

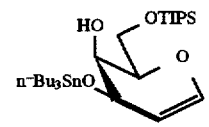

under suitable conditions to form a compound having the structure:

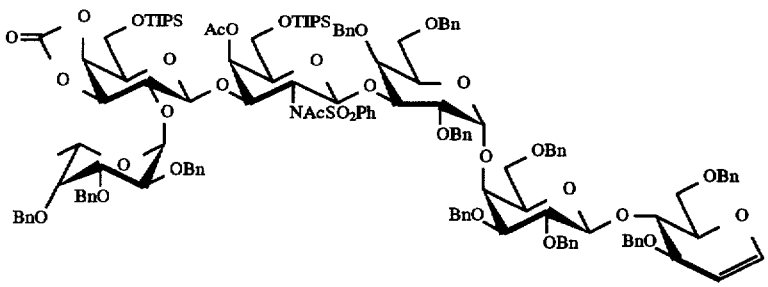

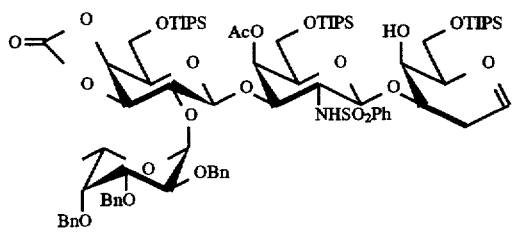

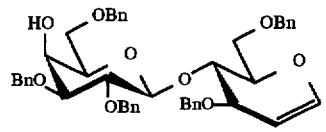

under suitable conditions to form the hexasaccharide.

(b) (i) acylating the compound formed in step (a) under suitable conditions; and (ii) reacting the compound formed in step (b) (i) with an epoxidizing agent under suitable conditions to form an epoxide having the structure:

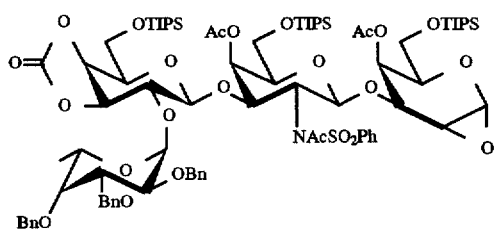

(c) (i) treating the epoxide with R₄NF wherein each R is independently the same or different and is a linear or branched chain alkyl, aralkyl or aryl group under suitable conditions; and (ii) alkylating the compound formed in step (c) (i) under suitable conditions to form a compound having the structure:

Step (a) is performed using a metal catalyst such as silver tetrafluoroborate in an inert solvent. Step (b) (i) is carried out using acetic anhydride in the presence of a base such as Et₃N and DMAP in an inert solvent such as dichloromethane. Step (b) (ii) is carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Step (c) (i) is effected with organic ammonium fluoride salts, such as tetra-n-butylammonium fluoride in THF. Step (c) (ii) is performed using a non-nucleophilic base such as sodium hydride in an inert solve. Step (d) is performed using a metal salt catalyst such as tin dichloride in the presence of silver perchlorate in an inert solvent such as di-t-butylpyridine. Further transformations provide deprotected products or conjugates with proteins or other carriers.

The present invention further provides a compound having the structure:

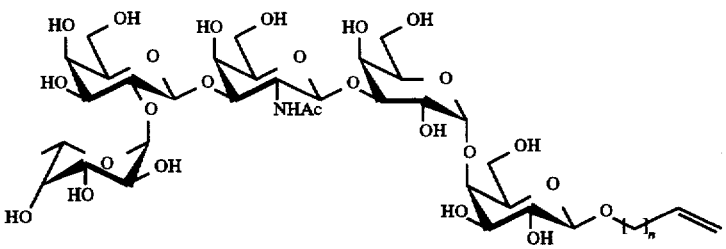

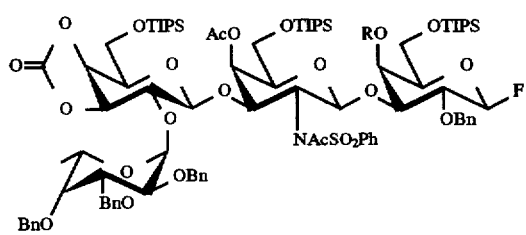

wherein R is H or acyl; (d) coupling the compound formed in step (c) (ii) with a compound having the structure:

wherein n is an integer between about 0 and about 9. The allyl glycoside shown is prepared using the glycal coupling methods taught herein, and may be bound to protein carriers using general reactions described herein or by standard methods in the art. For example, the allyl glycoside may be prepared by coupling compound 9b disclosed herein with a suitably protected 8b, followed by coupling with 12b, then coupling with allyl alcohol and an appropriate deprotection sequence.

The present invention also provides a compound having the structure:

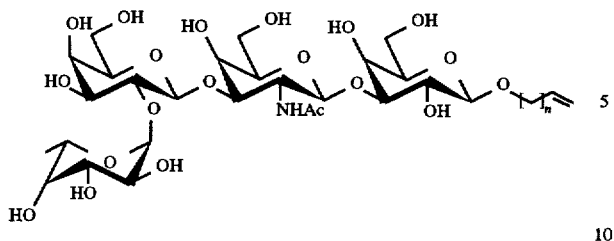

wherein n is an integer between about 0 and about 9.

Figure 12:
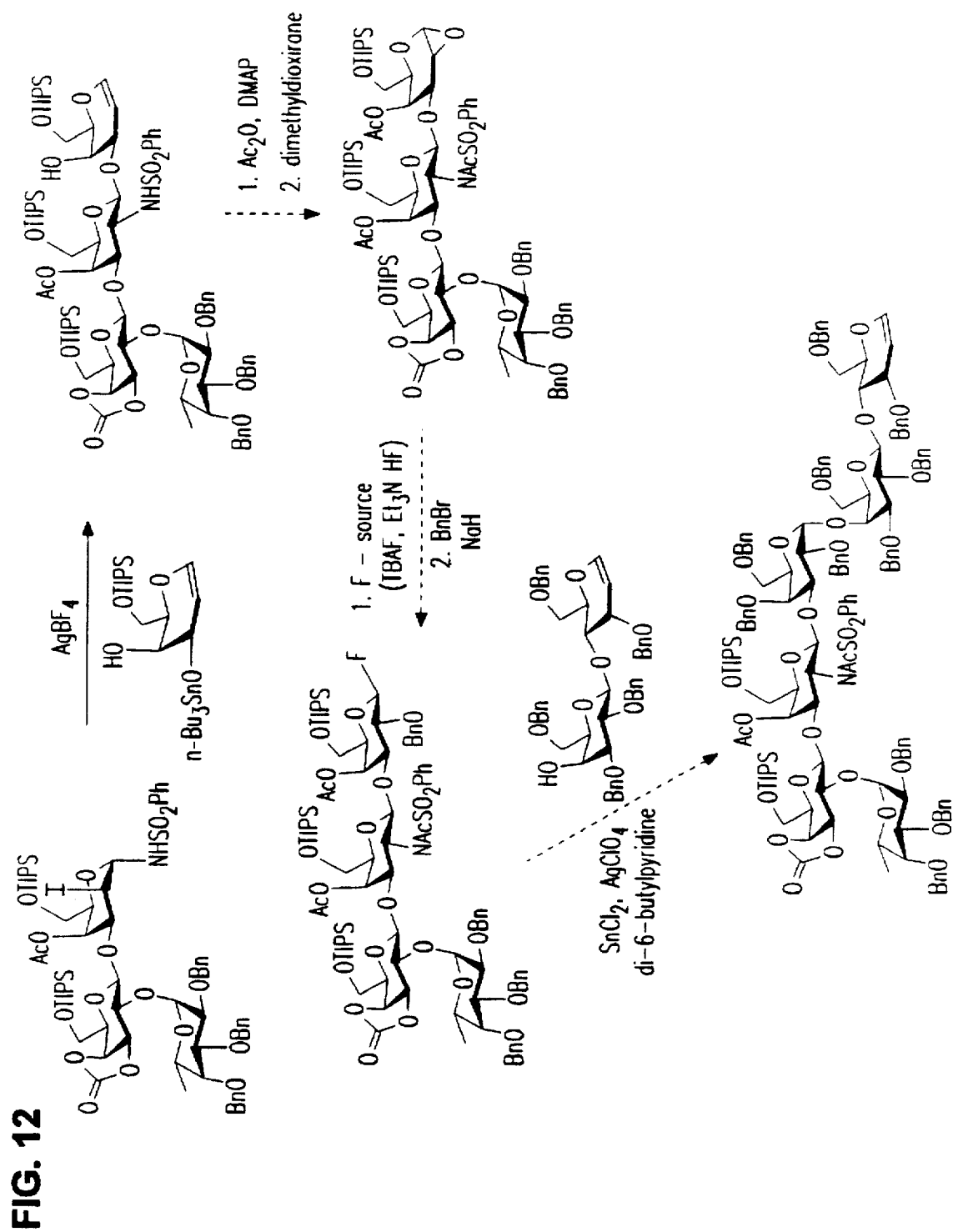
FIG. 12 shows a reaction pathway to the hexasaccharide antigen MBr1 by a 4+2 synthetic approach.

The allyl glycoside shown is prepared using the glycal coupling methods, allylation and a deprotection sequence as taught herein (see FIG. 12), and may be bound to protein carriers using general reactions described herein or by standard methods in the art.

The present invention also provides a compound having the structure:

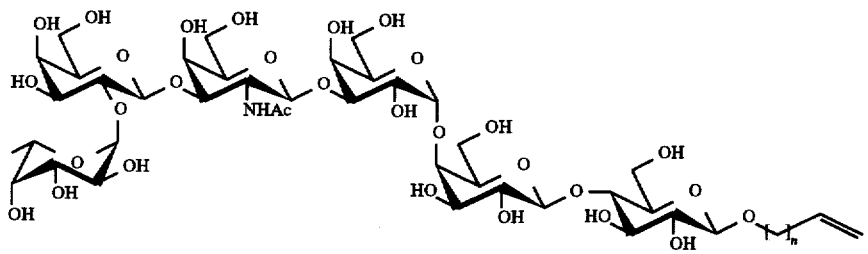

wherein n is an integer between about 0 and about 9.

The allyl glycosides shown are prepared using the glycal coupling methods taught herein, and may be bound to protein carriers using general reactions described herein or by standard methods in the art.

It is within the scope of the present invention to vary the combination of protecting groups for the various sugar hydroxyl groups in accord with ordinary skill in the art.

The present invention provides a method of inducing antibodies in a human subject, wherein the antibodies are immunoreactive with human breast tumor cells, which comprises administering to the subject an amount of a compound having the structure:

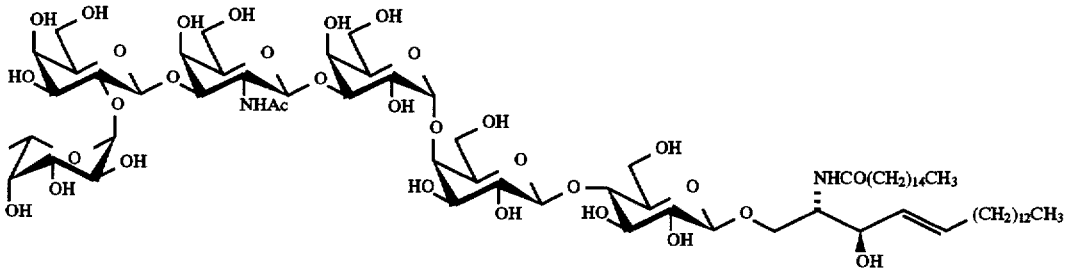

alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or lipo somes. In yet another embodiment, the present invention provides wherein the adjuvant is bacille Calmette-Guerin (BCG).

The present invention provides a method of preventing recurrence of breast cancer in a subject which comprises vaccinating the subject with the compound shown hereinabove either alone or bound to a suitable immunological carrier, adjuvant or vehicle.

The present invention also provides a method of inducing antibodies in a subject, wherein the antibodies are immunoreactive with human breast tumor cells, which comprises administering to the subject an amount of the compound having the structure:

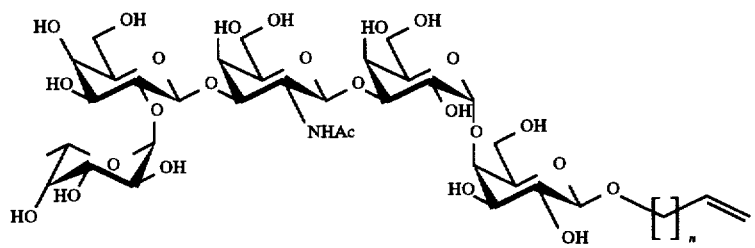

wherein n is an integer between about 0 and about 9 either alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin.

The present invention provides a method of preventing recurrence of breast cancer in a subject which comprises vaccinating the subject with the compound shown hereinabove either alone or bound to a suitable immunological carrier, adjuvant or vehicle.

The present invention also provides a method of inducing antibodies in a subject, wherein the antibodies are immunoreactive with human breast tumor cells, which comprises administering to the subject an amount of the compound having the structure:

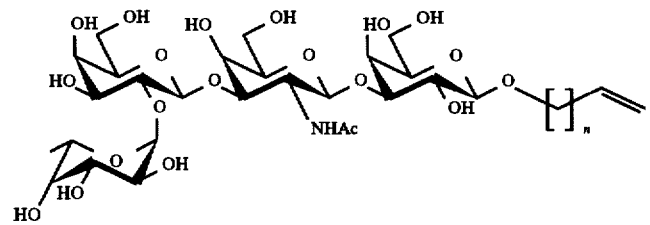

wherein n is an integer between about 0 and about 9 either alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin.

The present invention also provides a method of preventing recurrence of breast cancer in a subject which comprises vaccinating the subject with the compound shown hereinabove either alone or bound to a suitable immunological carrier, adjuvant or vehicle.

The present invention additionally provides a method of inducing antibodies in a subject, wherein the antibodies are immunoreactive with human breast tumor cells, which comprises administering to the subject an amount of the compound having the structure:

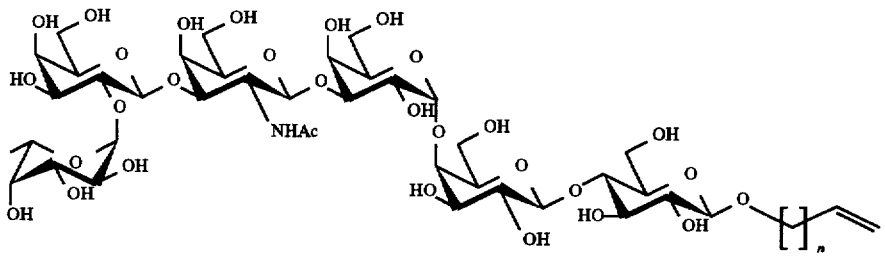

wherein n is an integer between about 0 and about 9 either alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin.

The present invention also provides a method of preventing recurrence of breast cancer in a subject which comprises vaccinating the subject with the compound shown hereinabove either alone or bound to a suitable immunological carrier, adjuvant or vehicle.

Experimental Details

General Procedures

All air- and moisture-sensitive reactions were performed in a flame-dried apparatus under an argon atmosphere unless otherwise noted. Air-sensitive liquids and solutions were transferred via syringe or canula. Wherever possible, reactions were monitored by thin-layer chromatography (TLC). Gross solvent removal was performed in vacuum under aspirator vacuum on a Buchi rotary evaporator, and trace solvent was removed on a high vacuum pump at 0.1–0.5 mmHg. Melting points (mp) were uncorrected and performed in soft glass capillary tubes using an Electrothermal series IA9100 digital melting point apparatus.

Infrared spectra (IR) were recorded using a Perkin-Elmer 1600 series Fourier-Transform instrument. Samples were prepared as neat films on NaCl plates unless otherwise noted. Absorption bands are reported in wavenumbers (cm$^{-1}$). Only relevant, assignable bands are reported.

Proton nuclear magnetic resonance ($^1$H NMR) spectra were determined using a Bruker AMX-400 spectrometer at 400 MHz. Chemical shifts are reported in parts per million (ppm) downfield from tetramethylsilane (TMS; $\delta$=0 ppm) using residual CHCl$_3$ as a lock reference ($\delta$=7.25 ppm). Multiplicities are abbreviated in the usual fashion: s=singlet; d=doublet; t=triplet; q=quartet; m=multiplet; br=broad.

Carbon nuclear magnetic resonance ($^{13}$C NMR) spectra were performed on a Bruker AMX-400 spectrometer at 100 MHz with composite pulse decoupling. Samples were prepared as with $^1$H NMR spectra, and chemical shifts are reported relative to TMS (0 ppm); residual CHCl$_3$ was used as an internal reference ($\delta$=77.0 ppm).

All high resolution mass spectral (HRMS) analyses were determined by electron impact ionization (EI) on a JEOL JMS-DX 303HF mass spectrometer with perfluorokerosene (PFK) as an internal standard. Low resolution mass spectra (MS) were determined by either electron impact ionization (EI) or chemical ionization (CI) using the indicated carrier gas (ammonia or methane) on a Delsi-Nermag R-10-10 mass spectrometer. For gas chromatography/mass spectra (GCMS), a DB-5 fused capillary column (30 m, 0.25 mm thickness) was used with helium as the carrier gas. Typical conditions used a temperature program from 60°–250° C. at 40° C./min.

Thin layer chromatography (TLC) was performed using precoated glass plates (silica gel 60, 0.25 mm thickness). Visualization was done by illumination with a 254 nm UV lamp, or by immersion in anisaldehyde stain (9.2 mL p-anisaldehyde in 3.5 mL acetic acid, 12.5 mL conc. sulfuric acid and 338 mL 95% ethanol (EtOH)) and heating to colorization.

Flash silica gel chromatography was carried out according to the standard protocol.

Unless otherwise noted, all solvents and reagents were commercial grade and were used as received, except as indicated hereinbelow, where solvents were distilled under argon using the drying methods listed in paretheses: CH$_2$Cl$_2$ (CaH$_2$); benzene (CaH$_2$); THF (Na/ketyl); Et$_2$O (Na/ketyl); diisopropylamine (CaH$_2$).

| Abbreviations | |
|---|---|
| OTf | triflate |
| TLC | thin layer chromatography |
| EtOAc | ethyl acetate |
| TIPS | triisopropylsilyl |
| PMB | p-methoxybenzyl |
| Bn | benzyl |
| Ac | acetate |
| hex | hexane |
| THF | tetrahydrofuran |
| coll | collidine |
| LiHMDS | lithium hexamethyldisilazide |
| DMF | N,N-dimethylformamide |
| DMAP | 2-dimethylaminopyridine |
| DDQ | 2,3-dichloro-5,6-dicyano-1,4-benzoquinone |
| TBAF | tetra-n-butylammonium fluoride |
| M.S. | molecular sieves |

| Abbreviations | |
|---|---|
| r.t. | room temperature |
| r.b. | round bottom flask |

EXAMPLE 1

Preparation of Polymer-Bound Glucal 18

Polymer-bound galactal 7 (500 mg; S. J. Danishefsky, et al., *J. Am. Chem. Soc.* 1992, 8331) was placed in a 100 mL polymer flask and dried in vacuo. On cooling to 0° C. under $N_2$, dry $CH_2Cl_2$ (20 mL) and freshly prepared Murray solution (30 mL; R. W. Murray and R. Jeyaraman, J. Org Chem. 1985, 2847) was added. After stirring at 0° C. for ~90 min., solubles were filtered using $N_2$ pressure. The oxidation procedure was repeated. The resulting epoxide of 7 kept on a vacuum line for ~3 h to dry. A solution of glucal 19 (1.0 g in 8 mL dry THF) was added, and the mixture was cooled to −23° C. (dry ice-$CCl_4$). A solution of $ZnCl_2$ in THF (0.8 mL 1.0M) was added. The mixture was slowly allowed to warm to r.t. (over ~2 h), and then stirred at r.t. overnight. The polymer-bound glucal 18 was rinsed with 3×20 mL THF, and dried on a vacuum line.

Preparation of Polymer-Bound Tetrasaccharide 20

Polymer-bound glucal 18 and $Sn(OTf)_2$ (0.80 g, 1.92 mmol) were combined and dried in vacuo. On cooling to 0° C. under $N_2$, a solution of fucosyl donor 10 (1.8 g, 4.1 mmol) in 20 mL dry THF with di-t-butylpyridine (1.7 mL, 7.57 mmol) was added. The mixture was allowed to warm slowly to r.t., and stirred overnight. The polymer was washed with 2×20 mL dry THF, 2×20 mL dry dioxane, 20 mL DMSO, and 2×20 mL THF. The resulting polymer-bound tetrasaccharide 20 was kept on a vacuum line to dry.

Preparation of Tetrasaccharide Glycal 21

The polymer-bound tetrasaccharide 20 (50 mg) was stirred in 2 mL THF, and treated with 0.2 mL each of 1.0M solutions of TBAF and AcOH in THF. The mixture was stirred at 40° C. overnight. The polymer was washed with 3×5 mL THF. The combined rinsings were concentrated and column-chromatographed on silica (2:1 EtOAc:hex), providing tetrasaccharide glycal 21 as a colorless gum.

Yield: 9.0 mg.

EXAMPLE 2

Preparation of Diol 18'

Galactal 7' (0.100 g, 0.304 mmol) in 5 mL dry $CH_2Cl_2$ at 0° C. under a $N_2$ atmosphere was treated with 10 mL Murray solution (freshly prepared) and stirred at 0° C. for 40 min. TLC (1:1 EtOAc:hex) showed no trace of 7'. Solvents were evaporated using a dry $N_2$ stream. The residual epoxide of 7' was kept on a vac. line ~2 h. To the epoxide under a $N_2$ atmosphere was added a solution of glucal derivative 3' (0.150 g, 0.496 mmol) in 3 mL dry THF. On cooling to −78° C., 1.0M $ZnCl_2$ in $Et_2O$ (0.50 mL, 0.50 mmol) was added. The mixture was allowed to slowly warm to r.t. (over ~2 h) and stirred overnight. TLC (1:1 EtOAc:hex) showed that the reaction was complete. Saturated aq. $NaHCO_3$ (20 mL) was added, and the mixture was then extracted with EtOAc (3×20 mL). The organic layer was dried over $MgSO_4$. Column chromatography on silica (1:3 EtOAc:hex) afforded diol 18' as a colorless solid. Yield: 173 mg (89%). $[\alpha]_D^{23}$ −9.8° (c 1.0, $CH_2Cl_2$).

Preparation of Tetrasaccharide 22

Diol 18' (86 mg, 0.133 mmol) and fucosyl donor 10 (0.290 g, 0.665 mmol) were azeotropically dried using benzene. The mixture was dissolved in 3 mL dry THF together with 0.65 mL di-t-butylpyridine and then added via canula to a flask containing $Sn(OTf)_2$ (0.30 g, 0.72 mmol) and 4 Å MS (500 mg) at 0° C. under $N_2$ atm. The mixture was stirred at 0° C., ~7 h. TLC (1:3 EtOAc:hex) shows no trace of diol 18'. The mixture was partitioned between saturated aq. $NaHCO_3$ (100 mL) and EtOAc (2×100 mL). The organic layer was dried over $MgSO_4$. The organic layer was filtered through silica using EtOAc to obtain crude material, which was then purified by chromatography on silica (1:9 EtOAc:hex) affording tetrasaccharide 22. Yield: 170 mg (86%).

Preparation of Iodosulfonamide 23

Procedure 1

Tetrasaccharide glycal 22 (120 mg, 81.1 mmol) and $PhSO_2NH_2$ (20 mg, 0.13 mmol) were azeotropically dried using benzene. Added (glove bag) 4 Å MS (0.2 g). After cooling to 0° C. under $N_2$, dry $CH_2Cl_2$ (1.0 mL) was added. The mixture was treated with a solution of $I(coll)_2ClO_4$ (prepared from 100 mg $Ag(coll)_2ClO_4$, 5 mL collidine, and 60 mg $I_2$ in 1 mL dry $CH_2Cl_2$) via canula through a plug of flame-dried celite and 4 Å MS. The mixture was stirred at 0° C. for 40 min. TLC (1:4 EtOAc:hex) showed iodosulfonamide 23 as the major component. The mixture was filtered through celite, which was rinsed with $Et_2O$. The organic layer was extracted with saturated aq. $Na_2S_2O_3$, saturated aq. $CuSO_4$, brine, and then dried over $MgSo_4$. Column chromatography on silica (1:4 EtOAc:hex) gave iodosulfonamide 23 as a colorless solid.

Yield: 115 mg (80%).

Procedure 2

Tetrasaccharide glycal 22 (200 mg, 0.135 mmol), $PhSO_2NH_2$ (42 mg, 0.27 mmol), and 200 mg powdered 4 Å MS in 2.0 mL dry $CH_2Cl_2$ at 0° C. under a $N_2$ atmosphere was treated with $I(coll)_2ClO_4$ (prepared from 120 mg $Ag(coll)_2ClO_4$ and 67 mg $I_2$ in 1 mL dry $CH_2Cl_2$). The mixture was stirred at 0° C. (protected from light using foil) for 30 min. TLC (1:2 EtOAc:hex) showed mainly iodosulfonamide with some glycal.

After ~1 h more at 0° C., TLC showed no noticeable improvement. The mixture was filtered through celite, which was washed with $Et_2O$. After extracting with saturated aq. $Na_2S_2O_3$, saturated aq. $CuSO_4$, brine, the organics were dried over $MgSO_4$. Column chromatography on silica (1:3 EtOAc:hex) gave 23 as a colorless solid.

Yield: 165 mg (69%). $[\alpha]_D^{23}$=−85.7° (c 1.0, $CH_2Cl_2$).

Preparation of Hexasaccharide 25

Iodosulfonamide 23 (60 mg, 34 mmol) in a 35 mL r.b. was treated with 200 mg powdered 4 Å MS (glove bag). To this flask under $N_2$ was added a solution of protected lactal 24 in THF (1.5 mL). On cooling the mixture to −78° C., a solution of $AgBF_4$ (40 mg, 0.206 mmol) was added in 0.25 mL dry THF. The mixture was stirred and slowly warmed to r.t. overnight. The mixture was warmed to 45° C. and stirred ~36 h. TLC showed only a trace of iodosulfonamide. Saturated aq. $NH_4Cl$ (5 mL) was added, and the mixture was extracted with 3×10 mL EtOAc. The organic layer was dried over $MgSO_4$. Column chromatography on silica (1:3 EtOAc:hex) afforded 25 as a colorless oil. Yield: 42 mg (55%).

$[\alpha]_D^{23}$=−33.8° (c 2.0, $CH_2Cl_2$)

Preparation of Hexasaccharide 25a

Hexasaccharide 25 (55 mg, 24.4 mmol) in ~1.5 mL THF was treated at 0° C. with TBAF (0.25 mL, 1.0M solution in THF, 0.25 mmol), and stirred at r.t. overnight. TLC (1:9 MeOH:$CH_2Cl_2$) showed a 3:1 mixture of 25a vs. a less polar substance. Additional 1.0M TBAF (0.10 mL) was added, and the mixture was stirred overnight at r.t. TLC showed that the reaction was complete. Solvents were removed using a N$_2$ stream. Column chromatography on silica (1:19 MeOH:CH$_2$Cl$_2$) afforded a ~1:2 mixture corresponding to two compounds which differ only in the presence or absence of a 3,4-cyclic carbonate group. Crude yield: 35 mg total weight for two products. The crude mixture was used as such for the next reaction.

Preparation of Peracetylated Hexasaccharide 26

Hexasaccharide 25a (36 mg) in 0.25 mL dry THF was added via canula to ~8 mL bright blue Na/NH$_3$ solution at −78° C. (dry ice bath) under N$_2$ atm. After removing the dry ice bath, the mixture was stirred in refluxing NH$_3$ (dry ice condenser) for 15 min. After adding 2 mL dry MeOH (slowly!), the resulting mixture was stirred while blowing off NH$_3$ with a N$_2$ stream. The MeOH solution was treated with Dowex 50×8 [H$^+$] until pH ~8–9, and then filtered. The resin was washed with MeOH. The residue was concentrated and kept on a vacuum line to dry. Under a N$_2$ atmosphere, the residue was treated with 1 mL dry pyridine and 0.5 mL Ac$_2$O, and stirred at r.t. overnight. TLC (EtOAc) showed that hexasaccharide 26 is major component. Upon concentration, the residue was purified by column chromatography on silica (1:4 hex:EtOAc).

Preparation of Hexasaccharide 17

Hexasaccharide 26 (10.0 mg, 6.3 mmol) under N$_2$ at 0° C. was treated with 0.5 mL dry CH$_2$Cl$_2$. Dioxirane solution (0.20 mL) was added, and the mixture was stirred at 0° C. ~40 min. TLC (EtOAc) showed no trace of 26. Solvents were evaporated with a N$_2$ stream. The epoxide was dried on a vacuum line for ~2 h. The epoxide was treated under a N$_2$ atmosphere with 0.5 mL allyl alcohol (passed through basic alumina to dry) and 0.5 mL dry THF. On cooling to −78° C., 1.0M ZnCl$_2$ (10 mL) in dry Et$_2$O was added. After warming slowly to r.t., the mixture was stirred overnight. Saturated aq. NaHCO$_3$ (5 mL) was added, and the mixture was extracted with 3×5 mL EtOAc. The combined organic layers were dried over MgSO$_4$, filtered and concentrated to an oil, which was dried on a vacuum line for ~2 h. The residue was treated to pyridine:Ac$_2$O (2:1, 1.5 mL) while stirring overnight. Solvents were removed, and the residue was purified by column chromatography on silica (1:4 hex:EtOAc), affording hexasaccharide 17 as a colorless solid. Yield: 5.5 mg.

Results and Discussion

Figure 2:
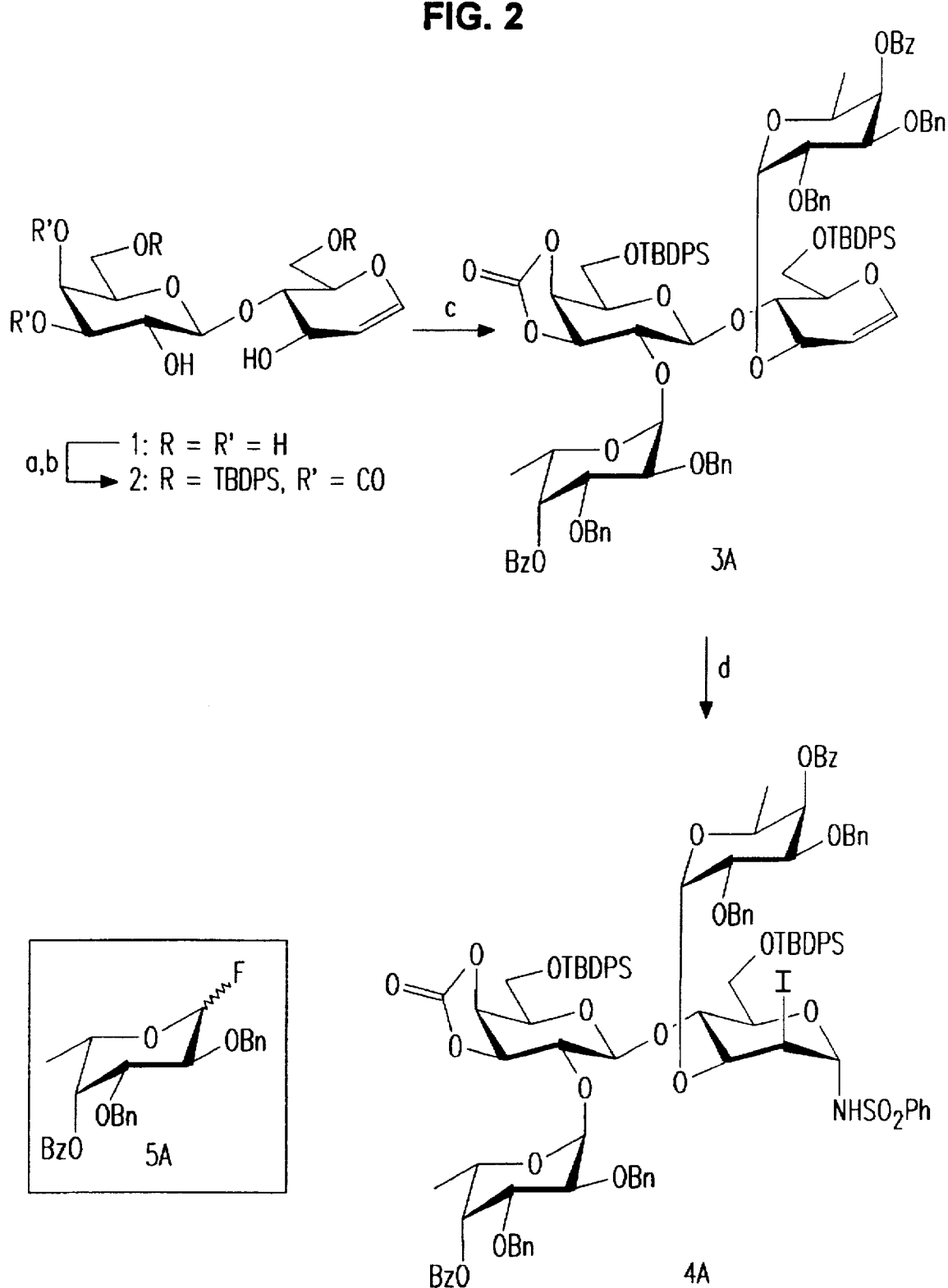
FIG. 2 shows the synthesis of 4a. Reagents: a) TBDPSCL, imidazole/DMF 84%; b) carbonyldiimidazole, cat. imidazole, THF (65%) c) 5a, di-tert-butylpyridine, AgClO$_4$, SnCl$_2$, ether (51%); PhSO$_2$NH$_2$, 1(sym-coll)$_2$ClO$_4$ (94%).

A Highly Convergent Synthesis of the Lewis Y Blood Group Determinant in Conjugatable Form Construction of the Le$^y$ determinant commences with lactal (1a) (W. N. Haworth, E. L. Hirst, M. M. T. Plant, R. J. W. Reynolds, *J. Chem. Soc.* 1930, 2644) as shown in FIG. 2. Capping both primary hydroxyl groups as their TBDPS ethers under standard conditions was followed by simple engagement of the 3' and 4' hydroxyl functions as a cyclic carbonate 2a. The stereospecific introduction of two α-linked fucose residues gave tetrasaccharide glycal 3a in 51% yield in a single step. The donor used was the known fluorosugar 5a (S. J. Danishefsky, J. Gervay, J. M. Peterson, F. E. McDonald, K. Koseki, T. Oriyama, D. A. Griffith, C.-H. Wong, D. P. Dumas, *J. Am. Chem. Soc.* 1992, 114, 8329) following a modification of the original Mukaiyama conditions. (T. Mukaiyama, Y. Murai, S. Shoda, *Chem. Lett.* 1981, 431) Glycal 3a corresponds to the Le$^y$ hapten, lacking the N-acetyl function in the glucose residue. The problem was then to introduce this group as well as a galactose spacer module.

Figure 3:
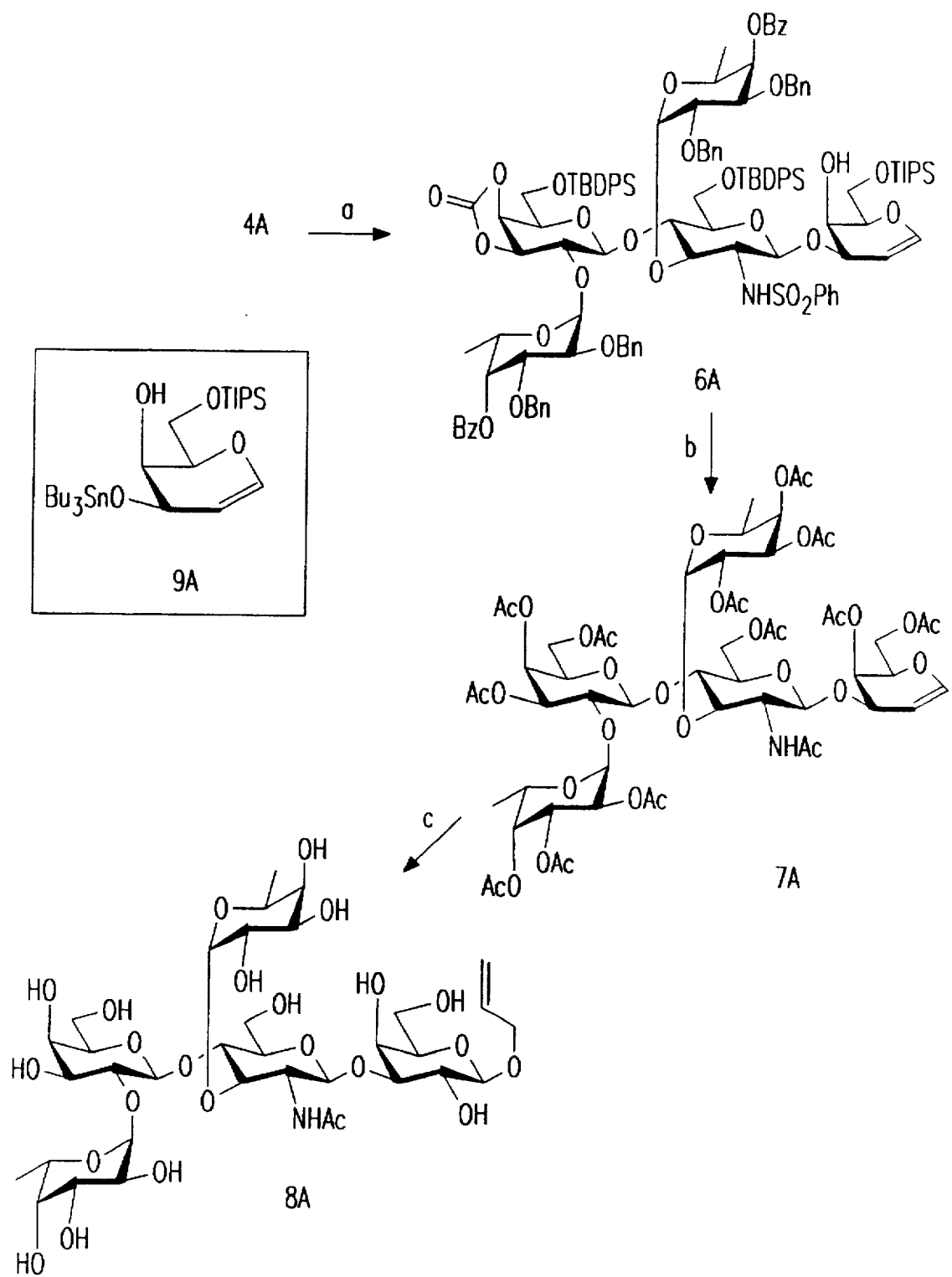
FIG. 3 shows the synthesis of 8a. Reagents: a) 9a, AgBF$_4$, 4A mol. sieves, THF (75%); b) i. TBAF, THF; ii. Na/NH$_3$; iii Ac$_2$O, pyr. c) i. 3,3-dimethioxirane; allyl alcohol, ZnCl$_2$ (72%); ii. NaOMe, MeOH (quant.).

Methodology developed previously (D. A. Griffith, S. J. Danishefsky, "On the Sulfonamidoglycosylation of Glycals. A Route to Oligosaccharides With 2-Aminohexose Subunits+", *J. Am. Chem. Soc.* 1990 112, 5811) proved appropriate to attain these goals. Glycal 3a was treated with iodonium dicollidine perchlorate and benzenesulfonamide to afford iodosulfonamide 4a. Azaglycosylation using the 3-stannyl ether of galactal (9a) (S. J. Danishefsky, K. Koseki, D. A. Griffith, J. Gervay, J. M. Peterson, F. E. McDonald, T. Oriyama, *J. Am. Chem. Soc.* 1992, 114, 8331) in the presence of silver tetrafluoroborate gave pentasaccharide glycal 6a in 75% yield as shown in FIG. 3. Having 6a in hand, one can iterate the azaglycosylation sequence or activate the glycal as its epoxide and continue with further glycosylations. To demonstrate the ability to fashion a conjugatable form of Le$^y$ hapten, formation of the allyl glycoside was important. The feasibility of converting the sulfonamido group into the target acetamide was demonstrated. Glycal 6a was deprotected in two steps as shown. Peracetylation afforded acetamido glycal 7a. Activation of the glycal as its epoxide with dimethyldioxirane (R. L. Halcomb, S. J. Danishefsky, *J. Am. Chem. Soc.* 1989, 111, 6661), followed by epoxide opening with allyl alcohol in the presence of zinc chloride gave the desired peracetylated β-allyl pentasaccharide which was deacetylated by action of methoxide to provide the target Le$^y$ hapten as its β-allyl glycoside 8a. (8a [α]$_D$−72.7° (c. 1 MeOH); IR (thin film) 3350, 2940, 2900, 2830, 1650, 1550, 1365, 1300, 1155, 1070, 1030; $^1$H NMR (400 MHz, CD$_3$OD) δ5.95 (m, 1H), 5.32 (d, J=17.25 Hz, 1H), 5.14–5.19 (m, 2H), 5.04 (d, J=3.83 Hz, 1H), 5.02 (d, J=3.50 Hz, 1H), 4.68 (d, J=8.15 Hz, 2H), 4.51 (d, J=5.70 Hz, 1H) 3.40–4.38 (m, 27H), 1.96 (s, 3H), 1.23 (m, 6H); HRMS (FAB) cald for C$_{35}$H$_{56}$NO$_{24}$Na 900.3325 found 900.3310) The aldehyde, derived by ozonolysis of 8a, could be conjugated to a carrier protein by the method of Bernstein and Hall.

This synthesis is the most direct route to the Le$^y$ determinant known. (O. Hindsgaul, T. Norberg, J. Le Pendu, R. U. Lemieux, *Carbohydr Res.* 1982, 109, 109; U. Spohr, R. U. Lemieux ibid, 1988, 174, 211; for previous syntheses, see: J. C. Jacquinet, P. Sinay, *J. Org. Chem.* 1977, 42, 720; S. Nilsson, H. Lohn, T. Norberg, *Glycoconjugate J.* 1989, 6, 21; R. R. Schmidt, A. Topfer, *Tetrahedron Lett.* 1991, 32, 3353; W. Kinzy, A. Low, *Carbohydrate. Res.* 1993, 245, 193) The method is stereospecific at each step, and it illustrates the versatility of glycals both as donors and acceptors and takes advantage of 1,2-glycal epoxides and their presumed N-sulfonylaziridine counterparts. The method also makes possible extensive analog preparation and variation of conjugation strategies.

The synthesis of 3a and 6a are shown below

3a: To 2.00 g (2.47 mmol) of lactal carbonate 2a was added 4.44 g (9.86 mmol) of fucosyl fluoride 5a. The mixture was azeotroped 5 times with benzene and placed under high vacuum for two hours. Under an argon atmosphere 2.77 ml (12.33 mmol) of di-tert-butyl pyridine and 16 ml of dry ether were added. 2.0 g of freshly activated 4A molecular sieves were added and the mixture stirred one hour at room temperature. In an argon glove bag, 2.34 g (12.33 mmol) of stannous chloride (SnCl$_2$) and 2.56 g (12.33 mmol) of silver perchlorate (AgClO$_4$) were added. The flask was equipped with a reflux condensor and the reaction brought to reflux for 72 hours. The reaction was quenched with 5 ml of saturated bicarbonate and filtered through a pad of celite. Diluted with 50 ml ethyl acetate and washed 2 times with sat. bicarbonate, 2 times with sat. copper sulfate and 2 times with sat. brine. The organics were dried over MgSO$_4$ and concentrated. Flash chromatography in 20% ethyl acetate/hexanes afforded 2.10 g (51%) of a white foam 3a: $[\alpha]_D$−78.9 (c.555.CHCl$_3$); IR (thin film) 3040, 3000, 2905, 2860, 2830, 1820, 1800, 1710, 1635, 1585, 1570, 1480, 1460, 1440, 1415, 1370, 1350, 1300, 1260, 1205, 1145, 1100, 950, 735, 695, $^1$H NMR (400 MHz.CDCl$_3$) δ8.09 (d, J=8.12 Hz, 2H), 8.00 (d, J=8.26 Hz, 2H) 7.66 (m, 4H), 7.59 (d=J=6.74 Hz, 4H), 7.56 (t, J=7.27 Hz, 1H), 7.30–7.50 (m,22H) 7.16–7.26 (m,10H) 7.09 (m,2H), 6.99 (t, J=7.59 Hz, 2H) 6.89 (t, J=7.97 Hz, 1H), 6.43 (d, J=6.08 Hz, 1H), 5.46 (bs, 1H), 5.38 (bs, iH), 5.35 (d, J=3.42 Hz, 1H), 4.89 (d, J=11.35 Hz, 1H), 4.75–4.80 (m, 4H), 4.72 (d, J=5.88 Hz, 2H), 4.69 (d, J=4.27 Hz, 2H), 4.36–4.55 (m, 5H), 4.28 (q, J=6.51 Hz, 1H), 4.17 (bd, J=5.46 Hz, 1H),3.90–4.00 (m,6H), 3.85 (d, J=2.99 Hz, 1H), 3.82 (d, J=2.89 Hz, 1H), 3.56–3.78 (m, 4H), 1.07 (m, 24H); HRMS (FAB): calcd for C$_{99}$H$_{106}$O$_{20}$Si$_2$Na 1694.6740 found 1694.6787.

6a: 230 mg (0.12 mmol) of iodosulfonamide 4a was azeotroped 5 times with dry benzene and placed under high vacuum for two hours. Added 2.4 ml of THF solution of 15 eq. of tin ether 9a (generated by azeotrophic removal of water overnight with a Dean-Stark trap equipped with freshly activated 4 A mol. sieves from 561 mg (1.80 mmol) of 6a-TIPS-galactal and 673 μl (1.32 mmol) bis(tributylin) oxide in 80 ml of benzene). To this solution stirring under an argon atmosphere was added 200 mg of freshly activated 4A powdered molecular sieves. Stirred one hour at room temperature. Cooled solution to −78° C. and added, via cannula, a solution of 187 mg (0.96 mmol) of silver tetrafluroborate in 2.4 ml of THF. Warmed to room temperature over 15 hours and quenched the reaction, which had turned bright yellow, with 2 ml. of sat. bicarbonate. The reaction mixture was filtered through a pad of celite into a separatory funnel. The celite pad was washed thoroughly with ethyl acetate. The organics were washed twice with sat. bicarbonate and twice with sat. brine. The organics were dried over MgSO$_4$. Concentration and chromatography in 25% ethyl acetate/ hexanes gave 193 mg (75%) as a white foam 6a: $[\alpha]_D$− 126.4° (c.505.CHCl$_3$), IR (thin film) 3500, 3040, 3000, 2905, 2840, 1820, 1800, 1705, 1635, 1590, 1440, 1410, 1255, 1195, 1100, 1080, 1035, 815, 730, 695; $^1$H NMR (400 MHz, CDCl$_3$) δ8.09 (app t, 4H), 7.08–7.65 (m, 46H), 6.90 (t, J=7.65 Hz, 3H), 6.76 (d, J=6.91 Hz, 2H), 6.12 (d, J=6.59 Hz, 1H), 5.50 (bs 1H), 5.45 (bs 1H), 5.28 (app t, 2H), 3.03–4.91 (m, 36H), 1.09 (m, 45H); LRMS (FAB): cald for C$_{120}$H$_{141}$NO$_{26}$SSi$_3$Na 2153 found 2153.

A Strategy for the Assembly of Complex, Branched Oligosaccharide Domains on a Solid Support: An Application to a Concise Synthesis of the Lewis$^b$ Domain in Bioconjugatable Form.

Figure 4:
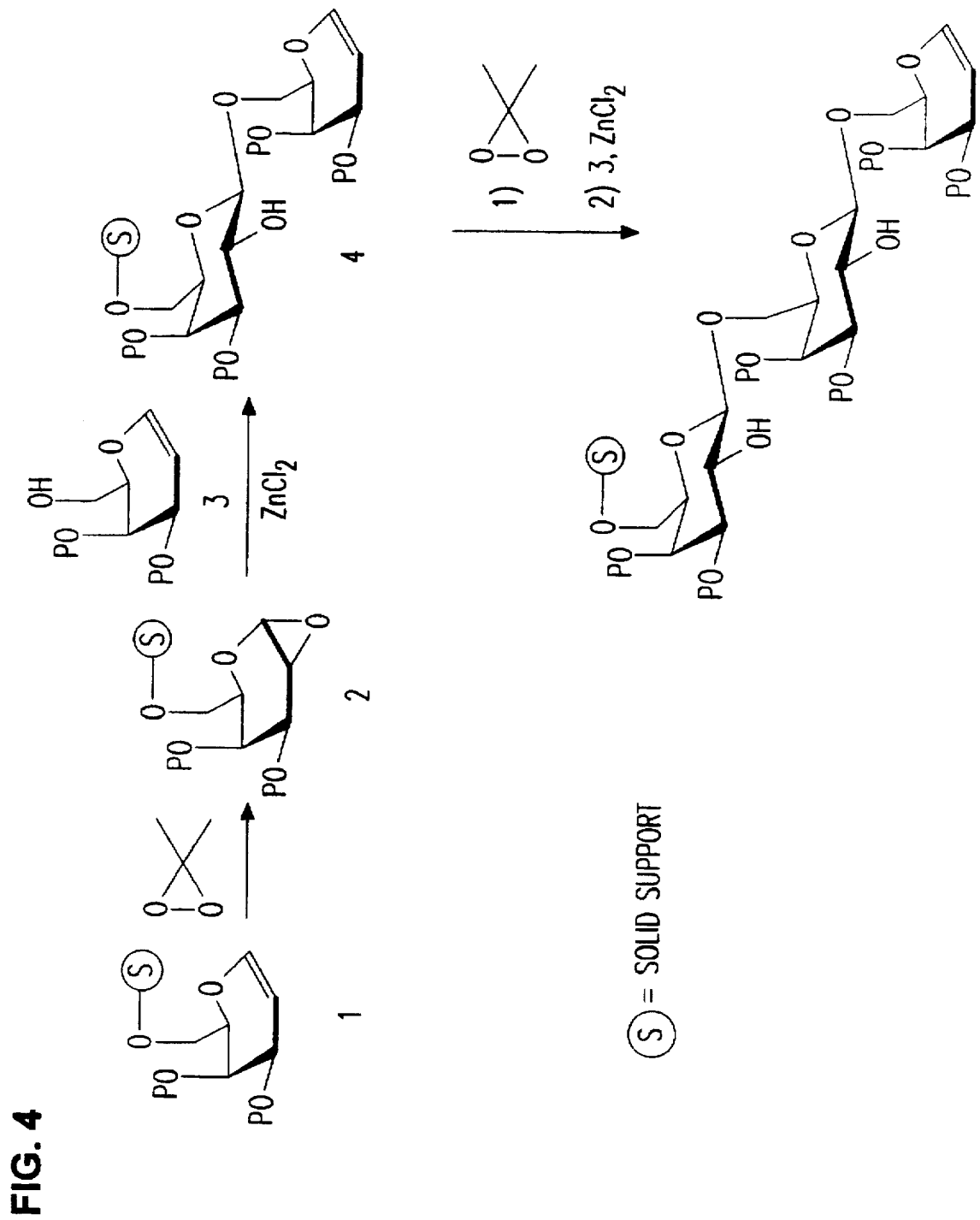
FIG. 4 shows a strategy for the solid-phase of oligosaccharides using the glycal assembly method.

The assembly of the Le$^b$ (type 1) domain is a relatively more difficult undertaking than was the Le$^y$ (type 2) target, wherein lactal was used as a convenient starting material. In the case of the type 1 determinant, lactal is not a useful starting material. The synthesis of the Le$^b$ system offered an opportunity to apply the polymer-based oligosaccharide construction method. (S. J. Danishefsky, K. F. McClure, J. T. Randolph, R. B. Ruggeri, Science 1993, 260, 1307) The strategy is summarized in FIG. 4, wherein polymer-bound glycal 1 is activated for glycosyl donation via direct formation of a 1,2-anhydro derivative 2. Reaction of 2 with acceptor glycal 3 furnishes 4. Reiteration is achieved by means of direct epoxidation and reaction with acceptor 3. The self-policing nature of the method and the simple "one time" purification at the end of the synthesis are useful features.

Figure 5:
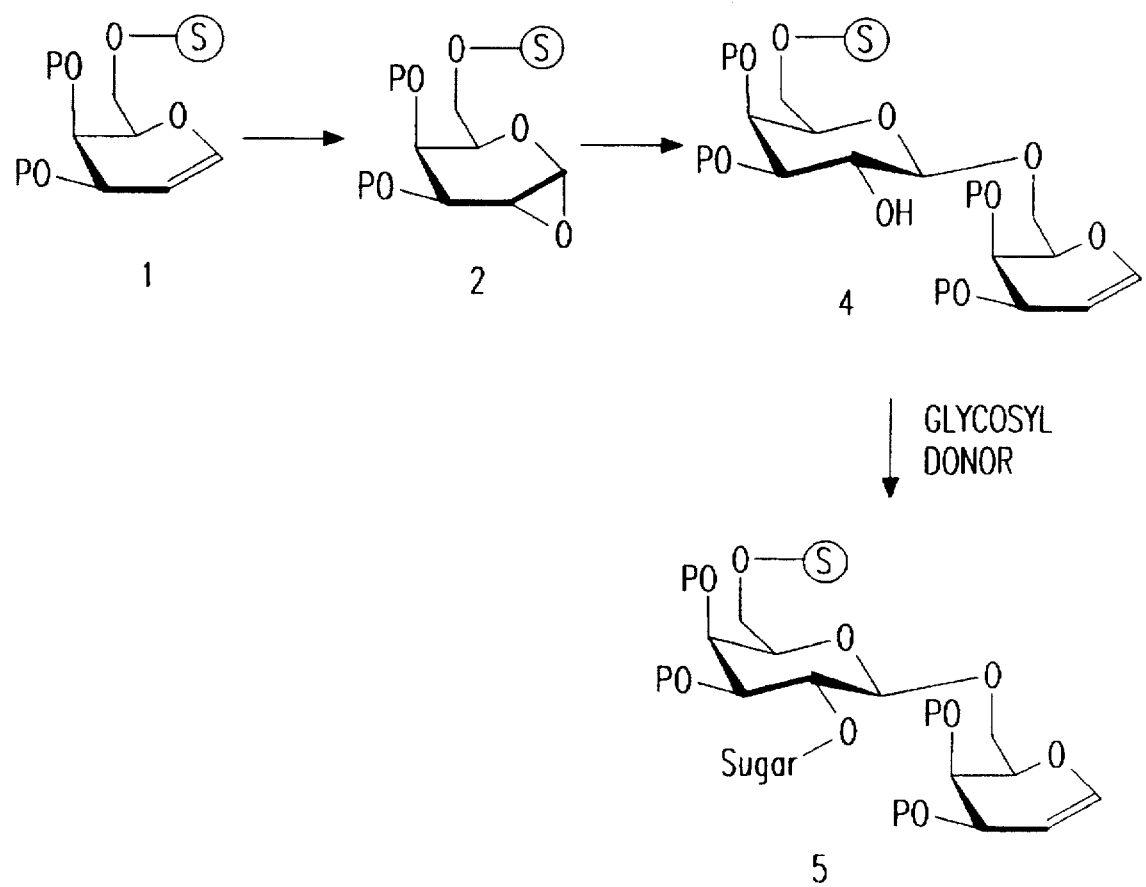
FIG. 5 shows the application of the solid-support method to the assembly of 1,2-branching patterns of complex carbohydrates.

The present invention discloses an important additional dimension of the polymer-bound method. The logic is captured by inspection of FIG. 5. Each glycosylation event generates a unique C$_2$ hydroxyl. In principle (and in fact, see infra) this hydroxyl can function as a glycosyl acceptor upon reaction with a solution based donor. The glycal linkage of 5, still housed on the support, can be further elongated. In this way, branching at C$_2$ is accomplished while minimizing the requirement for protecting group machinations. (For an application of this strategy in the synthesis of a complex saponin, see: J. T. Randolph, S. J. Danishefsky, J. Am Chem Soc. 1993, 115, 8473)

In principle, this branching can be implemented at any site in a growing chain. For such an extension, it would be necessary to cap all previously generated hydroxyl groups generated on the "polymer side" (non-reducing end) of the growing domain. Thus, the polymer-bound oligosaccharide can serve as either donor or acceptor, wherever appropriate.

Initial efforts at reduction to practice identified tetrasaccharide glycal 6, bearing H-type 2 blood group specificity, as a goal. Polymer-supported galactal 7 (using as polymer support polystyrene crosslinked with 1% divinylbenzene functionalized using published procedures: T.-H. Chan, W.-Q. Huang, J. Chem. Soc., Chem. Commun. 1985, 909; M. J. Farrall. J. M. J. Frechet, J. Org. Chem 1976, 41, 3877) reacted with a solution of 3,3-dimethyldioxirane (R. W. Murray, R. Jeyaraman, J. Org. Chem. 1985, 50, 2847), to provide the corresponding 1,2-anhydrosugar glycosyl donor, which was treated with a solution of glucal derivative 8 in the presence of ZnCl$_2$ to provide 9 (R. L. Halcomb, S. J. Danishefsky, J. Am. Chem Soc. 1989, 111, 6661) This polymer-bound disaccharide acted as a glycosyl acceptor upon treatment with a solution of fucosyl fluoride 10 (K. C. Nicolaou, C. W. Hummel, Y. Iwabuchi, J. Am. Chem. Soc. 1992, 114, 3126) in the presence of Sn(OTf)$_2$ thereby giving 11. Retrieval of the trisaccharide glycal from the support was accomplished using tetrabutylammonium fluoride (TBAF) to afford 12 in 50% overall yield from 7.

The trisaccharide, retrieved from the polymer, could then be further elaborated. Toward this end, compound 12 was converted to silyl ether 13 by reaction with TIPSCl. The latter was converted to the iodosulfonamide derivative 14 by the action of I(coll)$_2$ClO$_4$ in the presence of PhSO$_2$NH$_2$. Reaction of 14 with galactal stannyl ether derivative 15 in the presence of AgBF$_4$ gave 16 77% yield. (D. A. Griffith, S. J. Danishefsky, J. Am. Chem Soc. 1990, 112, 5811) Tetrasaccharide glycal 16 was deprotected and peracetylated to afford 6. (S. J. Danishefsky, K. Koseki, D. A. Griffith, J. Gervay, J. M. Peterson, F. E. MsDonald, T. Oriyama, J. Am. Chem Soc. 1992, 114, 8331)

Figure 6:
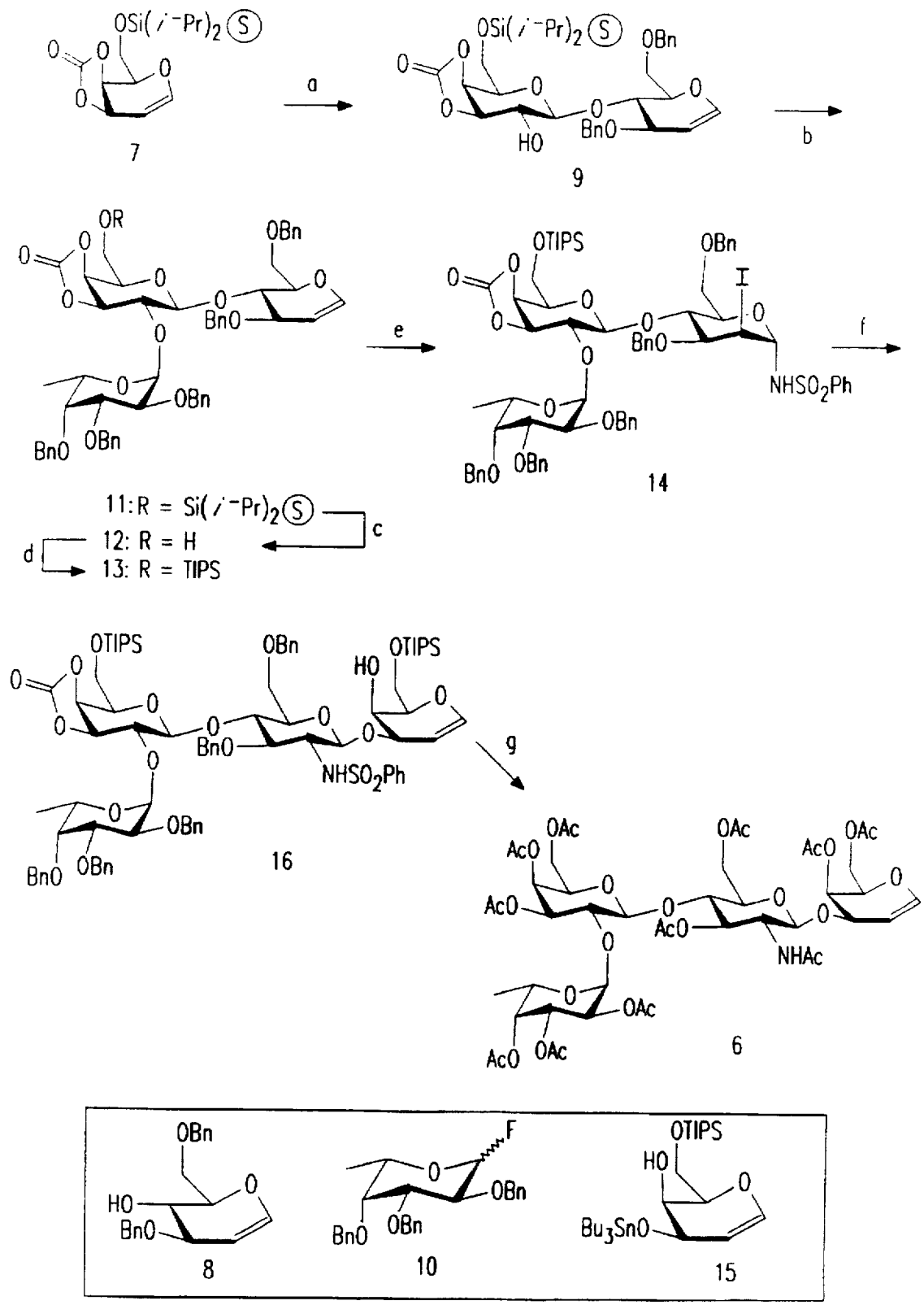
FIG. 6 shows the synthesis of a tetrasaccharide having H-type 2 blood group specificity. Reagents: (a) 1. 3,3-dimethyldioxirane, CH$_2$Cl$_2$; 2. 8, ZnCl$_2$, THF; (b) 10, Sn(OTf)$_2$, di-tert-butylpyridine, THF; (c) TBAF, AcOH, THF; (d) TIPSCl, imidazole, DMF; (e) I(coll)$_2$ClO$_4$, PhSO$_2$NH$_2$, CH$_2$Cl$_2$; (f) 15, AgBF$_4$, 4A M.S., THF; (g) 1. TBAF, AcOH, THF; 2. Na/NH$_3$; 3. Ac$_2$O, pyridine.
Figure 7A:
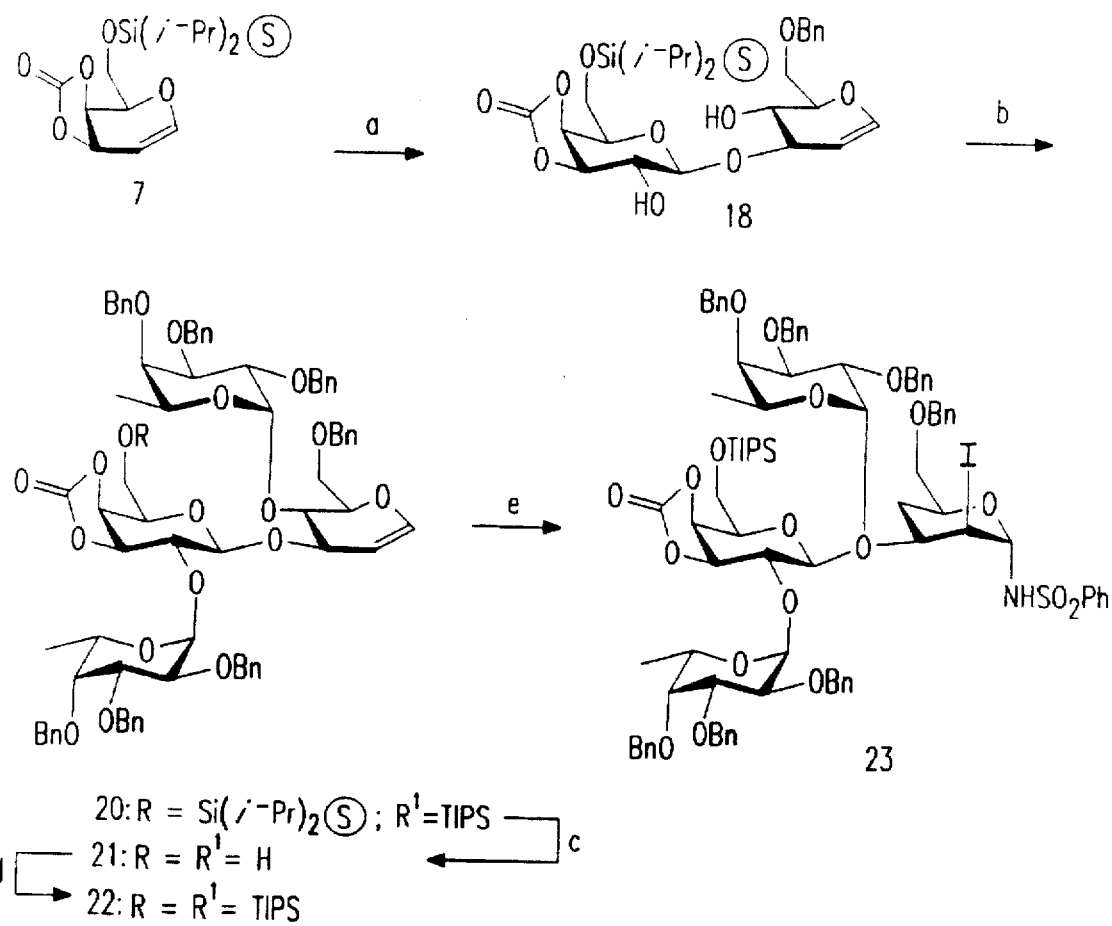
FIG. 7a and 7b show the synthesis of a Le$^b$ hexasaccharide in bioconjugatable form. Reagents: (a) 1. 3,3-dimethyldioxirane, CH$_2$Cl$_2$; 2. 19, ZnCl$_2$, THF; (b) 10, Sn(OTf)$_2$ di-tert-butylpyridine, THF; (c) TBAF, AcOH, THF; (d) TIPSCl, imidazole, DMF; (e) I(coll)$_2$ClO$_4$, PhSO$_2$NH$_2$, CH$_2$Cl$_2$; (f) 24, AgBF$_4$, 4A M.S., THF; (g) 1. TBAF, AcOH, THF; 2. Na/NH$_3$; 3. Ac$_2$O, pyridine; (h) 1. 3,3-dimethyldioxirane, CH$_2$Cl$_2$; 2. allyl alcohol, ZnCl$_2$; 3. NaOMe, MeOH.
Figure 7A:
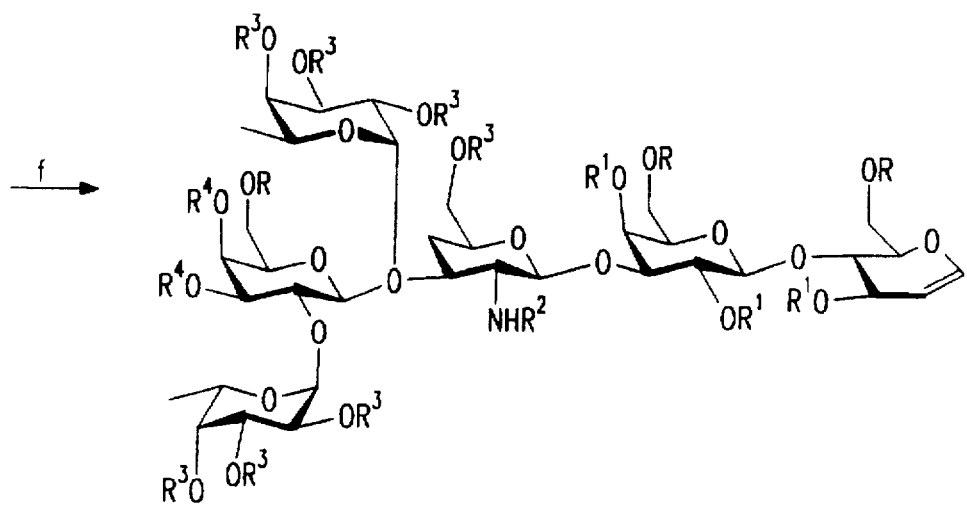
Figure 7B:
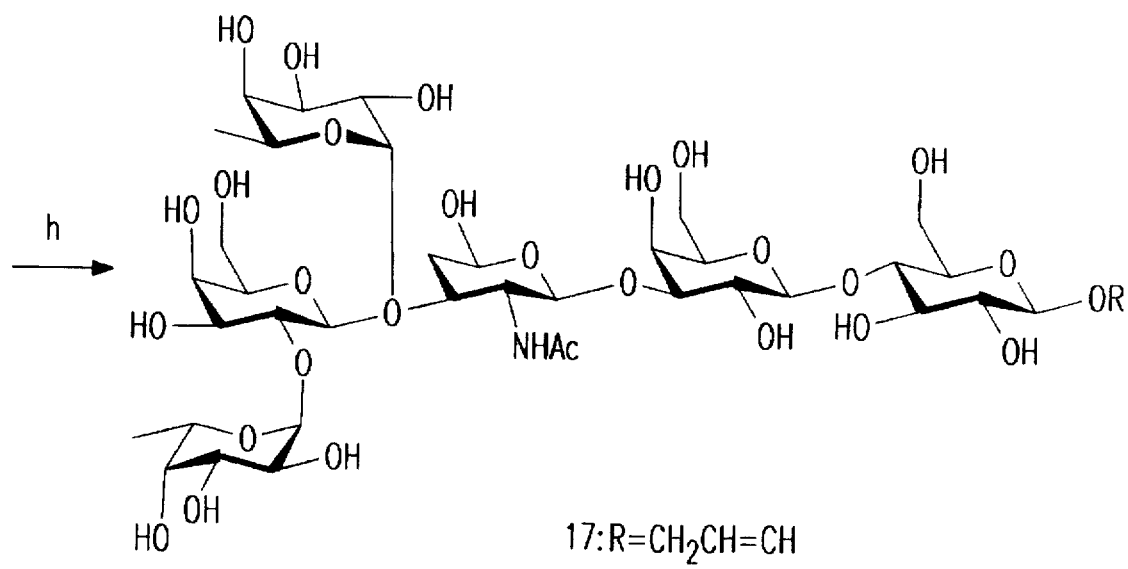
Figure 7B:
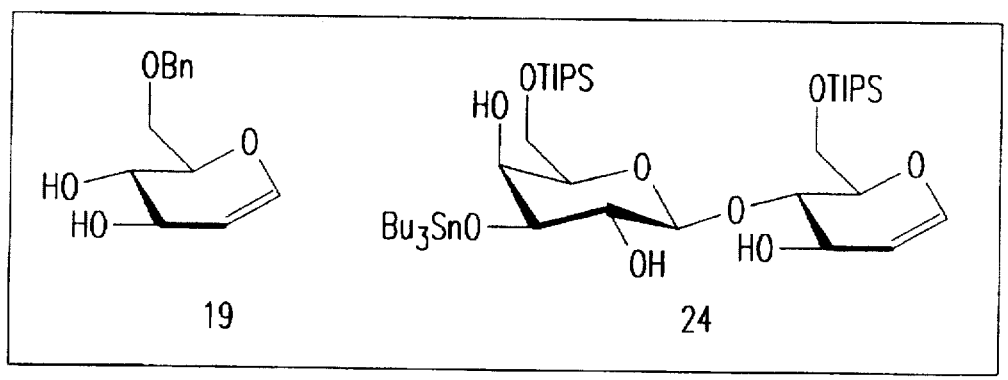
Figure 7B:
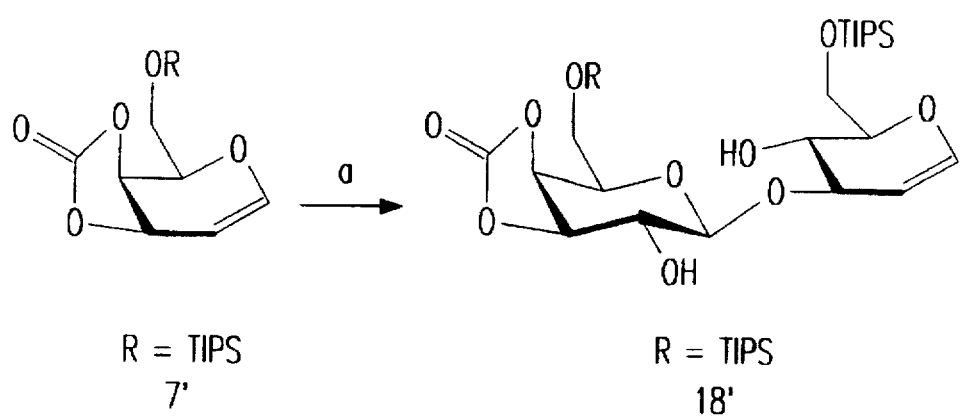

Thus, the synthesis of the full H-type determinant was achieved by sequential polymer- and solution-based maneuvers. The next target was the more complex Le$^b$ hexasaccharide 17. The campaign proceeded as shown in FIG. 6. Polymer-bound galactal 7 was converted to 18 upon epoxidation with 3,3-dimethyldioxirane followed by reaction with glucal derivative 19. This disaccharide diol was then bisfucosylated using fucosyl donor 10 in the presence of Sn(OTf)$_2$ to afford 20. Retrieval from the support with TBAF provided 21, which was obtained in 40% overall yield from 7. Compound 21 reacted with TIPSCl to give 22.

Iodosulfonamide 23, obtained from 22 using I(coll)$_2$ClO$_4$ and PhSO$_2$NH$_2$, reacted with lactal derivative 24 in the presence of AgBF$_4$ to provide hexasaccharide glycal 25 in 55% yield. Deprotection of 25 was accomplished in two stages (TBAF to remove the silyl ethers, followed by Na/NH$_3$ reduction to remove the aromatic protecting groups), and the crude product was peracetylated to give 26 in a 51% overall yield. Compound 26 was converted, via the 1,2-anhydrosugar derivative, to allyl glycoside 17, which can be activated by ozonolysis to the aldehyde (R=CH$_2$CHO) for subsequent coupling to a protein by the method of Bernstein and Hall.

In sum, the present invention extends the solid-support glycal assembly method for complex carbohydrate domain synthesis to include the branching patterns critical for biorecognition. Specifically, the determinant for the binding of *H. pylori* to human gastric epithelium has been stereospecifically fashioned, with simplicity, in a way which provides significant relief from some of the complexities of protecting group manipulations.

Experimental Procedure

6: $^1$H NMR (400 MHz, CDCl$_3$); δ6.39 (d, 1H, J=6.2 Hz, H$_1$ galactal), 5.65 (d, 1H, J=8.9 Hz, NHAc), 5.35 (d, 1H, J=3.8 Hz), 5.33 (m, 1H), 5.29 (d, 1H, J=2.6 Hz), 5.27 (d, 1H, J=3.1 Hz), 5.17–5.09 (m, 2H), 4.97–4.90(m,2H), 4.81 (dd, 1H, J=3 Hz, J=6.1 Hz, H$_2$ galactal), 4.75 (d, 1H, J=8.0 Hz), 4.52 (m, 1H), 4.48 (dd, 1H, J=12.0 Hz), 4.44–4.06 (m, 8H), 3.88–3.77 (m, 4H), 3.61 (m, 1H), 2.18–1.97 (m, 33H, COCH$_3$), 1.18 (d, 3H, J=6.5 Hz, CH$_3$ fucose); $^{13}$C NMR (CDCl$_3$): δ170.80, 170.77, 170.72, 170.67, 170.62, 170.34, 170.21, 170.09, 170.01, 169.99, 169.65, 144.92 (C$_1$ galactal), 100.22, 98.83, 98.58, 95.55, 74.48, 73.38, 73.13, 73.06, 71.48, 71.01, 70.68, 67.97, 67.42, 67.18, 67.05, 65.94, 64.83, 62.35, 62.22, 60.88, 60.37, 54.21, 23.23, 22.15, 20.85, 20.82, 20.79, 20.76, 20.65, 20.61, 20.57, 15.51, (C$_6$ fucose); IR (thin film): 3368.7 (NH),2965.6, 2934.6, 1746.5 (C=O), 1537.5, 1435.9, 1371.3, 1228.5, 1065.0, 1046.0; [α]$_D^{23}$=−51.1° (c 1.8, CH$_2$Cl$_2$); HRMS (FAB); calcd. for C$_{46}$H$_{63}$NNaO$_{28}$: m/z=1100.3434, found 1100.3436.

21: Polymer-bound galactal 7 (loading=0.85 mmol glycal/ g), which had been placed in a round-bottom flask equipped with a fritted outlet, was suspended in CH$_2$Cl$_2$ under N$_2$, cooled to 0° C., and then treated with a solution of 3,3-dimethyldioxirane. The mixture was stirred (teflon-coated magnetic stir bar) for 40 min. at 0° C., after which time solubles were removed by filtration through the fritted outlet (N$_2$ pressure). The polymer bound 1,2 anhydrosugar was evacuated (ca. 0.1 torr) for several hours in order to dry the material for the next step. This material was once again placed under N$_2$ before being treated with 19 (~10 molar equivalents as a 0.5M solution in THF). The suspension was cooled to −40° C., and treated with ZnCl$_2$ (~2 molar equivalents as a 1.0M solution in THF). The reaction mixture was allowed to slowly warm to rt (over ca. 2 h), and then stirred an additional 3–4 h. Solubles were removed by filtration, and polymer 18 was washed several times with THF and then dried in vacuo. To compound 18 was added, in a glove bag, solid Sn(OTf)$_2$ (~molar equivalents), and the mixture was placed under N$_2$ and cooled to 0° C. before being treated with 10 (~5 molar equivalents as a 0.2M solution in THF and di-tert-butylpyridine (~8 molar equivalents). The suspension was allowed to warm to rt and stirred 8–10 h. The mixture was rinsed with anhydrous THF (2 times), 1,4-dioxane (2 times), again with THF, and then dried in vacuo. Compound 20 (100 mg) was suspended in THF, treated with a 1:3 mixture of AcOH and TBAF (~0.2M in TBAF, ~10 molar equivalents), and the mixture was stirred for 18 h at 40° C. The polymer was rinsed with THF (3 times), and the combined rinsings were concentrated and purified by column chromatography on silica gel (1:1 EtOAc: hexanes). Compound 21 (18 mg) was obtained as a colorless solid (40% overall yield from 7): $^1$H NMR (400 MHz, CDCl$_3$): δ7.40–7.25 (m, 30H, Ar H), 6.18 (d, 1H, J=6.0 Hz, H$_1$ glucal), 5.26 (d, 1H, J=3.5 Hz, H$_1$ fucose), 5.09 (d, 1H, J=3.7 Hz, H$_1$ fucose), 4.96 (t, 2H, J=10.8 Hz, PhCH$_2$), (4.90–4.56 (m, 13H), 4.43 (m, 1H), 4.15–4.06 (m, 4H), 3.97 (dt, 1H, J=8.3 Hz, J=2.4 Hz), 3.87–3.65 (m, 10H), 3.64 (d, 1H), 3.57 (d, 1H), 2.69 (br, 1H, OH), 2.52 (br, 1H, OH), 1.11 (d, 3H, J=7.0 Hz, CH$_3$ fucose), 1.09 (d, 3H, J=7.0 Hz, CH$_3$ fucose); $^{13}$C NMR (CDCl$_3$); δ153.37 (C=O), 145.75 (C$_1$ glucal), 138.60, 138.52, 138.19, 137.61, 128.55, 128.52, 128.44, 128.24, 128.16, 128.07, 127.62, 127.56, 127.45, 98.71, 98.38, 97.65, 97.34, 79.26, 78.87, 78.67, 78.01, 77.79, 77.65, 76.37, 76.10, 74.92, 74.40, 74.16, 73.95, 72.86, 72.64, 72.53, 67.43, 67.29, 61.31, 60.90, 16.65 (C$_6$ fucose), 16.53, (C$_6$ fucose); IR (thin film): 3467.0 (OH), 3029.6, 2923.6, 1807.2 (C=O), 1647.3, 1496.0, 1453.5, 1358.1, 1240.2, 1095.6, 1049.2, 738.5, 697.2; [α]$_{D23}$=−82.5° (c 0.4, CH$_2$Cl$_2$); HRMS (FAB); calcd. for C$_{67}$H$_{74}$NaO$_{18}$: m/z=1189.4772, found 1189.4757.

25: To a mixture of 23 (60 mg, 34 μmol) and powdered 4A molecular sieves (200 mg) under N$_2$ was added, via canula, a solution of 24 (0.21 mmol) in anhydrous THF (1.5 mL). The stirred suspension was cooled to −78° C. before being treated with a solution of AgBF$_4$ (0.21 mmol) in 0.25 mL of anhydrous THF. The mixture was stirred and allowed to slowly warm to rt overnight. The suspension, which had developed a bright-yellow color, was heated, with stirring, at 45° C. for an additional 36 h, until the TLC (2.5 EtOAc:hexanes) showed no trace of 23. The mixture was treated with saturated aqueous NH$_4$Cl (5 mL) and then extracted with EtOAc (3×10 mL), and the organics were dried over MgSO$_4$. The crude product was purified by silica gel chromatography (1:3 EtOAc:hexanes) to give 25 as a colorless oil (42 mg, 55%): $^1$H NMR (400 MHz, acetone-d$_6$): δ8.17(d, 2H, J=7.3 Hz, PhSO$_2$), 7.50–7.20 (m, 33H, ArH), 6.52 (d, 1H, J=10.5 Hz, NH), 6.30 (dd, 1H, J=6.0 Hz, H$_1$ glucal), 5.35–5.32 (m, 2H), 5.25 (d, 1H, J=7.9 Hz), 5.15 (m, 2H), 4.99–4.92 (m, 3H), 4.86–4.52 (m, 14H), 4.45 (dd, 1H, J=7.91 Hz, J=2.4 Hz), 4.32–4.23 (m, 3H), 4.22 (dd, 1H), 4.17 (d, 1H, J=10.1 Hz), 4.08–3.84 (m, 18H), 3.79–3.73 (m, 2H), 3.66 (m, 1H), 3.55 (t, 1H, J=6 Hz), 3.50 (dd, 1H, J=9.7 Hz), 1.33 (d, 3H, J=6.5 Hz, CH$_3$ fucose), 1.31 (d, 3H, J=6.4 Hz, CH$_3$ fucose), 1.20–0.98 (m, 84H, 3×Si(i-Pr)$_3$); $^{13}$C NMR (acetone-d$_6$): 145.66 (C=O), 132.72, 131.48, 131.45, 131.28, 131.16, 130.77, 130.48, 121.31, 120.11, 119.86, 119.78, 119.25, 95.63, 94.70, 91.37, 89.64, 89.31, 86.52, 73.38, 72.24, 71.00, 70.71, 70.37, 69.80, 69.59, 69.06, 68.23, 67.92, 67.38, 67.10, 66.49, 65.67, 65.33, 64.60, 64.34, 64.03, 63.45, 63.30, 59.46, 58.83, 58.37, 54.45, 53.32, 49.86, 19.67 (C$_6$ fucose), 18.42 (C$_6$ fucose), 9.55, 9.48, 9.45, 9.31, 9.23, 3.82, 3.70, 3.64; IR (thin film): 3491.9 (OH), 3030.1, 2941.2, 2865.5, 1835.8, 1819.5, 1649.8, 1496.2, 1462.3, 1349.9, 1245.5, 1155.2, 1095.1, 1049.4, 882.2, 734.8, 692.0; [α]$_{D23}$=−33.8° (c 2.0, CH$_2$Cl$_2$); HRMS (FAB): calcd for $^{12}$C$_{120}$$^{13}$CH$_{179}$NNaO$_{29}$SSi$_4$: m/z=2278.1292, found 2278.1296.

17: $^1$H NMR (400 MHz, CD$_3$OD): δ6.00 (m, 1H, J=5.6 Hz, CH$_2$CH=CH$_2$), 5.37 (dd, 1H, J=1.6 Hz, J=7.3 Hz, CH$_2$CH=CH$_2$), 5.20 (dd, 1H, J=1.6 Hz, J=9.5 Hz, CH$_2$CH=CH$_2$), 5.18 (d, 1H, J=3.9 Hz, H$_1$ fucose), 5.10 (d, 1H, J=3.8 Hz, H$_1$ fucose), 4.64 (d, 1H, J=6.9 Hz), 4.45 (d, 1H, J=7.4 Hz), 4.43–4.23 (m, 2H), 4.27 (dd, 1H, J=9.3 Hz, J=10.6 Hz), 4.23–4.11 (m, 2H), 4.02–3.29 (m, 31H), 2.06 (s, 3H, NAc), 1.31 (d, 3H, J=6.6 Hz, CH$_3$ fucose, 1.29 (d, 3H, J=6.6 Hz, CH$_3$ fucose); $^{13}$C NMR (CD$_3$OD): δ173.20 (C=O), 135.73 (CH$_2$CH=CH$_2$), 105.13, 103.30, 102.49, 101.62, 99.63, 96.86, 80.79, 80.67, 78.44, 76.67, 76.49, 75.89, 74.80, 74.59, 73.94, 73.61, 73.40, 71.55, 71.38, 71.16, 70.42, 70.26, 70.14, 67.77, 67.30, 67.21, 62.79, 62.34, 61.99, 55.54, 22.97 (NAc), 16.65 (2 C's, C$_6$ fucose); IR (thin film): 3376.6 (OH), 2924.2, 1652.5 (C=O), 1383.1, 1032.4; $[\alpha]_{D23}=-12.8°$ (c 0.25, MeOH); HRMS (FAB): calcd. for $C_{41}H_{69}NNaO_{29}$: m/z=1062.3853, found 1062.3837

Figure 8A:
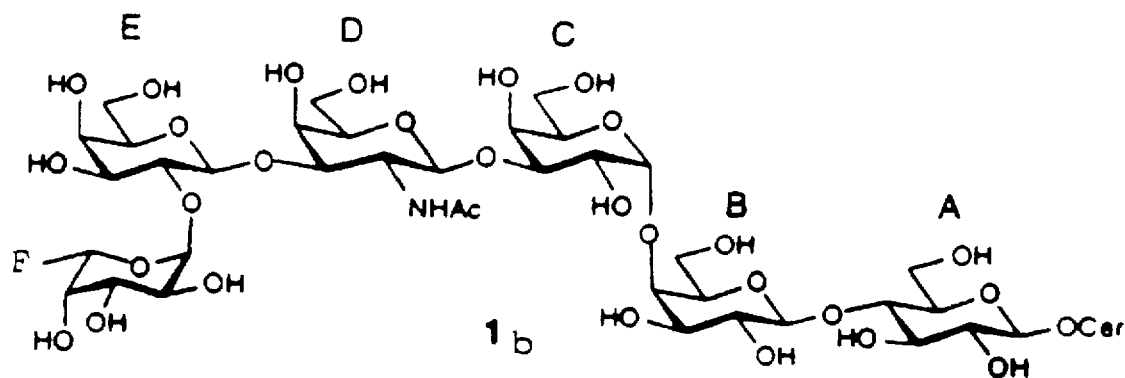
FIGS. 8a and 8b show the structure of the MBr1 antigen and a reaction pathway to a trisaccharide intermediate. Reagents: a. n-Bu$_2$SnO, PMBCl, TBABr, PhH, 70%; b. NaH, BnBr, DMF, 95%; c. (i) 3,3-dimethyldioxirane, CH$_2$Cl$_2$; (ii) TBAF, THF; (iii) NaH, BnBr, DMF, 40% (three steps); d. NaH, BnBr, DMF, 80%; e. (i) TBAF, THF; (ii) NaOMe, MeOH, 93% (two steps); f. (n-Bu$_3$Sn)$_2$O, BnBr, TBABr, PhH, 90%; g. SnCl$_2$, AgClO$_4$, 2,6-di-butylpyridine, 4 Å mol. sieves, Et$_2$O, 40% α' (4.5:1 α':B); h. DDQ, CH$_2$Cl$_2$, H$_2$O, 84%.
Figure 8B:
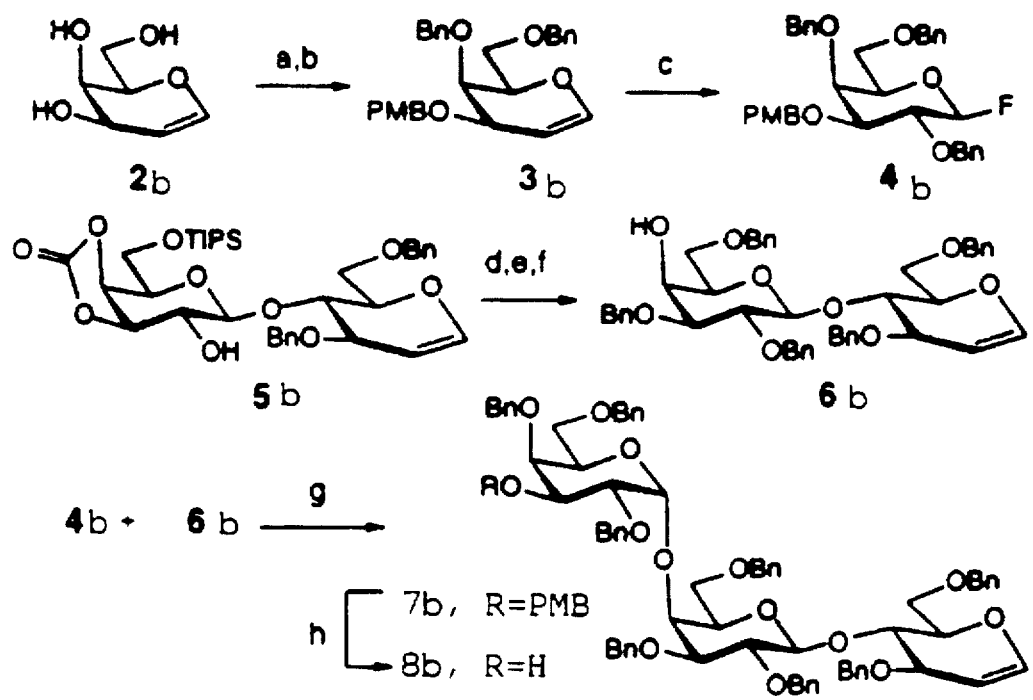

Glycal Assembly Method Applied to the Synthesis of Human Breast Tumor-Associated Antigen The present invention provides a convergent synthesis of the hexasaccharide wherein the two trisaccharide domains have been efficiently assembled in forms readily ammenable for coupling. The synthesis of the ABC trisaccharide is presented in FIG. 8. The α-linkage of this trisaccharide might be formed by employing a fluorosugar donor 4b, using established conditions. (Gordon, D. M.; Danishefsky, S. J., *Carbohydr. Res.*, 1990, 206, 361–366.) Preparation of the appropriate disaccharide acceptor commenced with 5b (Danishefsky, S. J.; Behar, V.; Randolph, J. T.; Lloyd, K. O., *J. Am. Chem. Soc.*, 1995, 0000), itself obtained from a glycal coupling. Benzylation followed by desilylation, carbonate removal and selective dibenzylation afforded the disaccharride 6b. The acceptor thus obtained was reacted with the fluorosugar 4b using modified Mukaiyama conditions (Mukaiyama, T.; Murai, Y.; Shoda, S., *Chem. Lett.*, 1981, 431–433) to provide the trisaccharide glycal 7b. Deprotection of the PMB ether provided the ABC trisaccharide 8b, which was poised for coupling with a suitable DEF trisaccharide donor.

Figure 9:
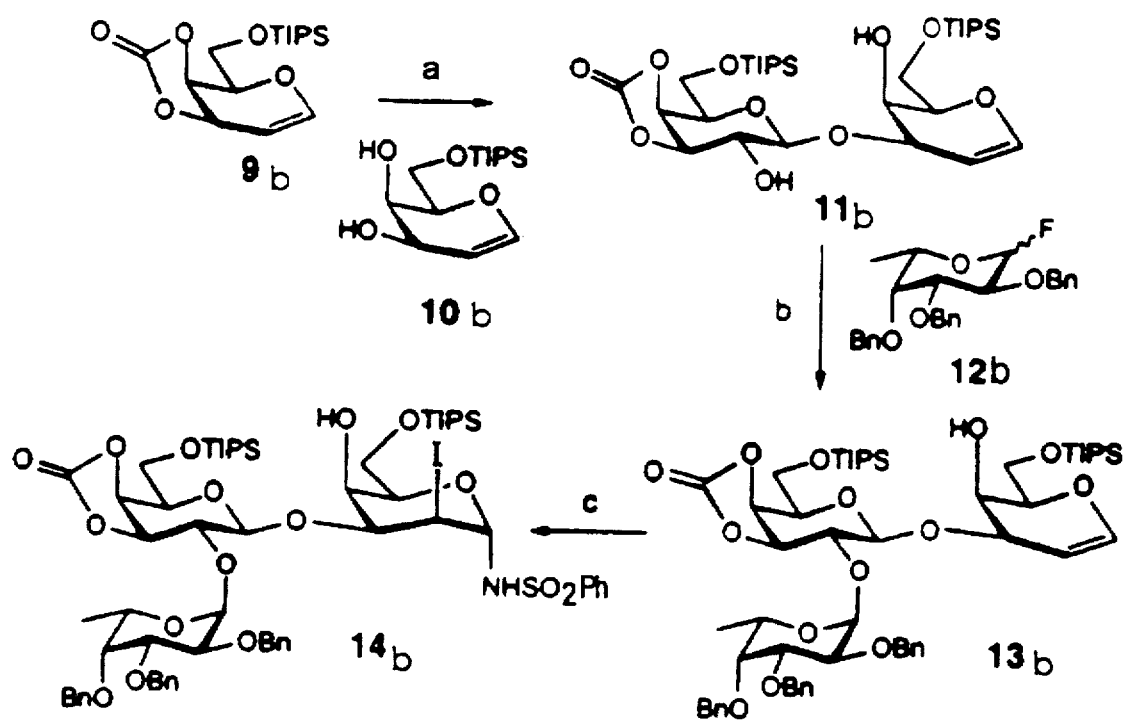
FIG. 9 shows a reaction pathway to a trisaccharide intermediate. Reagents: a. (i) 3,3-dimethyldioxirane, CH$_2$Cl$_2$; (ii) 10a, ZnCl$_2$, THF, 87%; b. SnCl$_2$, AgClO$_4$, Et$_2$O, 47%; c. I(coll)$_2$ClO$_4$, PhSO$_2$NH$_2$, 4 Å mol. sieves, 47%.

The synthesis of the DEF trisaccharide is described in FIG. 9. Epoxidation of the galactal 9b and standard coupling (Halcomb, R. L.; Danishefsky, S. J., *J. Am. Chem. Soc.*, 1989, 111, 6661–6666.) with acceptor 10b afforded, regioselectively, the disaccharide 11b. Fucosylation employing the fluoro-fucose 12b (Dejter-Juszynski, M.; Flowers, H. M., *Carbohydr. Res.*, 1973, 28, 61) provided a 5:1 ratio of monoglycosylation regioisomers, the major isomer being the desired trisaccharide 13b. This material was treated under standard conditions to afford the trans-diaxial iodosulfonamide 14b.

Figure 10A:
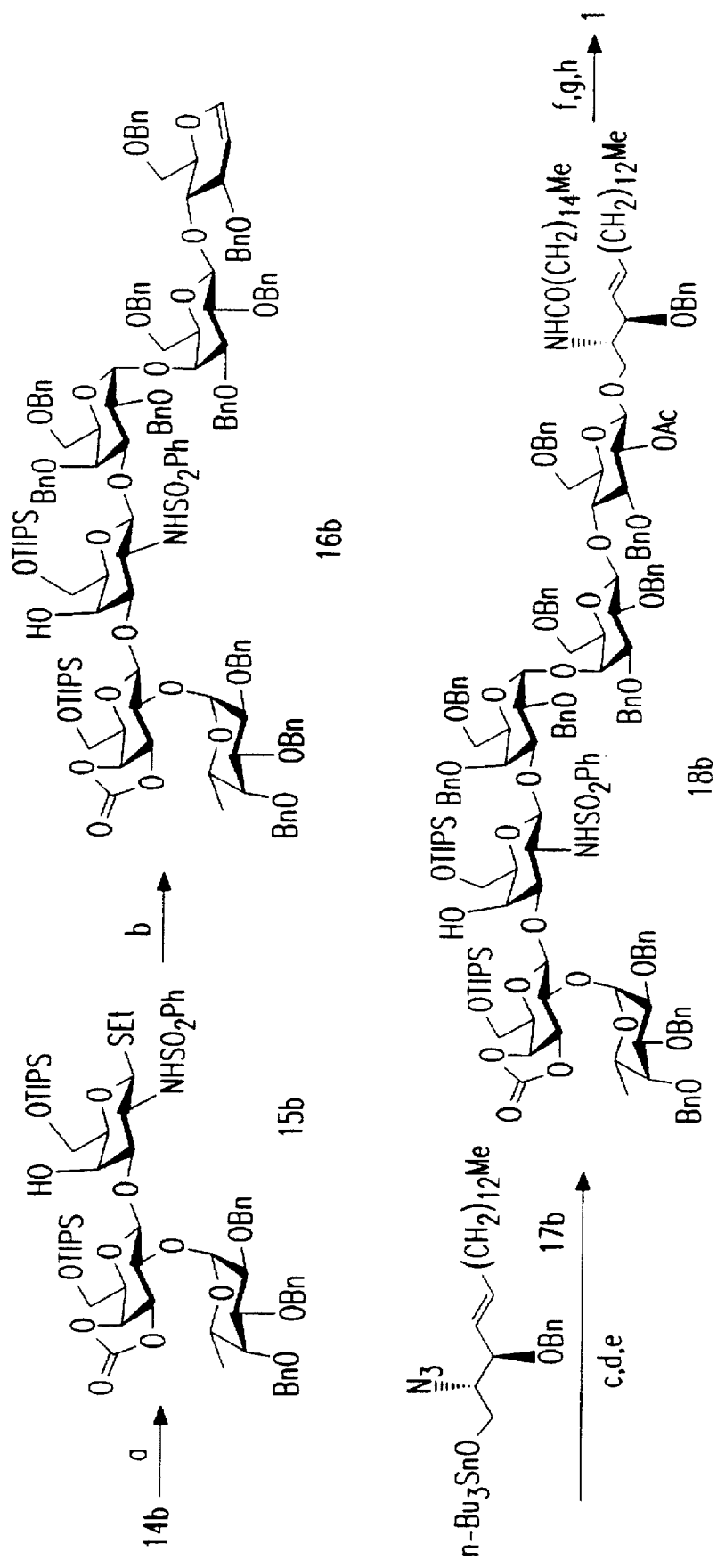
FIG. 10(a) shows a reaction pathway to the hexasaccharide MBr1 antigen. Reagents: a. EtSH, LiHMDS, DMF, 75%. B. 8b (0.5 equiv), MeOTf, 4 Å Mol. sieves, 70–85% B, (10:1 B α'); c. (i) 3,3-dimethyldioxirane, CH$_2$Cl$_2$ (ii) 17b (5 equiv), Zn(OTf)$_2$, 20%; d. Ac$_2$O, Et$_3$N, DMAP, CH$_2$Cl$_2$ 95%; e. Lindlar's cat., H$_2$ palmitic anhydride, EtOAc, 90%; f. (i) TBAF, THF; (ii) NaOMe, MeOH, 94%; g. (i) Na, NH$_3$, THF; (ii) Ac$_2$O, Et$_3$N, DMAP, CH$_2$Cl$_2$, 80% h. NaOMe, MeOH, quant.
Figure 10B:
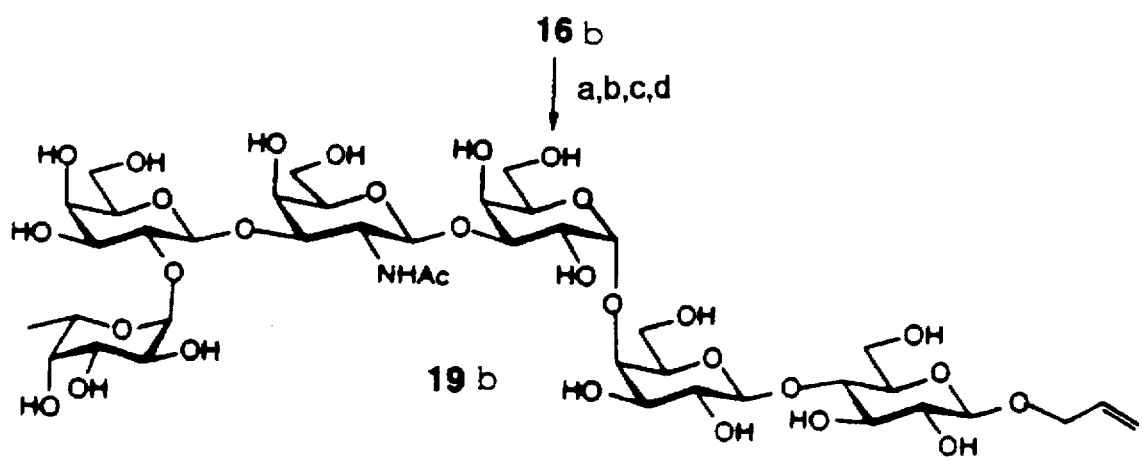
FIG. 10(b) shows a reaction pathway to the allyl glycoside. Reagents: a. TBAF, THF, 94%; b. (i) Na, NH$_3$, THF; (ii) Ac$_2$O, Et$_3$N, DMAP, THF, DMF, 85%; c. (i) 3,3-dimethyldioxirane, CH$_2$Cl$_2$, (ii) allyl alcohol, 65% (+29% of α'-manno isomer); d. NaOMe, MeOH, quant.

Direct coupling reactions (Griffith, D. A.; Danshefsky, S. J., *J. Am. Chem. Soc.*, 1990, 112, 5811–5819; Danishefsky, S. J.; Koseki, K.; Griffith, D. A.; Gervay, J.; Peterson, J. M.; McDonald, F. E.; Oriyama, T., *J. Am. Chem. Soc.*, 1992, 114, 8331–8333) employing iodosulfonamides such as 14b with ABC trisaccharide acceptors failed, leading to a different donor functionality in the trisaccharide. In practice, the iodosulfonamide 14b was treated with excess lithium ethanethiolate to afford the ethyl thioglycoside 15b (FIG. 10). Precedent established by the present inventors lead to the prediction of sulfonamide participation to provide the desired β-linked product from 15b. (Griffith, D. A., Ph.D. Thesis, Yale University, 1992) When donor 15b was treated with MeOTf in the presence of acceptor 8b, a 10:1 mixture of hexasaccharide isomers was obtained. The major product 16b was obtained in 70–85% yield.

Ceramide attachment and elaboration commenced with epoxidation of 16b, followed by reaction with the stannyl ether 17b promoted by $Zn(OTf)_2$. (Liu, K. K.-C.; Danishefsky, S. J., *J. Am. Chem. Soc.*, 1993, 115, 4933–4934) Although the yield of this ceramide coupling is low, when this reaction was performed on trisaccharide 7b, the corresponding product was obtained in 66% yield. This material can then be used to obtain 18b. Following acetylation, the ceramide side-chain was elaborated by reduction of the azide functionality using Lindlar's catalyst under an atmosphere of $H_2$ in the presence of palmitic anhydride to provide 18b. Desilylation and saponification was followed by dissolving metal deprotection and MeOH quench. Peracetylation of the crude mixture, followed by saponification provided the glycosphingolipid 1b. Only the chemical shifts and coupling constants of the anomeric protons have been reported for the natural material. The spectrum of synthetic 1b is in complete agreement with this data. Furthermore, the product was characterized by exact mass, and $^1$H and $^{13}$C NMR. The synthetic material has also been shown to bind to the monoclonal antibody MBr1.

Figure 11A:
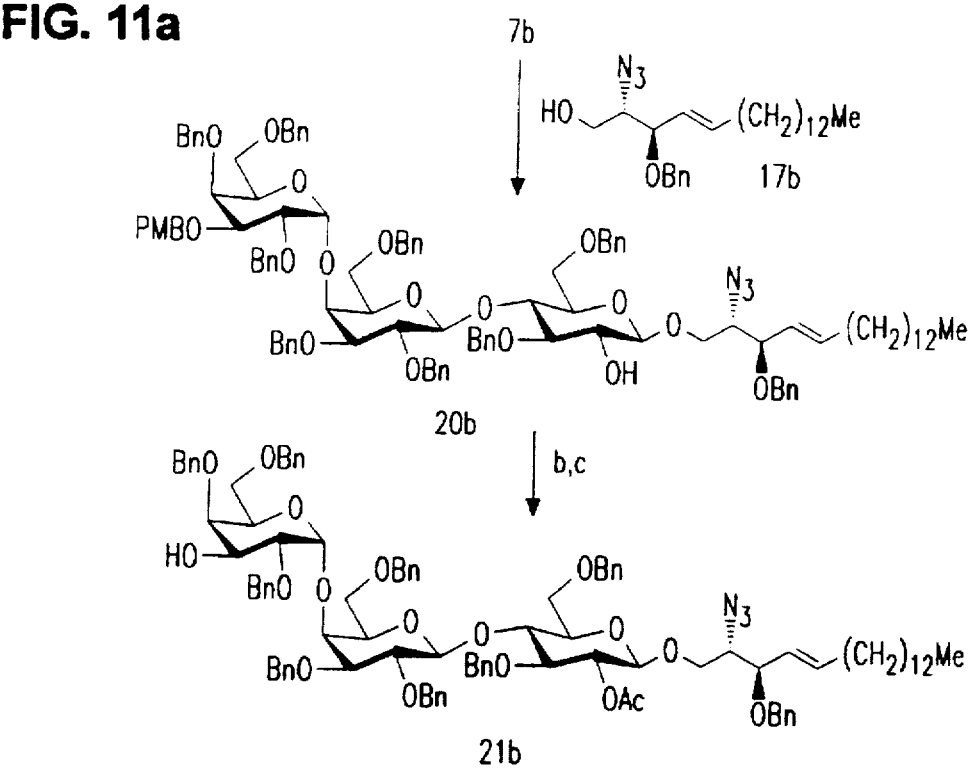
FIGS. 11a and 11b show a reaction pathway to intermediates for preparing the hexasaccharide antigen MBr1.
Figure 11B:
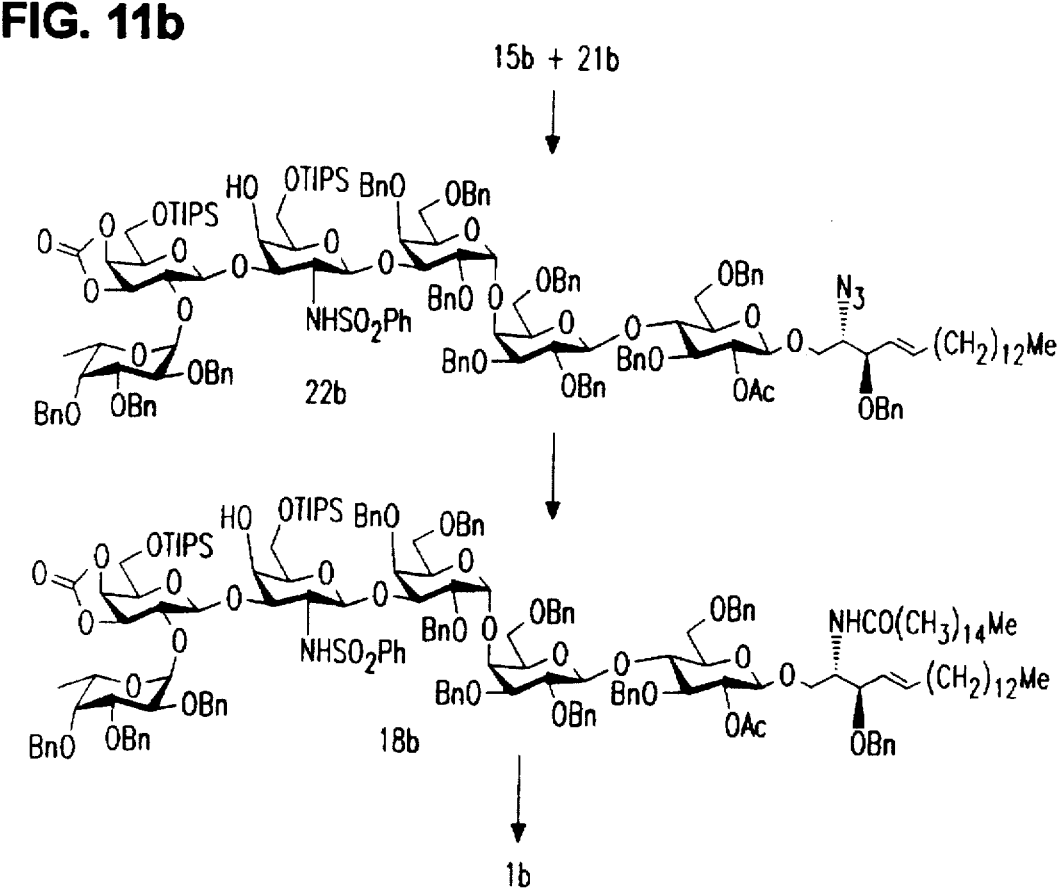

In addition, the present invention provides the corresponding allyl glycoside (FIGS. 11a and 11b). Deprotection of 16b, as above, and acetylation afforded the peracetate of the hexasaccharide glycal. Epoxidation, reaction with allyl alcohol, and saponification provided the allyl glycoside 19b.

As in the case of the Le determinant, ozonolysis of the allyl group of 19b will set the stage for reductive coupling to lysine residues of proteins.

Synthesis of 3b 3-0-(4-Methoxybenzyl)-D-galactal

A suspension of D-galactal (2b) (3.70 g, 25.3 mmol) and dibutyltin oxide (6.30 g, 1.0 equiv) in dry benzene (150 mL) was heated to reflux for 2 h with azeotropic removal of water. The reaction was cooled and treated with PMBCl (3.80 mL, 1.1 equiv) and tetrabutylammonium bromide (9.10 g, 1.1 equiv) and refluxed for 4 h. The reaction was filtered through silica column and eluted with EtOAc/hexanes (4:1). Fractions containing product were concentrated and the residue triturated in hexanes to give 4.50 g (67%) of product as white crystalline solid.

mp (hexanes) 117°–118° C.; $(a)^{23}=-23.0°$ ($CHCl_3$, c=1.1); IR (KBr) 3313 (br), 1645, 1513, 1228, 1082, 821 cm$^{-1}$ H-NMR (400 MHz, $CDCl_3$) δ7.28 (2H, d, J=8.4 Hz), 6.89 (2H, d, J=8.4 Hz), 6.44 (1H, dd, J=6.4 Hz), 4.70 (1H, dt, J=6.3, 1.9 Hz), 4.59–4.52 (2H, ABq, J=11.4 Hz), 4.20–4.18 (1H, m), 4.04–3.97 (1H, m), 3.90–3.82 (2H, m), 3.81 (3H, s), 2.73 (1H, d, J=3.1 Hz, C4-OH), 2.54 (1H, dd, J=8.2, 4.2 Hz, C6-OH); $^{13}$C-NMR (100 MHz, $CDCl_3$) δ159.46, 145.02, 142.05, 129.46, 113.95, 99.36, 76.12, 70.17, 70.14, 63.65, 62.74, 55.26; LRMS($NH_3$) 284 $(M+NH_4)^+$, 266 $(M)^+$, 249.

4,6-di-O-benzyl-3-0-(4-methoxybenzyl)-D-galactal (3b)

A solution of 3-0-(4-methoxybenzyl)-D-galactal (2.28 g, 8.56 mmol) and benzyl bromide (3.75 mL, 3.68 mol equiv; freshly passed through basic alumina) in DMF (30 mL) under $N^2$ at 0° C. was treated with NaH (1.37 g, 4.0 mol equiv) in two portions. The reaction was stirred 0.5 h at 0° C. and 1 h at rt. The reaction was carefully poured into 50 g of crushed ice, diluted to 100 mL with water, then extracted with EtOAc-hexanes (1:1, 100 mL×3). Organic extracts were washed with water (100mL×2), dried ($Na^2SO^4$) and concentrated. Flash chromatography with 15% EtOAc-hexanes gave 3.58 g (94%) of the title compound as a clear liquid.

$[\alpha]^{23}_D=-48.2°$ ($CHCl_3$, c=0.85); IR (neat) 3030, 2867, 1645, 1613, 1513 1247, 1092, 821, 736 cm$^{-1}$; $^1$H-NMR (400 MHz, $CDCl_3$) δ7.34–7.23(12H, m), 4.62 (1H, d, J=12.0 Hz), 4.59–4.51 (2H, ABq, J=11.7 Hz), 4.50–4.39 (2H, ABq, J=11.9 Hz) $^{13}$C-NMR (100 MHz, $CDCl_3$) δ159.04, 143.99, 138.30, 137.90, 130.43, 128.26, 128.20, 128.03, 127.77, 127.57, 127.56, 113.67, 100.00, 75.58, 73.28, 73.17, 71.13, 70.42, 70.28, 68.35, 55.15; LRMS ($NH_3$) 464 $(M+NH^{4+}$, 100), 326 (18), 309 (48), 253 (17).

Synthesis of 4b

A solution of galactal 3b (3.20 g, 7.17 mmol) in dry $CH_2Cl_2$ under $N_2$ at 0° C. was treated with dimethyldioxirane (0.09M, 80 mL) and stirred until all of the glycal was consumed (0.5–1 h; TLC 30% EtOAc in hexanes). Volatiles were removed at 0° C. with stream of dry $N_2$. The residue was dissolved in 30 mL of dry THF under $N_2$ at 0° C. and treated TBAF (36 mL, stored over molecular sieves) then stirred at ambient temperature for 20 h. The dark brown solution was filtered through a pad of silica (~4 cm depth) and washed with EtOAc (200 mL). The filtrate was washed with water (200 mL×3) and dried (MgSO$_4$) and concentrated. The residue was redissolved in 30% EtOAc-hexanes (50 mL) and filtered through short silica column (10 cm d×4 cm h) and washed with the same solvent system (1 L). The filtrate was concentrated to give 2.59 g of fluorohydrin with >90% purity. The residue was dissolved in dry DMF (30 mL) under N$_2$ at 0° C. and treated with benzyl bromide (958 uL, 1.5 equiv, freshly filtered through basic alumina), finally with NaH (322 mg, 60% dispersion, 1.5 equiv) and stirred for 30 min at 0° C. and 30 min at rt. The reaction was quenched by pouring into 100 g of ice, and extracted with 1:1 EtOAc-hexanes (150 mL×2). The organic extracts were washed with water (150 mL×2), dried (MgSO$_4$) and concentrated in vacuo. Flash chromatography with 10% EtOAc-hexanes gave 2.00 g (49%) of the title compound as a yellowish liquid.

$[\alpha]^{23}_D$=+15.3° (CHCl$_3$, c=0.85); IR (CHCl$_3$ film) 2916, 1612, 1513, 1248, 1103, 1056, 734 cm$^{-1}$; $^1$H-NMR (400 MHz, CDCl$_3$) δ7.35–7.24 (17H, m), 6.84 (2H, d, J=8.4 Hz), 5.15 (1H, dd, J=53.2, 7.0 Hz), 4.92 (1 Hz, d, J=11.6 Hz), 4.48–4.74 (2H, ABq, J=11.8 Hz), 3.96–3.89 (1H, m), 3.86 (1H, br s), (3H, s), 3.65–3.56 (3H, m), 3.51 (1H, dd, J=9.8, 2.8 Hz); $^{13}$C-NMR (100 MHz, CDCl$_3$) δ159.22, 138.33, 138.11, 137.62, 130.16, 129.19, 128.40, 128.29, 128.21, 128.04 (2C), 127.90, 127.81, 127.69, 127.59, 113.77, 110.20 (d, J=214 Hz), 80.60 (d, J=11.3 Hz), 79.00 (d, J=20.5 Hz), 74.92, 74.52, 73.59 (d, J=5.0 Hz), 73.54, 72.99, 72.70, 68.34, 55.20; LRMS (NH$_3$) 454 (M+NH$_4^+$, 100).

Synthesis of 6b

A solution of TIPS-carbonate galactal 5b (Danishefsky, S. J.; Behar, V.; Randolph, J. T.; Lloyd, K., *J. Am. Chem. Soc.*, 1995, 0000) (4.28 g, 5.62 mmol) in THF (25 mL)-MeOH (5 mL) was treated with TBAF solution (1.0M, 6.75 mL, 1.2 equiv). After 6 h, additional TBAF (4 mL) was added and stirred additional 3 h. The reaction was concentrated and directly chromatographed with 4:1 EtOAc-hexanes to obtain 2.20 g of the triol. Remaining mixtures of cyclic carbonate and mixed carbonate was hydrolysed in MeOH with MeONa (1.0 mL, 25 wt %) and purified chromatographically. Total yield was 3.02 g (93%). This material was directly used for the dibenzylation step.

$^1$H-NMR (400 MHz, CDCl$_3$) δ7.35–7.24 (15H, m), 6.43 (1H, d, J=6.3 Hz), 4.87 (1H, dd, J=6.3, 3.4 Hz), 4.84 (1H, d, J=11.4 Hz), 4.63 (2H, apparent s), 4.61 (1H, d, J=11.4 Hz), 4.53–4.47 (3H, m), 4.19–4.16 (3H, m),3.87–3.84 (2H,m), 3.78–3.66 (3H, m), 3.46 (2H, apparent d, J=4.6 Hz), 3.29 (1H, t, J=5.5 Hz), 3.08 (1H, br), 2.73 (2H, br); $^{13}$C-NMR (100 MHz, CDCl$_3$) δ144.70, 138.41, 138.22, 137.83, 128.45, 128.33 (2C), 128.12, 127.84, 127.73, 127.64, 127.57, 102.28, 99.74, 78.99, 76.03, 74.64, 74.07, 73.24 (2C), 73.17, 72.64, 70.20, 69.10, 67.79, 62.15.

A mixture of triol glycal from above (2.95 g, 5.1 mmol), dibutyltin oxide (1.33 g, 1.05 equiv) and bistributyltin oxide (1.69 mL, 0.65 equiv) in dry benzene (50 mL) under N$_2$ was refluxed for 5 h with azeotropic removal of water. The reaction was cooled below boiling and treated with benzyl bromide (2.43 mL, 4.0 mol equiv) and tetrabutylammonium bromide (3.29 g, 2.0 equiv). 10 mL of benzene was distilled off and the reaction refluxed for 16 h. The reaction was directly loaded on silica column and eluted with 15–20% EtOAc-hexanes to give 3.48 g (90%) of product 6b as a clear oil.

$[\alpha]^{23}_D$=−3.3° (CHCl$_3$, c=0.87); IR (CHCl$_3$ film) 2867, 1652 1454, 1364, 1097, 736 cm$^{-1}$; $^1$H-MNR (400 MHz, CDCl$_3$) δ7.35–7.21 (25H, m), 6.45 (1H, d, J=6.2 Hz), 4.88 (1H, dd, J=6.2, 3.9 Hz), 4.83 (1H, d, J=10.9 Hz), 4.69 (2H, apparent s), 4.68 (1H, d, J=10.9 Hz), 4.59 (2H, apparent s), 4.55 (1H, d, J=7.8 Hz), 4.49 (2H, apparent s), 4.47 (2H, apparent s), 4.29 (1H, dd, J=9.6, 5.8 Hz), 4.18 (1H, t, J=4.4 Hz), 4.13 (1H, m), 3.99 (1H, br s), 3.85 (1H, dd, J=10.6, 6.4 Hz), 3.75–3.60 (4H, m), 3.47–3.41 (2H, m); $^{13}$C-NMR (100 MHz, CDCl$_3$) δ144.43, 138.64, 138.42, 137.99, 137.84, 137.80, 128.40, 128.34, 128.26, 128.23, 128.18, 128.15, 127.82, 127.75, 127.69, 127.67, 127.65, 127.55, 127.51, 127.46, 127.31102.56, 99.56, 80.57, 78.69, 75.72, 75.10, 73.57, 73.32, 72.94, 72.28, 71.94, 70.12, 68.90, 67.85, 66.62; LRMS (NH$_3$) 776 (M+NH$_4^+$, 100).

Synthesis of 7b

Lactal 6b (1.32 g, 1.74 mmol, 1.0 equiv) and fluoro sugar 4b (1.49 g, 2.60 mmol, 1.5 equiv) were combined in ether and concentrated. The mixture were dried by evaporation in dry benzene (25 mL×2), in vacuum for 2 h then treated with di-t-butylpyridine (389 uL, 1.0 equiv) in glove bag and dissolved in dry ether (18 mL) under nitrogen atmosphere. In a separate 50 mL flask was placed 4A M.S. (4.0 g) then flame-dried under vacuum, cooled to room temperature. Anhydrous silver perchlorate (360 mg, 1.0 equiv) and SnCl$_2$ (329 mg, 1.0 equiv) were added in glove bag and flushed with nitrogen. The salt mixture was placed in water bath and sugar solution was introduced via double tipped needle and the mixture sonicated for 2 min. The reaction was wrapped with aluminum foil and stirred for 45 h at rt. The filtrate (200 mL) was washed with dil NaHCO3 (100 mL×2), dried (MgSO$_4$) and concentrated. Flash chromatography with 15–20% EtOAc/hexanes yielded trisaccharides (1.107 g, 49%) and impure lactal. The trisaccharide portion was rechromatographed with 2% ether-methylene chloride to give 879 mg (39%) of the desired α-product and 195 mg (8.6%) of β-product. The impure lactal fraction was rechromatographed with 3–4% ether-methylene chloride to give 479 mg (36%) of clean lactal. 77% of coupling (61% α-product) yield based on recovered starting material.

$[\alpha']^{23}_D$=+41.8° (CHCl$_3$, c=1.8); IR (CHCl$_3$ film) 2867, 1648, 1513, 1496, 1453, 1364, 1248, 1097, 735 cm$^{-1}$; $^1$H-NMR (400 MHz, CDCl$_3$) δ7.33–7.12 (42H, m) 6.83 (2H, d, J=8.4 Hz), 6.45 (1H, d, J=6.0 Hz), 5.03 (1H, d, J=2.3 Hz), 4.91–4.76 (6H, m), 4.68–4.40 (12H, m), 4.23–3.97 (11H, m), 3.86–3.82 (1H, dd, J=2.3 Hz), 3.76 (3H, s), 3.69–3.64 (2H, m), 3.53 (1H, t, J=8.7 Hz), 3.47–3.43 (1H, m), 3.40–3.36 (1H, m), 3.34–3.31 (1H, dd, J=9.9, 2.8 Hz), 3.22 (1H, dd, J=8.3, 4.8 Hz); $^{13}$C-NMR (100 MHz, CDCl$_3$) δ158.93, 144.59, 138.98, 138.84, 138.78, 138.64, 138.58, 138.06, 138.02 (2C), 130.82, 129.04, 128.33, 128.24, 128.21, 128.15, 128.08, 128.05, 127.83, 127.81, 127.72, 127.64, 127.58, 127.55, 127.50, 127.44, 127.41, 127.36, 127.33, 127.31, 113.65, 103.02, 100.39, 100.01, 80.93, 78.93, 78.70, 76.53, 76.11, 75.14, 74.84, 74.79, 74.35, 73.91, 73.59, 73.36, 73.15, 73.10, 72.98, 72.15, 72.10, 71.99, 70.55, 69.25, 67.92 (2C), 67.69, 55.19.

Synthesis of 8b

A solution of PMB-trisaccharide (37 mg, 0.028 mmol) in CH$_2$Cl$_2$ (1 mL) at 0° C. The reaction was directly loaded on silica column and eluted with 20% EtOAc-hexanes to give 28 mg (84%) of desired product.

$[\alpha']^{23}_D$=+45.6° (CHCl$_3$, c=1.78); IR (CHCl$_3$ film) 2866, 1648, 1496, 1453, 1248, 1097, 735 cm$^{-1}$; $^1$H-NMR (400 MHz, CDCl$_3$) δ7.36–7.15 (40H, M), 6.43 (1H, d, J=6.2 Hz), 5.09 (1H, d, J=3.3 Hz), 4.85 (1H, dd, J=6.2, 3.6 Hz), 4.83–4.65 (5H, m), 4.61–4.41 (9H, m), 4.29–4.08 (8H, m), 4.02 (1H, d, J=2.6 Hz), 3.97 (1H, d, J=2.2 Hz), 3.93 (1H, t, J=8.4 Hz), 3.86–3.78 (2H, m), 3.67–3.61 (2H, m), 3.53 (1H, dd, J=8.5, 4.8 Hz); $^{13}$C-NMR (100 MHz, CDCl$_3$) δ144.38, 138.78, 138.62, 138.47, (2C), 138.20, 138.00, 137.88, (2C, 128.31, 128.29, 128.23, 128.19, 128.16, 128.05, 127.88, 127.83, 127.62, 127.57, 127.49, 127.45, 127.43, 127.41, 127.37, 127.32, 127.23, 102.68, 99.89, 99.34, 80.82, 78.72, 77.49, 77.10, 75.88, 75.13, 75.03, 74.23, 73.62, 73.05, 73.01, (3C), 72.62, 72.19 (2C), 70.46, 69.66, 68.92, 67.85, 67.74, 67.54.

Synthesis of 11b

Glycal 9b (4.32 g, 3.14 mmol) was dissolved in CH$_2$Cl$_2$ (20 ml) and cooled to 0° C. It was then treated with dimethyldioxarane (219 ml, ¯3.14 mmol) at 0° C. The epoxidation finished within 1 h and then the reaction mixture was concentrated to dryness using dry N$_2$ stream. The residue was further azeotroped once with benzene (20 ml) and put on a vacuum line for 30 min at 0° C. before being dissolved in THF (60 ml) and cooled to −78° C. Into the above solution was added, via canula, azeotropically dried galactal 10b (3.32 g, 10.95 mmol, 20 ml THF) and followed by ZnCl$_2$ (26.3 ml, 1.0M in ether). The reaction mixture was warmed up to room temperature and stirred overnight. After treatment with sat'd aq. Na$_2$CO$_3$ (40 ml), the reaction mixture was concentrated and extracted with ether (500 ml). The organic phase was washed with sat'd aq. NaCl, dried (MgSO$_4$) and concentrated. The crude product was purified by silica gel chromatography (1:4 EtOAc-hexanes) to give 6.20 g of 11b as a white foam (87.4%).

IR (CH$_3$ film) xyz cm$^{-1}$; $^1$H-NMR (400 MHz, CDCl$_3$) δ6.45 (1H, dd, J=6.4, 1.6 Hz), 4.85 (1H, dd, J=6.4, 2.0 Hz), 4.72–4.68 (2H, m), 4.65 (1H, d, J=7.2 Hz), 4.55 (1H, m), 4.21 (1H, m), 4.08 (1H, dd, J=9.6, 5.6 Hz), 3.96–3.82(6H, m), 3.33 (1H, d, J=3.2 Hz, OH), 3.27 (1H, d, J=2.8 Hz, OH), 1.16–1.04 (42H, m); $^{13}$C-NMR (100 MHz, CDCl$_3$) δ154.45, 145.75, 99.14, 98.27, 77.83, 76.59, 74.27, 72.04, 71.62, 70.86, 64.52, 62.57, 61.60, 17.84, 11.78, 11.77.; LRMS (NH$_3$) 664 (M+NH$_4^+$, 100), 647 (M+1$^+$, 5), 422 (21), 380 (25).

Synthesis of 13b

Disaccharide 11b (2.64 g, 4.08 mmol) was azeotropically dried three times (3×10 ml) together with fluoro-fucose 12b (1.64 g, 3.77 mmol) and molecular sieves (4A, 4.0 g) in THF (20 ml) with 2,6-di-tert-butypyridine. The solution was added via canula to a flask containing AgClO$_4$ (1.56 g, 7.54 mmol), SnCl$_2$ (1.43 g, 7.54 mmol) and molecular sieves (4 A, 4.0 g) in THF (15 ml) at −40° C. The reaction mixture was stirred 30 min at −40° C. and then 34 h at 5° C. until the disappearance of fluoro-fucose. After treatment with sat'd aq. NaHCO$_3$ (40 ml) at 50° C., the mixture was extracted with EtOAc (700 ml). The organic phase was washed with sat'd NaCl, dried (MgSO$_4$) and concentrated. The crude product was purified by silica gel chromatography to give 1.93 g of the desired trisaccharide glycal 13b (48%, based on fluoro-fucose used) and 500 mg of the recovered disaccharide with only a trace of the other monofucosyl product.

Synthesis of 15b

An azeotrapically dried mixture of the trisaccharide glycal 13b (1.11 g, 1.05 mmol) and benzensulphonamide (0.82 g, 5.24 mmol) was dissolved in the THF (20 ml) together with molecular shieves (4 A, 2.6 g). The mixture was cooled to −40° C. and then was added, via canula, a solution of I(sym-coll)$_2$COl$_4$ prepared in situ by stirring I$_2$ (0.54 g, 2.09 mmol) with Ag(sym-coll)$_2$COl$_4$ (0.986 g, 2.29 mmol) in THF (20 ml) at room temperature for about 30 min until the disappearance of the brown color of I$_2$. The mixture was warmed up to 0° C. within 1 h and stirred for another 1 h. After quenching with sat'd aq. Na$_2$S$_2$O$_3$, the mixture was filtrate and extracted with EtOAc (3×100 ml). The combined organic phase was washed with sat'd aq. CuSO4 (100 ml), sat'd NaCl (100 ml×2) and dried (Na$_2$SO$_4$). After concentration, the crude product was purified by silica gel chromatography (1:4 EtOAc-hexanes) to give 981 mg of a colorless oil as a 21 mixture of the desired α'-trans-diaxial iodosulphonamide and its cis isomer. The iodosulphonamide mixture was then added with stirring into a flask containing ethanthiol (226.3 mg, 3.64 mmol) and lithium hexamethydisilylazide (1.46 ml, 1.46 mmol) in DMF (10 ml) at −40° C. The reaction mixture was stirred at −40° C. overnight, and then quenched with sat'd aq. NaHCO$_3$ and extracted with ether)3×100 ml). The combined organic phase was washed with sat'd aq. NaCl and dried (Na$_2$SO$_4$). After concentration, the crude product was purified by silica gel chromatography (3:97 EtOAc-CHCl2) to yield 438 mg of 15b (33%) and 333 mg of the intact cis iodosulphonamide.

Synthesis of 16b

A mixture of acceptor trisaccharide 8b (92 mg, 0.077 mmol, 1.0 equiv), thiogycoside 15b (198 mg, 2.0 equiv) and freshly activated 4 Å-MS (560 mg) under N$_2$ at rt was suspended in CH$_2$Cl$_2$-Et$_2$O (1:2, 3.9 mL) and stirred for 10 min. The reaction was cooled to 0° C., then treated with methyl triflate (52.4 uL, 6.0 equiv). The reaction was stirred for 4.5 h at 0° C. and 1.5 h while warming to 15° C. The reaction was quenched with TEA (1.0 mL), filtered through a pad of silica and rinsed with Et$_2$O. The filtrate (70 mL) was washed with sat'd NaHCO$_3$ (50 mL×2), dried (Na$_2$SO$_4$) and concentrated. The crude product was purified by HPLC (17% EtOAc in hexanes, 15 mL/min, 260 nm UV dection) to give 158 mg (85%) of the desired product and 27.7 mg of α'-linked byproduct (ca 55% purity).

Retention time=22 min; $[\alpha']^{23}_D$=−13.3° (CHCl$_3$, c=1.4); IR (CHCl$_3$ film) 2940, 2865, 1792, 1652, 1454, 1161, 1101, 734 cm$^{-1}$; $^1$H-NMR (400 MHz, CDCl$_3$) δ7.8 (2H, m), 7.38–7.06 (58H, m), 6.43 (1H, d, J=6.1 Hz), 5.15 (1H, br s), 5.07 (1H, d, J=3.6 Hz), 5.03 (1H, d, J=3.6 Hz), 4.99 (1H, d, J=11.6 Hz), 4.89–4.61 (12H, m), 4.54–4.46 (4H, m), 4.42 (2H, app s), 4.38 (1H, d, J=11.9 Hz), 4.34–4.26 (3H, m), 4.21–4.18 (4H, m), 4.13–4.03 (7H, m), 3.98–3.76 (14H, m), 3.70–3.61 (4H, m), 3.46–3.27 (7H, m), 2.84 (1H, OH), 1.16 (3H, d, J=6.4 Hz), 1.13–1.02 (42H, m); $^{13}$C-NMR (100 MHz, CDCl$_3$) δ155.35, 144.55, 140.78, 138.99, 138.75, 138.68, xxx, 138.54, 138.43, 138.13, 138.03, 137.94, 137.82, 132.31, 128.81, 128.52, xxx, 128.38, 128.36, 128.27, 128.24, 128.20, 128.16, 128.02, 127.93, 127.72, 127.66, 127.58, 127.48, 127.43, 127.37, 127.20, 103.41, 102.75, 99.79, 99.55, 98.29, 97.76, 80.49, 80.39, 79.09, 78.91, 78.25, 77.68, xxx, 76.51, 75.88, 75.09, 74.99, 74.91, 74.73, 74.15, 74.02, 73.92, 73.52, 73.19, 73.10, 72.94, 72.67, 72.25, 72.07, 71.76, 71.56, 71.33, 70.33, 69.45, 69.32, 68.48, 68.08, 67.86, 67.75, 61.97, 61.60, 56.14, 17.99, 17.96, 17.95, 17.92, 16.75, 11.86; HRMS (FAB) calcd for C$_{138}$H$_{169}$NO$_{30}$SSi$_2$Na (M+Na) 2432.0920, found 2432.0970.

Synthesis of 19b

A solution of hexasaccharide glycal 16b (85 mg, 0.035 mmol) in THF (6 mL) under N$_2$ at rt was treated with TBAF (1.0M, 353 uL, 10 equiv). After 38 h at rt, the reaction was concentrated to ca 1 mL, then dissolved in EtOAc (60 mL), washed with water (30 mL×2), dried (Na$_2$SO$_4$) and concentrated. Flash chromatography with 4% MeOH in CH$_2$Cl$_2$ gave 70.0 mg (98%) of the desilyl-decarbonated product.

$[\alpha']^{23}_D$=180° (CHCl$_3$ film) 2868, 1652, 1455, 1157, 1094, 735 cm$^{-1}$; $^1$H-NMR (400 MHz, CDCl$_3$) δ7.80 (2H, d, J=7.4 Hz), 7.47 (2H, d, J=7.2 Hz), 7.37–6.95 (56H, m), 6.45 (1H, d, J=6.3 Hz), 5.86 (1H, br s), 5.35 (1H, d, J=11.6 Hz), 5.30 (1H, D, J=2.8 Hz), 4.95 (1H, d, J=11.3 Hz), 4.89 (1H, d, J=3.5 Hz), 4.8644.67 (9H, m), 4.54–4.39 (9H, m), 4.34 (1H, dd, J=10.4, 2.8 Hz), 4.26–4.06 (9H, m), 3.98–3.45 (23H, m), 3.41 (1H, d, J=10.0 Hz), 3.29–3.20 (5H, m), 0.73 (3H, d, J=6.3 Hz); $^{13}$C-NMR (100 MHz, CDCl$_3$) $\delta$144.87, 142.49, 139.49, 139.11, 138.87, 138.63, 138.54, 138.37, 138.00, 137.98, 137.97, 137.18, 131.64, 128.74, 128.52, 128.43, 128.33, 128.28, 128.25, 128.21, 128.02, 127.99, 127.97, 127.80, 127074, 127.67, 127.63, 127.61, 127.54, 127.53, 127.50, 127.44, 127.33, 127.31, 127.02, 126.86, 103.39, 102.78, 100.75, 100.09, 99.80, 99.75, 81.42, 80.64, 78.98, 78.86, 77.82, 77.40, 77.26, 76.26, 75.16, 75.09, 75.07, 74.95, 74.69, 74.30, 73.58, 73.17, 73.11, 72.71, 72.67, 72.65, 72.55, 72.36, 72.18, 69.65, 69.53, 68.54, 68.18, 68.08, 67.85, 67.79, 67.21, 54.95, 16.60.

To liquid ammonia (ca 8 mL) under N$_2$ at −78° C. was added metallic sodium (95 mg) and stirred for 2 min. To the blue solution was added a solution of th hexasaccharide glycal above (70 gm, 33.8 umol) in dry THF (2 mL). After 45 min at 78° C., the reaction was quenched with absolute methanol (4 mL). Most of ammonia was removed with stream of nitrogen (final volume was ca 4 mL) and the reaction diluted with methanol to ca 10 mL. To the solution was added Dowex 50-X8 (890 mg, washed and dried) and stirred for 5 min. The solution was filterate and rinsed with methanol, finally with ammoniacal methanol (5 mL), and the filterate was concentrated in vacuo. The residue and DMAP (2.4 mg) were placed under N$_2$ and suspended in DMF (1.0 mL), THF (1.0 mL) and TEA (1.0 mL), then treated with Ac$_2$O (0.3 mL). After 20 h (TLC analysis with EtOAc), the reaction was poured into water (40 mL), and extracted with EtOAc (40 mL×2), washed with dil NaHCO$_3$ (30 mL), with water (30 mL), dried (Na$_2$SO$_4$) and concentrated. Flash chromatography with 80% EtOAc in CH$_2$Cl$_2$ gave 52.0 mg (93%) of product as white foam.

mp 132°–134° C.; [α']$^{23}_D$=+4.7° (CHCl$_3$, c=1.4); IR (CHCl$_3$ film) 1742, 1652, 1371, 1227, 1069 cm$^{-1}$; $^1$H-NMR (400 MHz, CDCl$_3$) $\delta$6.68 (1H, d, J=6.8 Hz), 6.42 (1H, d, J=6.0 Hz), 5.58 (1H, d, J=3.2 Hz), 5.47 (1H, d, J=3.4 Hz), 5.40–5.37 (2H, m), 5.29 (1h, dd, J=10.9, 3.1 Hz), 5.25–5.15 (5H, m) 5.06 (1H, dd, J=11.2, 3.3 Hz), 5.02 (1H, d, J=3.6 Hz), 4.99–4.92 (2H, m), 4.84–4.81 (2H, m), 4.67 (1H, d, J=7.8 Hz), 4.56–4.51 (2H, m), 4.45–4.38 (3H,m), 4.29 (1H, dd, J=10.6, 3.4 Hz), 4.22–3.95 (13H, m⎯), 3.90–3.77 (3H, m), 2.19–1.92 (51H, m), 1.15 (3H, d, J=6.4 Hz); $^{13}$C-NMR (100 MHz, CDCl$_3$) $\delta$172.40, 171.45, 170.84, 170.54, 170.52, 170.48, 170.45, 170.40, 170.39, 170.34, 170.23, 169.99, 169.82, 169.74, 169.36, 169.00, 145.43, 102.01, 101.17, 98.83, (2C), 98.45, 94.24, 75.65, 74.95, 73.98, 73.64, 73.49, 72.32, 71.84, 71.53, 71.44, 70.81, 70.74, 70.66, 70.12, 69.77, 68.97, 68.71, 68.67, 68.02, 67.97, 67.88, 67.60, 67.35, 64.43, 61.88, 61.81, 61.42, 61.29, 61.04, 56.18, 23.06, 21.02, 20.81, 20.76, 20.68, 20.64, 20.62, 20.58, 20.57, 20.55, 20.49, 20.43, 15.88.

Peracetyl hexasaccharide glycal above (52 mg) was divided into two portions (22 mg and 30 mg). A solution of hexasaccharide glycal (22.0 mg, 13.4 umol) in dry CH$_2$Cl$_2$ (2 mL) under N$_2$ at 0° C., then treated with allyl alcohol (5 mL). The mixture was stirred for 15 h at room temperature. Excess allyl alcohol was removed in vacuo. The other batch (30 mg) was treated similarly. The crude products were combined and chromatographed with 85% EtOAc-CH$_2$Cl$_2$ to give 35.8 mg (66%) of less polar product and 15.7 mg (29%) of more polar product. A 33.2 mg (19 umol) of the less polar material under N$_2$ was dissolved in absolute MeOH (14 mL) and treated with MeONa solution in methanol (165 uL, 25% by weight). After 6 h, the reaction was neutralized with Dowex 50-X8 (200 mg, washed and dried), filtered and concentrated to give quantitative yield of the title compound 19b.

mp 204°–206° (dec); [α']$^{23}_D$=+5.5° (MeOH, c=0.67); IR (MeOH film) 3356 (br), 2923, 1658, 1374, 1071 cm$^{-1}$; $^1$H-NMR (400 MHz, CD$_3$OD) $\delta$5.99–5.93 (1H, m), 5.24 (1H, d, J=3.8 Hz), 5.18–5.14 (1H, m), 4.93 (1H, d, J=3.9 Hz), 4.56–4.54 (2H, m), 4.42–4.06 (10H, m), 3.99 (1H, s), 3.91–3.47 (26H, m), 3.41–3.37 (1H, m), 3.27 (1H, t, J=8.8 Hz), 2.01 (3H, s), 1.24 (3H, d, J=6.5 Hz); $^{13}$C-NMR (100 MHz, CD$_3$OD, ref=$\delta$49.05) $\delta$174.55, 135.73, 117.57, 105.48, 105.42, 103.94, 103.26, 102.79, 101.08, 81.21, 80.67, 80.05, 79.20, 78.09, 76.79, 76.56, 76.48, 76.44, 76.41, 75.54, 74.86, 74.68, 73.57, 72.63, 72.50, 71.57, 71.16, 70.64, 70.41, 69.68, 68.16, 62.67, 62.64, 62.57, 61.96, 61.63, 53.11, 23.58, 16.78.

For the purposes of the preparative synthesis of structure 1b a ceramide precursor was attached to the ABC trisaccharide (Scheme 5). Expoxidation of 7b, followed by reaction with the ceramide precursor 17b (as its tributylstannyl ether) promoted by Zn(OTF)$_2$ provided 20b. Acetylation and PMB removal proceeded smoothly to furnish 21b which is poised for coupling with a suitable DEF trisaccharide donor.

When trisaccharide 15b was treated with MeOTf in the presence of acceptor 21b, a 4:1 mixture of hexasaccharide isomers was obtained. The major product 22b was obtained in 50% yield.

The ceramide side-chain was elaborated by reduction of the azide functionality using Lindlar's catalyst under an atmosphere H$_2$ in the presence of palmitic anhydride to provide 18b directly. Desilylation was followed by dissolving metal deprotection of the sulfonamide and benzyl groups and MeOH quench to remove the carbonate and acetate groups. Peracetylation of the crude mixture afforded a 78% yield of peracetylated bexasaccharide. Saponification of this material using NaOMe provided the natural product 1b in 96% yield. The coupling constants and chemical shifts of the anomeric protons of 1b matched reported data. In addition, the product was characterized by exact mass, and $^1$H and $^{13}$C NMR.

Synthesis of 20b

The benzylated ceramide precursor (475 mg, 1.14 mmol) was dissolved in 4 mL PhH. Bis(tributyltin) ether (0.29 mL, 0.34 g, 0.57 mmol) was added and the reaction vessel (equipped with a Dean-Stark trap) was heated to reflux. After 3 h the reaction was allowed to cool and was concentrated under a flow of N$_2$. In a separate flask, the glycal 7b was dissolved in 1 mL anhydrous CH$_2$Cl$_2$ and the resulting solution was cooled to 0° C. and a solution of 3,3-dimethyldioxirane (2.8 mL, 0.25 mmol, 0.09M in acetone) was added. After 45 min the solution was concentrated under a flow of N$_2$, then under vacuum. The tin ether was dissolved in 1 mL anhydrous THF and added via cannula to a mixture of Zn(OTf)$_2$ (170 mg, 0.468 mmol) in 1 mL THF at −78° C. (wash 1×0.5 mL THF). The reaction was allowed to warm to room temperature over 12 h and then was quenched with distilled water. The aqueous phase was extracted 3× with EtOAc. The combined organic phases were dried over anhydrous MgSO$_4$. Flash column chromatography (3:1 hexane/EtOAc, 3×16 cm silica gel) afforded 265 mg (66%) of the target compound 20b.

$^1$H NMR (CDCl$_3$) $\delta$7.43–7.15 (m, 45H), 7.03 (d, J=8.6 Hz, 2H), 6.79 (d, J=8.6 Hz, 2H), 5.76 (dt, J=6.7, 15.4 Hz, 1H), 5.43 (dd, J=8.5, 15.4 Hz, 1H), 5.07 (d, J=3.5 Hz, 1H), 5.05 (d, J=12.0 Hz, 1H), 4.90 (d, J=12.9 Hz, 2H), 4.83–4.77 (m, 3H), 4.69 (d, J=12.0 Hz, 1H), 4.61 (d, J=11.9 Hz, 1H), 4.54–4.45 (m, 3H), 4.42–4.25 (m, 7H), 4.18–4.05 (m, 6H), 4.01–3.91 (m, 4H), 3.83 (dd, J=4.4, 10.6 Hz, 1H), 3.79 (s, 3H), 3.71–3.65 (m, 4H), 3.57–3.32 (m,7H), 3.20 (m, 1H), 2.29 (bs, 1H), 2.11 (bq, J=6.7 Hz, 2H), 1.42–1.29 (m, 22H), 0.91 (t, J=6.6 Hz, 3H); $^{13}$C NMR (CDCl3) δ158.8, 139.1, 139.0, 138.7, 138.6, 138.34, 138.29, 138.2, 138.1, 130.8, 128.7, 128.55, 128.50, 128.4, 128.33, 128.28, 128.26, 128.12, 128.06, 127.84, 127.76, 127.7, 127.64, 127.60, 127.5, 127.45, 127.36, 125.8, 113.5, 102.7, 100.6, 81.9, 81.5, 79.4, 77.4, 77.0, 76.6, 76.4, 75.5, 74.9, 74.7, 74.4, 73.9, 73.3, 73.2, 73.11, 73.06, 72.3, 72.1, 70.0, 69.4, 68.7, 68.1, 67.9, 67.7, 64.2, 55.2, 32.4, 31.9, 29.70, 29.65, 29.5, 29.4, 29.2, 29.0, 22.7, 14.2; IR (thin film) 3447, 3062, 3029, 2923, 2853, 2099, 1612, 1586, 1514, 1496, 1454, 1364 cm$^{-1}$; [α']$^{23}_D$ +25.0 (c 0.70).

Synthesis of 21b

The above trisaccharide (256 mg, 0.147 mmol) was dissolved in 2 mL anhydrous CH$_2$Cl$_2$. Triethylamine (0.105 mL, 76 mg, 0.753 mmol), DMAP (2 mg, 0.02 mmol) and acetic anhydride (0.042 mL, 45 mg, 0.445 mmol) were added sequentially. The reaction was stirred for 1 h then quenched with saturated aqueous NaHCO$_3$. The extracts were dried with anhydrous MgSO$_4$, filtered and concentrated. Purification by flash column chromatography (4:1 hexane/EtOAc, 2×16 cm silica gel) afforded 235 mg (90%) of the desired compound.

$^1$H NMR (CDCl$_3$) δ7.42–7.17 (m, 45H), 7.03 (d, J=8.6 Hz, 2H), 6.81 (d, J=8.6 Hz, 2H), 5.75 (dt, J=6.7, 15.4 Hz, 1H), 5.43 (dd, J=8.6, 15.4 Hz, 1H), 5.07 (d, J=3.4, 1H), 4.99–4.90 (m, 4H), 4.85 (d, J=11.3 Hz, 2H), 4.77 (d, J=11.9 Hz, 1H), 4.76 (d, J=12.4 Hz, 1H), 4.70 (d, J=12.0 Hz, 1H), 4.62 (d, J=11.7 Hz, 1H), 4.57–4.52 (m, 3H), 4.49–4.34 (m, 7H), 4.30 (d, J=11.8 Hz, 1H), 4.25 (d, J=11.8 Hz, 1H), 4.14–4.06 (m, 7H), 4.01–3.95 (m, 2H), 3.91 (dd, J=5.6, 8.6 Hz, 1H), 3.85 (dd, J=4.3, 11.1, Hz, 1H), 3.80 (s, 3H), 3.74 (d, J=9.8 Hz, 1H), 3.69 (dd, 7.7, 9.9 Hz, 1H), 3.63–3.51 (m, 5H), 3.43–3.34 (m, 3H), 3.22 (dd, J=4.6, 8.2 Hz, 1H), 2.12 (dd, J=6.8, 13.6, 2H), 1.87 (s, 3H), 1.43–1.30 (m, 22H), 0.93, (t, J=6.6 Hz, 3H); $^{13}$C NMR (CDCl$_3$) δ169.3, 158.8, 139.1, 139.0, 138.69, 138.65, 138.6, 138.31, 138.26, 138.2, 138.1, 138.0, 130.8, 128.8, 128.6, 128.41, 128.35, 128.30, 128.28, 128.14, 128.0, 127.9, 127.8, 127.64, 127.60, 127.58, 127.51, 127.47, 127.38, 126.0, 113.5, 102.7, 100.8, 100.6, 81.5, 79.9, 79.5, 79.4, 79.3, 77.4, 77.1, 76.8, 75.5, 75.3, 74.9, 74.5, 74.2, 73.9, 73.2, 73.1, 73.0, 72.4, 72.2, 72.1, 70.2, 69.4, 68.1, 68.0, 67.9, 67.5, 63.8, 55.2, 32.4, 32.0, 29.72, 29.67, 29.5, 29.4, 29.2, 29.1, 22.7, 20.9, 14.2; IR (thin film) 3028, 2923, 2852, 2098, 1751, 1611, 1513, 1496, 1453, 1365, 1232 cm$^{-1}$; [α']$^{23}_D$ +20.3 (c 0.45).

The trisaccharide from above (230 mg, 0.129 mmol) was dissolved in 4 mL CH$_2$Cl$_2$. Distilled water (1 mL) was added and the mixture was cooled to 0° C. DDQ (35 mg, 0.15 mmol) was added and the reaction was stirred for 1 h. The reaction was quenched with saturated aqueous NaHCO$_3$. The aqueous phase was extracted 3× with CH$_2$Cl$_2$. The combined organic phases were washed dried over anhydrous MgSO$_4$. Flash column chromatography (4:1 hexane/EtOAc, 2×16 cm silica) afforded 182 mg (85%) of the target compound 21b.

$^1$H NMR (CDCl$_3$) δ7.38–7.13 (m, 45H), 5.73 (dt, J=6.7, 15.4 Hz, 1H), 5.41 (dd, J=8.6, 15.4 Hz, 1H), 5.09 (d, J=3.2 Hz, 1H), 4.98 (d, J=12.5 Hz, 1H), 4.95 (dd, J=8.0, 9.2 Hz, 1H), 4.87 (d, J=11.2 Hz, 1H), 4.80 (d, J=11.3 Hz, 1H), 4.77 (d, J=10.9 Hz, 1H), 4.70 (d, J=11.4 Hz, 1H), 4.65–4.50 (m, 6H), 4.45–4.42 (m, 3H), 4.38–4.34 (m, 3H), 4.28 (bs, 2H), 4.15 (d, J=11.7 Hz, 1H), 4.11 (d, J=11.8 Hz, 1H), 4.08–4.01 (m, 3H, 3.98–3.94 (m, 3H), 3.88 (dd, J=5.5, 8.5 Hz, 1H), 3.82 (dd, J=4.3, 7.0 Hz, 1H), 3.77 (dd, J=3.1, 10.1 Hz, 1H), 3.70 (d, J=9.8 Hz, 1H), 3.64–3.51 (m, 5H), 3.46 (dd, J=5.4, 9.4, 1H), 3.39 (m, 1H), 3.34–3.30 (m, 2H), 3.21 (dd, J=4.7, 8.4 Hz, 1H), 2.09 (m, 2H), 1.90 (s, 3H), 1.84 (d, J=5.1 Hz, 1H), 1.41–1.27 (m, 22H), 0.90 (t, J=6.5 Hz, 3H); $^{13}$C NMR (CDCl3) δ169.3, 165.9, 139.3, 138.7, 138.6, 138.5, 138.3, 138.2, 138.1, 138.0, 128.5, 128.4, 128.32, 128.27, 128.25, 128.17, 128.00, 127.94, 127.91, 127.8, 127.75, 127.70, 127.67, 127.61, 127.55, 127.49, 127.45, 127.21, 125.9, 107.8, 102.6, 100.8, 99.4, 81.4, 80.6, 79.3, 77.5, 77.3, 77.0, 76.9, 76.7, 75.5, 75.3, 75.2, 74.3, 73.2, 73.1, 73.0, 72.9, 72.3, 72.1, 70.1, 70.0, 69.1, 68.1, 68.0, 67.8, 67.4, 63.8, 32.4, 31.9, 29.7, 29.6, 29.5, 29.4, 29.2, 29.1, 22.7, 20.9, 14.1; IR (thin film) 3570, 3087, 3062, 3029, 2924, 2853 2099, 1950, 1873, 1752, 1496, 1453, 1366, 1231 cm$^{-1}$; [α']$^{23}_D$ +17.6 (c 1.40).

Synthesis of 22b

Thioglycoside 15b (188 mg, 0.151 mmol) and the acceptor 21b (125 mg, 0.0751 mmol) were azeotropically dried with benzene twice. The mixture was then dissolved in 2.6 mL anhydrous Et$_2$O and 1.3 mL CH$_2$Cl$_2$ and to this solution was added 500 mg of 4 Å mol. sieves. This mixture was stirred for 1 h and then was cooled to 0° C. and MeOTf (0.051 mL, 74 mg, 0.45 mmol) was added. The reaction was stirred at 0° C. for 9 h. Triethylamine (1 mL) was then added and reaction was filtered through a plug of silica and washed with Et$_2$O. The filtrate was washed with saturated aqueous NaHCO$_3$ and dried over anhydrous MgSO$_4$. Purification by preparative HPLC (85:15 hexane/EtOAc) afforded 108 mg (50%) of the target compound 22b. The b/a ratio of the reaction was 4:1.

$^1$H NMR (CDCl$_3$) δ7.75 (d, J=7.2 Hz, 2H), 7.46–7.05 (m, 63H), 5.75 (dt, J=6.8, 15.2 Hz, 1HO, 5.43 (dd, J=8.6, 15.5 Hz, 1H), 5.13 (m, 2H), 5.09 (d, 3.6 Hz, 1H), 5.05 (d, J=11.6 Hz, 1H), 5.00 (d, J=11.5 Hz, 1H), 4.94–4.86 (m, 5H), 4.83–4.65 (m, 14H), 4.59 (d, 11.7 Hz, 2H), 4.53–4.43 (m, 6H), 4.39–4.31 (m, 4H), 4.23 (d, J=11.9 Hz, 1H), 4.18 (d, J=11.9 Hz, 1H), 4.15–4.08 (m, 2H), 4.05–3.57 (m, 31H), 3.54 (d, J=9.1 Hz, 1H), 3.49–3.45 (m, 2H), 3.38 (m, 1H), 3.31–3.23 (m, 3H), 2.92–2.89 (m, 2H), 2.75 (bt, 6.0H, H), 2.12 (bq, J=6.9 Hz, 2H), 1.85 (s, 3H), 1.20–1.09 (m, 42H), 0.92 (t, J=6.6 Hz, 3H); $^{13}$C NMR (CDCl3) δ169.1, 165.9, 155.5, 140.9, 139.2, 139.0, 138.8, 138.64, 138.59, 138.47, 138.43, 138.3, 138.2, 138.10, 138.07, 138.0, 132.1, 129.1, 128.69, 128.65, 128.56, 128.43, 128.40, 128.36, 128.35, 128.26, 128.17, 128.12, 128.08, 127.97, 127.77, 127.66, 127.64, 127.60, 127.54, 127.49, 127.45, 127.41, 127.3, 126.0, 103.0, 102.7, 100.8, 99.7, 99.2, 98.0, 81.2, 80.6, 79.5, 79.2, 79.0, 78.3, 77.7, 76.8, 76.5, 75.5, 75.3, 75.1, 75.03, 74.97, 74.91, 74.87, 74.0, 73.2, 73.10, 73.07, 72.98, 72.93, 72.6, 72.3, 72.1, 72.0, 71.32, 71.25, 70.2, 69.4, 69.32, 69.25, 68.1, 67.9, 67.5, 68.3, 62.1, 62.0, 56.1, 32.4, 31.9, 29.71, 29.68, 29.66, 29.48, 29.38, 29.2, 29.1, 22.7, 20.7, 18.13, 18.11, 18.01, 17.98, 16.9, 14.2, 11.9; IR (thin film) 3344, 3030, 2924, 2864, 2101, 1789, 1754, 1496, 1453, 1366, 1232 cm$^{-1}$.

Synthesis of 18b

The hexasaccharide 22b (66 mg, 0.023 mmol) was dissolved in 1 mL EtOAc. Lindlar's catalyst (66 mg) was added followed by the addition of palmitic anhydride (23 mg, 0.046 mmol). The system was purged under vacuum and then put under 1 atm of H$_2$. After 24 h the reaction was filtered through a plug of silica gel, washed with EtOAc, and concentrated. Purification by preparative HPLC (4:1 hexane/EtOAc) afforded 64 mg (90%) of the desired product 18b.

$^1$H NMR (CDCl$_3$) δ7.72 (d, J=7.2 Hz, 2H), 7.42–7.02 (m, 63H), 5.65 (d, J=9.1 Hz, 1H), 5.62 (dt, J=6.6, 15.3 Hz, 1H), 5.31 (dd, J=8.6, 15.3 Hz, 1H), 5.10 (m, 2H), 5.05 (d, J=3.6 Hz, 1H), 5.02 (d, J=11.5 Hz, 1H), 4.96 (d, J=11.4 Hz, 1H), 4.90–4.62 (m, 13H), 4.57–4.38 (m, 8H), 4.32–4.26 (m, 3H), 4.21–4.07 (m, 9H), 4.01–3.41 (m, 31H), 3.30 (m, 1H), 3.23 (m, 3H), 2.20 (m, 4H), 1.82 (s, 3H), 1.52 (bm, 2H), 1.32–1.19 (m, 53H), 1.15–1.08 (m, 42H), 0.88 (t, J=6.8 Hz, 6H); IR (thin film) 3531, 3346, 3063, 3030, 2924, 2854, 1790, 1748, 1674, 1496, 1454, 1365, 1236 cm$^{-1}$; $[\alpha']^{23}_D$ −17.9 (c 0.65).

Synthesis of 1b

The hexasaccharide from above (20 mg, 0.0065 mmol) was dissolved in 0.5 mL THF. A solution of tetrabutylammonium fluoride (1.0M in THF, 0.050 mL, 0.050 mmol) was added and the reaction was stirred for 2 h. The solution was filtered through a plug of silica, washed with EtOAc and concentrated. The residue was dissolved in 1 mL of anhydrous MeOH and NaOMe (10 mg, 0.19 mmol) was added. The reaction was stirred for 3 h, neutralized with 40 mg of Dowex-50 resin, filtered and concentrated. Purification by flash column chromatography (1.5×4 cm 10–40 u silica gel, 95:5 CH$_2$Cl$_2$/MeOH) afforded 16.5 mg (94%) of the desired compound.

$^1$H NMR (CDCl$_3$) δ7.78 (d, J=7.6 Hz, 2H), 7.46 (d, J=7.4 Hz, 2H), 7.41–6.97 (m, 61H), 6.02 (d, J=9.1 Hz, 1H), 5.76 (bs, 1H), 5.67 (dt, J=6.6, 15.3 Hz, 1H), 5.37–5.30 (m, 2H), 5.19 (d, J=2.6 Hz, 1H), 4.96 (d, J=11.3 Hz, 1H), 4.93 (d, J=3.4 Hz, 1H), 4.90–4.83 (m, 3H), 4.78–4.66 (m, 7H), 4.56 (d, J=11.1 Hz, 1H), 4.53 (d, J=10.2 Hz, 1H), 4.47–4.32 (m, 5H), 4.28–4.06 (m, 14H), 4.01–3.13 (m, 36H), 2.73 (bt, 1H), 2.61 (bs, 1H), 2.54 (bs, 1H), (2.05 (m, 4H), 1.50 (m, 2H), 1.38–1.23 (m, 46H), 0.88 (t, J=6.6 Hz, 6H), 0.78 (d, 6.3 Hz, 3H); $^{13}$C NMR (CDCl3) δ173.4, 142.4, 139.5, 139.0, 138.7, 138.5, 138.33, 138.26, 138.14, 138.09, 137.9, 137.2, 137.1, 131.6, 129.0, 128.8, 128.54, 128.47, 128.37, 128.32, 128.27, 128.22, 128.17, 128.14, 128.05, 127.99, 127.79, 127.73, 127.68, 127.63, 127.59, 127.49, 127.46, 127.37, 127.32, 126.98, 126.58, 104.1, 102.83, 102.76, 100.3, 100.2, 82.1, 81.5, 81.2, 79.6, 79.2, 79.0, 78.0, 77.3, 77.0, 76.7, 75.6, 75.3, 75.1, 75.0, 74.8, 74.6, 73.5, 73.4, 73.2, 73.0, 72.7, 72.6, 71.9, 70.1, 69.6, 68.5, 68.2, 68.0, 67.5, 62.4, 61.9, 54.8, 52.3, 36.9, 32.3, 31.9, 29.71, 29.67, 29.54, 29.50, 29.43, 29.37, 29.28, 29.20, 25.7, 22.7, 16.7, 14.1; IR (thin film) 3424, 3062, 3023, 2923, 2852, 1641, 1530, 1496, 1453, 1362, 1325 cm$^{-1}$; $[\alpha']^{23}_D$ −3.2 (c 0.83).

A flask was equipped with a dry ice condenser and was charged with 4 mL NH$_3$. Sodium (18 mg, 0.78 mol) was added and to the resulting blue solution was added 29 mg of the above hexasaccharide (0.010 mmol). The reaction was stirred at −78° C. for 45 min. Quench by the addition of MeOH (3 mL). Nitrogen was blown over the solution to evaporate the NH$_3$. The reaction was neutralized with 170 mg of Dowex-50 resin, filtered and concentrated. The resulting residue was dissolved in 1 mL of 4:1 THF/DMF. Triethylamine (0.5 mL) was added followed by the addition of DMAP (3 mg) and acetic anhydride (0.200 mL). After 2 h the reaction was concentrated in vacuo. Purification by flash column (1.5×5 cm 10–40 m silica, 9:1 EtOAc/hexane) afforded 18 mg (78%) of the peracetate. A sample of this hexasaccharide (15 mg, 0.0065 mmol) was dissolved in 0.5 mL of anhydrous MeOH and a NaOMe solution (30% in MeOH, 0.010 mL, 0.05 mmol) was added. The solution was stirred for 3 h, neutralized with 9 mg Dowex-50 resin, filtered and concentrated. The residue was purified by flash column chromatography (1.5×4 cm C-18 reverse phase silica, MeOH) to afford 9.6 mg of the natural product 1. Spectral data agree with those reported by Hakomori, et al.

Biological Results

The MBR1 hexasaccharide has been prepared in two forms, the natural "B" form and the unnatural "A" form as shown below.

The natural structure ("β") is:

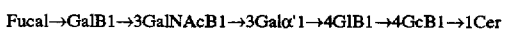

The unnatural structure "α" is:

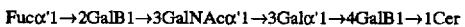

Both have been linked to ceramide to facilitate testing for immunological reactivity with monoclonal antibody (mAb) MBr1.

By Thin Layer Chromatography (TLC) the 2 preparations migrate as similar single bands. Immune TLC (see Ritter, G., et al., Cancer Res. 50, 1403–10 (1990)) demonstrates that both forms react with the MBr1 monoclonal antibody specifically but that the β-form reacts 10 times more strongly (comparable staining is seen with 1/10 the amount of antigen). The high level of reactivity of the β structure with mAb MBr1 was confirmed using flow cytometry inhibition assays. Reactivity of MAb MBr1 with breast cancer cell lines such as MCF-7 was 98% inhibited by 8 μg/ml of the β linkage preparation but was only 6% inhibited by 8 μg of the α-linkage preparation. GD3 ganglioside (negative control) showed no inhibition at all.

What is claimed is:

1. A process for synthesizing a compound having the structure:

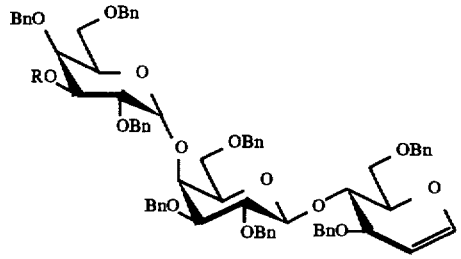

wherein R is H which comprises:

(a) (i) reacting a compound having the structure:

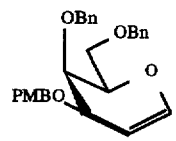

with an epoxidizing agent under suitable conditions to form an epoxide;

(ii) cleaving the epoxide formed in step (a) (i) under suitable conditions with R$_4$NF wherein each R is independently the same or different and is a linear or branched chain alkyl, aralkyl or aryl group to form a fluoroalcohol; and (iii) alkylating the fluoroalcohol formed in step (b) (ii) under suitable conditions with a non-nucleophilic base and an organic halide having the formula C$_6$H$_5$CH$_2$X wherein X is Br, Cl, I or F to form a compound having the structure:

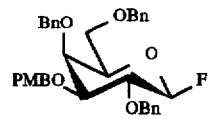

63

(b) treating a compound having the structure:

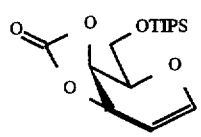

with an epoxidizing agent under suitable conditions to form an epoxide; and (c) coupling the epoxide formed in step (b) with a compound having the structure:

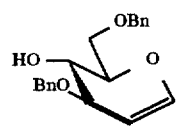

under suitable conditions to form a compound having the structure:

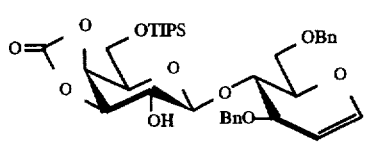

(d) (i) alkylating the compound formed in step (c) (ii) under suitable conditions with a non-nucleophilic base and an organic halide having the formula $C_6H_5CH_2X$ wherein X is Br, Cl, I or F; and (ii) de-silylating the compound formed in step (d) (i) under suitable conditions with $R_4NF$ wherein each R is independently the same or different and is a linear or branched chain alkyl, aralkyl or aryl group;

(iii) treating the compound formed in step (d) (ii) under suitable conditions with a metal alkoxide to form a deprotected disaccharide; and (iv) alkylating the disaccharide formed in step (d) (iii) under suitable conditions to form a selectively deprotected disaccharide having the structure:

64

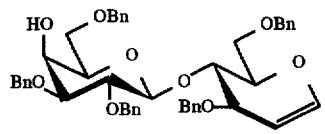

(e) (i) coupling the selectively deprotected disaccharide formed in step (d) (iv) with the compound formed in step (a) (iii) under suitable conditions to form a protected trisaccharide; and (ii) de-protecting the protected trisaccharide formed in step (e) (i) under suitable conditions to form a trisaccharide having the structure:

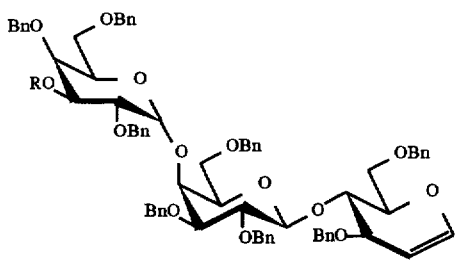

wherein R is H.

2. A process for synthesizing a trisaccharide ceramide having the structure:

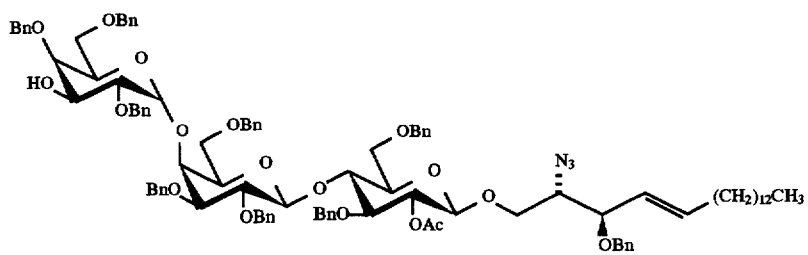

which comprises:

(a) synthesizing a trisaccharide having the structure

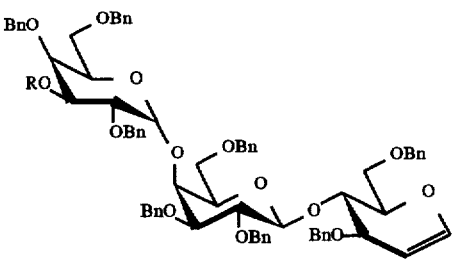

wherein R is PMB;

(b) (i) reacting the trisaccharide formed in step (a) with an epoxidizing agent under suitable conditions to form a trisaccharide epoxide; and (ii) reacting the trisaccharide epoxide formed in step (b) (i) with a compound having the structure:

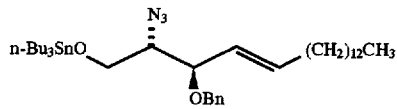

under suitable conditions to form a protected trisaccharide ceramide having the structure:

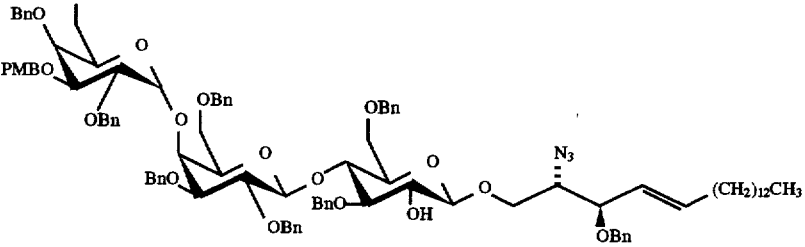

(c) (i) acylating the ceramide formed in step (b) (ii) under suitable conditions; and (ii) selectively de-protecting the compound formed in step (c) (i) under suitable conditions to form the trisaccharide ceramide.

3. A process for synthesizing a mercaptotrisaccharide having the structure:

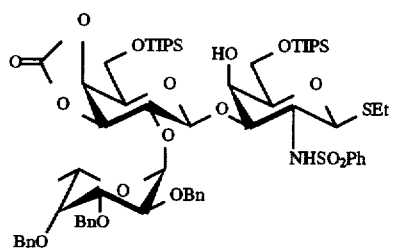

which comprises:

(a) coupling a compound having the structure:

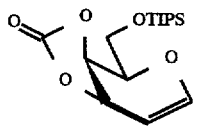

with a compound having structure:

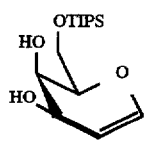

under suitable conditions to form a disaccharide having the structure:

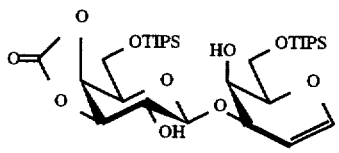

(b) coupling the disaccharide formed in step (a) (ii) with a compound having the structure:

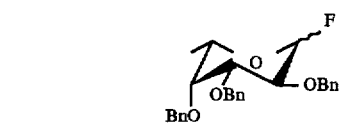

under suitable conditions to form a trisaccharide having the structure:

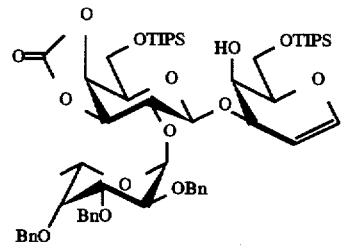

(c) iodosulfonamidating the trisaccharide formed in step (b) under suitable conditions to form a iodosulfonamide having the structure:

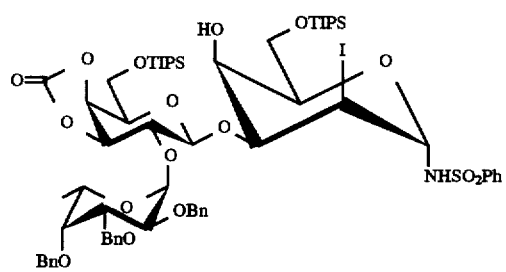

and (d) reacting the iodosulfonamide formed in step (c) under suitable conditions with a thiolate to form the mercaptotrisaccharide.

4. A process of synthesizing a hexasaccharide ceramide having the structure:

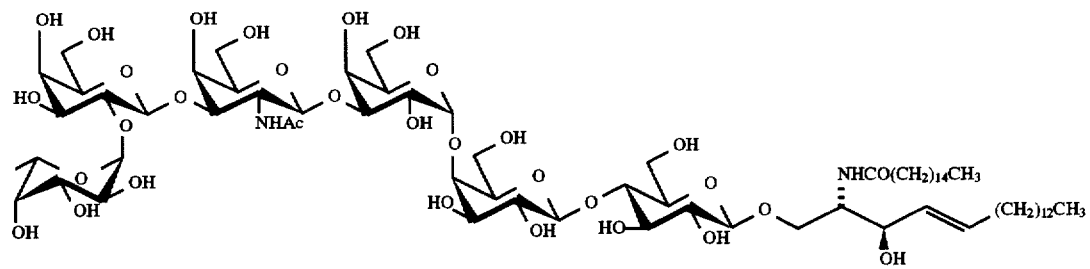

which comprises:

(a) coupling a compound having the structure:

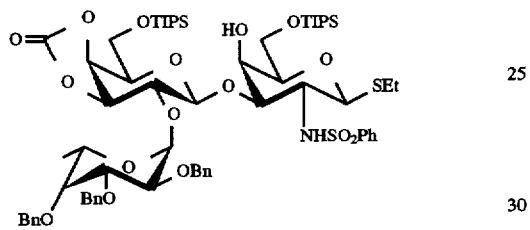

with a compound having the structure:

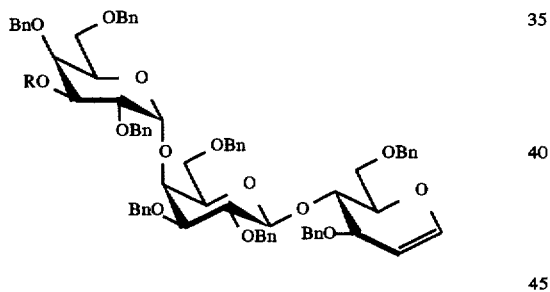

under suitable conditions to form a compound having the structure:

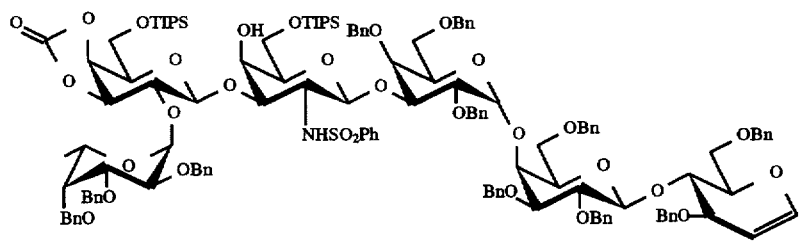

(b) (i) reacting the compound formed in step (a) with an epoxidizing agent under suitable conditions to form a hexasaccharide epoxide; and (ii) reacting the hexasaccharide epoxide with a stannyl ether having the structure:

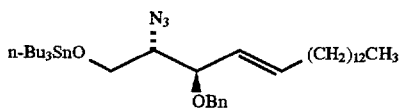

under suitable conditions to form a hexasaccharide alcohol;

(c) acylating the hexasaccharide alcohol formed in step (b) (ii) under suitable conditions to form a hexasaccharide acetate having the structure:

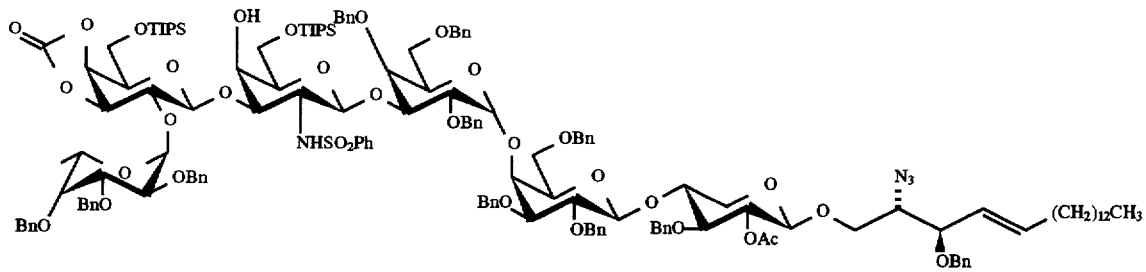

(d) reductively acylating the hexasaccharide acetate formed in step (c) under suitable conditions in the presence of palmitic anhydride to form a hexasaccharide ceramide;

(e) desilylating the hexasaccharide ceramide under suitable conditions to form a partially deprotected hexasaccharide ceramide;

(f) (i) reducing the partially deprotected hexasaccharide ceramide under suitable conditions to form a deprotected hexasaccharide ceramide acetate; and (ii) acylating the deprotected hexasaccharide ceramide acetate under suitable conditions to form a hexasaccharide ceramide peracetate; and (g) saponifying the hexasaccharide ceramide peracetate under suitable conditions to form the hexasaccharide ceramide.

5. A process of synthesizing a hexasaccharide ceramide having the structure:

which comprises:

(a) coupling a compound having the structure:

with a compound having the structure:

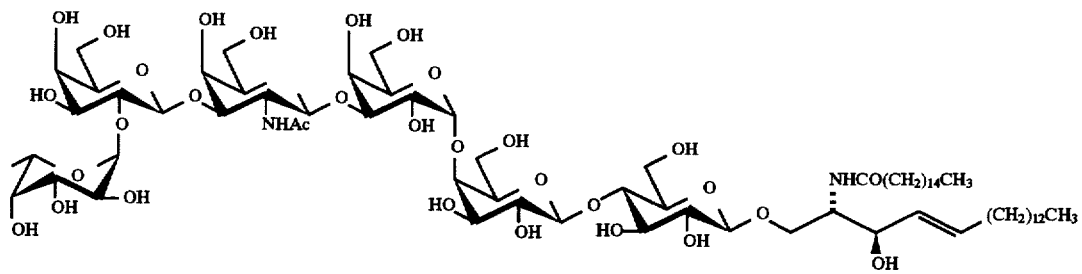

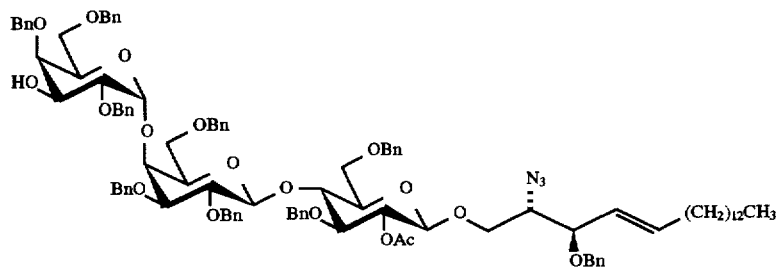

under suitable conditions to form a hexasaccharide having the structure:

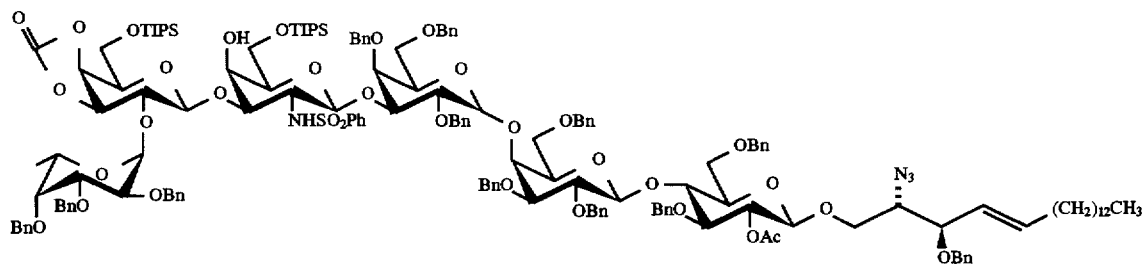

(b) (i) reducing the hexasaccharide formed in step (a) under suitable conditions in the presence of palmitic anhydride to form a palmitoyl amide;

(ii) desilylating the palmitoyl amide with $R_4NF$ wherein each R is independently the same or different and is a linear or branched chain alkyl, aralkyl or aryl group under suitable conditions to form a partially deprotected hexasaccharide;

(iii) de-protecting the hexasaccharide formed in step (b) (ii) under suitable conditions to form a deprotected hexasaccharide;

(iv) acylating the hexasaccharide formed in step (b) (iii) under suitable conditions to form a hexasaccharide ceramide peracetate; and (iv) saponifying the hexasaccharide ceramide peracetate under suitable conditions to form the hexasaccharide ceramide.

6. A process of synthesizing an allyl hexasaccharide having the structure:

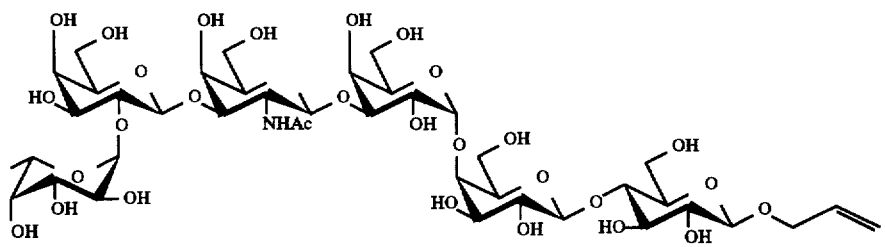

which comprises:

(a) coupling a compound having the structure:

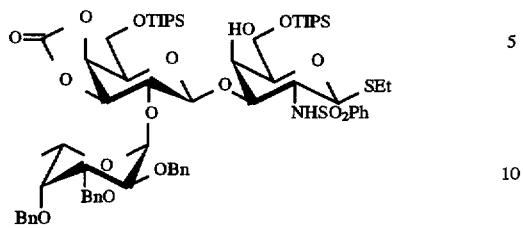

with a compound having the structure:

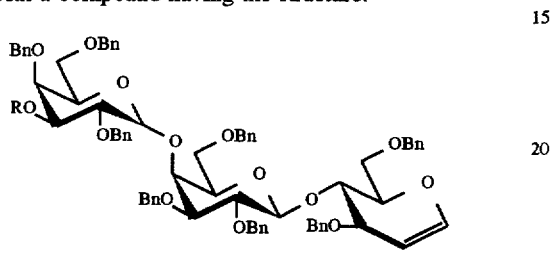

wherein R is H under suitable conditions to form a hexasaccharide having the structure:

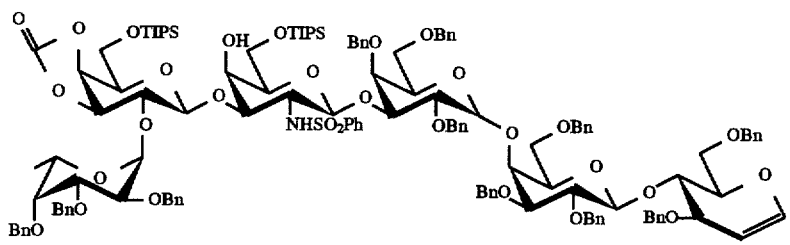

(b) (i) desilylating the compound formed in step (a) with $R_4NF$ wherein each R is independently the same or different and is a linear or branched chain alkyl, aralkyl or aryl group under suitable conditions to form a partially deprotected hexasaccharide;

(ii) de-protecting the hexasaccharide formed in step (b) (i) under suitable conditions to form a deprotected hexasaccharide; and (iii) peracylating the compound formed in step (b) (ii) under suitable conditions to form a hexasaccharide peracetate having the structure:

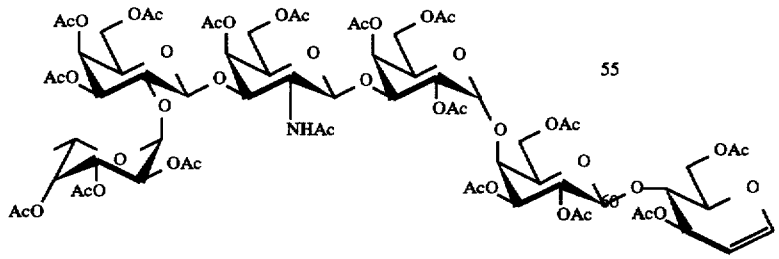

(c) (i) reacting the hexasaccharide peracetate formed in step (b) (iii) with an epoxidizing agent under suitable conditions to form an hexasaccharide epoxide peracetate;

(ii) treating the hexasaccharide epoxide peracetate formed in step (c) (i) with allyl alcohol under suitable conditions to form an allyl hexasaccharide peracetate; and (iii) saponifying the allyl hexasaccharide peracetate under suitable conditions to form the allyl hexasaccharide.

7. A process of synthesizing a hexasaccharide having the structure:

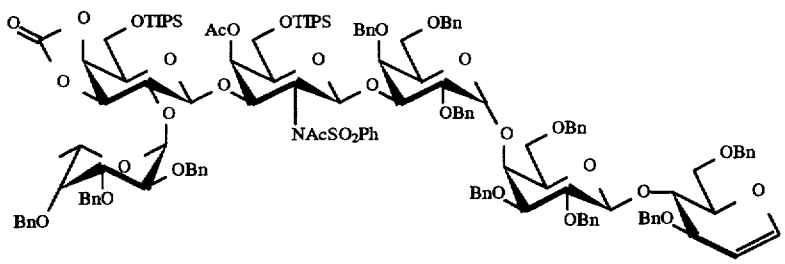

which comprises:

(a) coupling a compound having the structure:

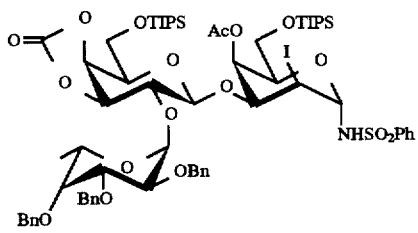

with a compound having the structure:

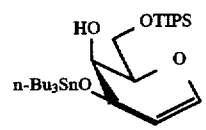

under suitable conditions to form a compound having the structure:

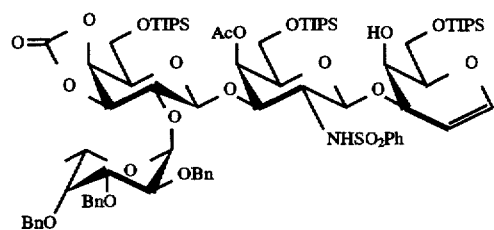

(b) (i) acylating the compound formed in step (a) under suitable conditions; and (ii) reacting the compound formed in step (b) (i) with an epoxidizing agent under suitable conditions to form an epoxide having the structure:

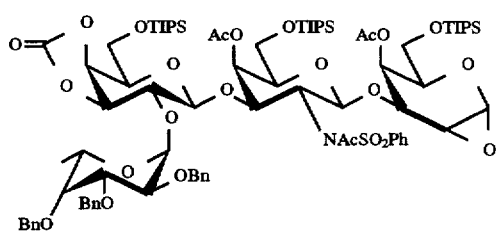

(c) (i) treating the epoxide with $R_4NF$ wherein each R is independently the same or different and is a linear or branched chain alkyl, aralkyl or aryl group under suitable conditions; and (ii) alkylating the compound formed in step (c) (i) under suitable conditions to form a compound having the structure:

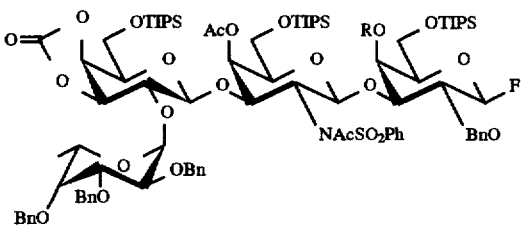

wherein R is H or acyl;

(d) coupling the compound formed in step (c) (ii) with a compound having the structure:

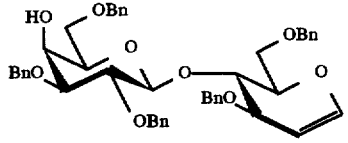

under suitable conditions to form the hexasaccharide.

* * * * *